United States Patent
Frattini et al.

(10) Patent No.: US 10,501,440 B2
(45) Date of Patent: Dec. 10, 2019

(54) HETEROARYLCARBOXAMIDE DERIVATIVES AS PLASMA KALLIKREIN INHIBITORS

(71) Applicant: Boehringer Ingelheim International GmbH, Ingelheim am Rhein (DE)

(72) Inventors: Sara Frattini, Castelleone (IT); Iain Lingard, Monza (IT); Dieter Wolfgang Hamprecht, North Curl Curl (AU); Remko Alexander Bakker, Biberach an der Riss (DE); Matthias Eckhardt, Biberach an der Riss (DE); Andreas Gollner, Vienna (AT); Joerg P. Hehn, Biberach an der Riss (DE); Elke Langkopf, Biberach an der Riss (DE); Holger Wagner, Mettenberg (DE); Bernd Wellenzohn, Friedrichshafen (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/953,523

(22) Filed: Apr. 16, 2018

(65) Prior Publication Data

US 2018/0305339 A1    Oct. 25, 2018

(30) Foreign Application Priority Data

Apr. 21, 2017  (EP) .................................... 17167549

(51) Int. Cl.
| | | |
|---|---|---|
| *C07D 401/14* | (2006.01) | |
| *A61K 31/444* | (2006.01) | |
| *A61K 31/506* | (2006.01) | |
| *A61K 45/06* | (2006.01) | |
| *A61P 3/10* | (2006.01) | |

(52) U.S. Cl.
CPC .......... *C07D 401/14* (2013.01); *A61K 31/444* (2013.01); *A61K 31/506* (2013.01); *A61K 45/06* (2013.01); *A61P 3/10* (2018.01)

(58) Field of Classification Search
CPC ........................... C07D 401/14; A61K 31/444
USPC .......... 544/324, 333; 546/112; 514/275, 299
See application file for complete search history.

(56) References Cited

FOREIGN PATENT DOCUMENTS

| WO | 2013111108 A1 | 8/2013 |
| WO | 2014188211 A1 | 11/2014 |
| WO | 2017072021 A1 | 5/2017 |

OTHER PUBLICATIONS

International Search Report and Written Opinion for PCT/EP2018059633 dated Jul. 6, 2018.

*Primary Examiner* — Deepak R Rao
(74) *Attorney, Agent, or Firm* — David L. Kershner

(57) ABSTRACT

Disclosed are heteroarylcarboxamides of formula (I),

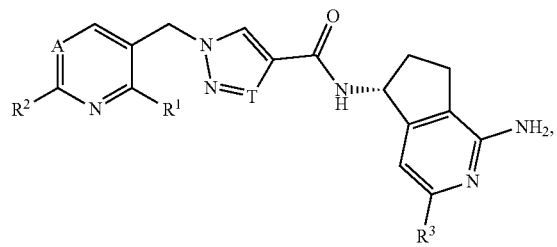

and pharmaceutically acceptable salts thereof, wherein A, T, $R^1$, $R^2$ and $R^3$ are as defined herein. Also disclosed are methods of using these compounds for the treatment of diseases which can be influenced by inhibition of plasma kallikrein.

14 Claims, No Drawings

HETEROARYLCARBOXAMIDE DERIVATIVES AS PLASMA KALLIKREIN INHIBITORS

FIELD OF THE INVENTION

This invention relates to novel 5-membered heteroarylcarboxamide derivatives, and pharmaceutically acceptable salts thereof, that are plasma kallikrein inhibitors. In addition, the invention relates to pharmaceutical compositions and combinations comprising said compounds and to their use in methods for the treatment of diseases which can be influenced by the inhibition of plasma kallikrein. Particularly, the pharmaceutical compositions of the invention are suitable for the prophylaxis and/or therapy of diabetic complications, particularly for the treatment of retinal vascular permeability associated with diabetic retinopathy and diabetic macular edema.

BACKGROUND OF THE INVENTION

Plasma kallikrein is a trypsin-like serine protease secreted by hepatocytes in the liver as an inactive plasma prekallikrein that circulates in plasma either as a free zymogen or as a heterodimer complex bound to high molecular weight kininogen which is activated to give the active plasma kallikrein that can liberate kinins from kininogens in addition to processing other substrates. Kinins are potent mediators of inflammation that act through G protein-coupled receptors such as bradykinin receptors.

Plasma kallikrein is thought to play a role in a number of inflammatory disorders and may have numerous implications in disorders such as hereditary angioedema (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization, posterior vitreous detachment (PVD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema, drug-related (ACE-inhibitors) edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, deep vein thrombosis, coagulation from post fibrinolytic treatments, angina, angioedema, sepsis, arthritis (e.g. rheumatoid arthritis, osteoarthritis, infection arthritis), lupus, gout, psoriasis, inflammatory bowel, diabetes, diabetic complications, complications arising from metabolic syndrome, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma), allergic edema e.g. airflow obstruction in chronic allergic sinusitis or perennial rhinitis; airflow obstruction in acute asthma; serositis associated with systemic lupus erythematosus (SLE), acute respiratory distress syndrome (ARDS) and other diseases.

Plasma kallikrein inhibitors are considered to be useful in the treatment of a wide range of disorders, particularly in the treatment of edema formation in diseases, e.g. edema formation related to ischemic reperfusion injuries, retinopathy or edema-associated diseases, such as hereditary angioedema, macular edema and brain edema. Plasma kallikrein inhibitors are considered to be especially useful in the treatment of retinopathy, e.g. retinopathy associated with diabetes and/or hypertension, and in the treatment of macular edema, e.g. macular edema associated with diabetes and/or hypertension.

Plasma kallikrein inhibitors suitable for therapeutic use should bind potently and with high selectivity to plasma kallikrein. They should be well absorbed from the gastrointestinal tract, be sufficiently metabolically stable and possess favorable pharmacokinetic properties. They should be non-toxic and demonstrate few side-effects.

The compounds of the invention are plasma kallikrein inhibitors and are therefore potentially useful in the treatment of disorders mentioned hereinbefore, particularly should have utility as a treatment to reduce retinal vascular permeability associated with diabetic retinopathy and diabetic macular edema retinopathy or edema-associated diseases.

Other complications of diabetes such as cerebral haemorrhage, nephropathy, cardiomyopathy and neuropathy, all of which have associations with plasma kallikrein may also be considered as targets for a plasma kallikrein inhibitor.

Low molecular weight plasma kallikrein inhibitors are known in the art, for example, the compounds disclosed in WO 2013/111108, WO 2013/11107 and WO 2014/188211.

SUMMARY OF THE INVENTION

In a first aspect, the present invention relates to a compound of formula (I)

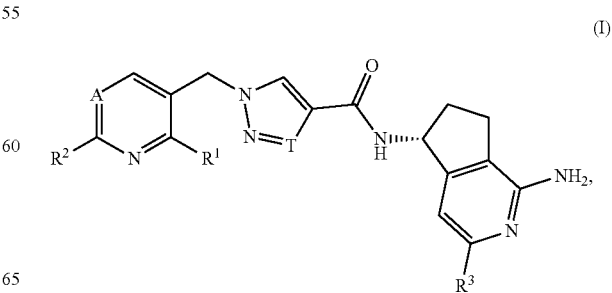

wherein
A is selected from the group A-G1 consisting of N and CH;
T is selected from the group T-G1 consisting of N, C—H, $C_{1-4}$-alkyl, C—$CHF_2$, C—$CF_3$ and C—$OCH_3$;
$R^1$ is selected from the group $R^1$-G1 consisting of $C_{1-3}$-alkyl;
$R^2$ is selected from the group $R^2$-G1 consisting of a fused or spiro bicyclic ring system consisting of 1 N atom and 5 to 6 C atoms as ring members,
wherein the ring system is attached via the N atom to the monocyclic heteroaromatic ring in formula (I) and
wherein the ring system is optionally substituted with one substituent selected from the group consisting of F, $C_{1-3}$-alkyl, $CF_3$, CN, HO—$C_{1-3}$-alkyl- and $C_{1-3}$-alkyloxy- and
wherein the ring system is optionally additionally substituted with one substituent selected from the group consisting of F and $CH_3$; and
$R^3$ is selected from the group $R^3$-G1 consisting of H, $CH_3$, $CHF_2$ or $CF_3$,
wherein in any definition mentioned hereinbefore and if not specified otherwise, any alkyl group or sub-group may be straight-chained or branched,
the isoforms, tautomers, stereoisomers, metabolites, prodrugs, solvates, hydrates, and the salts thereof, particularly the pharmaceutically acceptable salts thereof, or the combinations thereof.

In a second aspect, the present invention relates to a pharmaceutical composition comprising one or more compounds of formula (I), as defined hereinbefore or hereinafter, or pharmaceutically acceptable salts thereof, optionally together with one or more inert carriers and/or diluents.

In a third aspect, the present invention relates to a pharmaceutical composition comprising one or more compounds of formula (I), as defined hereinbefore or hereinafter, or pharmaceutically acceptable salts thereof, and one or more additional therapeutic agents, optionally together with one or more inert carriers and/or diluents.

In a fourth aspect, the present invention relates to a compound of formula (I), as defined hereinbefore or hereinafter, or a pharmaceutically acceptable salt thereof for use as a medicament.

In a fifth aspect, the present invention relates to a method for the treatment of diseases or conditions which can be influenced by the inhibition of plasma kallikrein in a patient in need thereof, the method being characterized in that one or more compounds of formula (I), as defined hereinbefore or hereinafter, or pharmaceutically acceptable salts thereof are administered to the patient.

Also, the present invention relates to the use of one or more compounds of formula (I), as defined hereinbefore or hereinafter, in the manufacture of a medicament for the treatment of diseases or conditions which can be influenced by the inhibition of plasma kallikrein.

Also, the present invention relates to a compound of formula (I), as defined hereinbefore or hereinafter, or a pharmaceutically acceptable salt thereof for use in a method for the treatment of diseases or conditions which can be influenced by the inhibition of plasma kallikrein, in a patient in need thereof.

Further aspects of the present invention will become apparent to the person skilled in the art directly from the foregoing and following description and the examples.

General Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

Also, unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

Salts of other acids than those mentioned above which for example are useful for purifying or isolating the compounds of the present invention (e.g. trifluoro acetate salts) also comprise a part of the invention.

In case a compound of the present invention is depicted in form of a chemical name and as a formula in case of any discrepancy the formula shall prevail.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

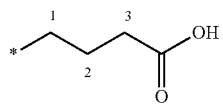

wherein the carboxy group is attached to the third carbon atom of the propyl group. The terms "1-methylpropyl-", "2,2-dimethylpropyl-" or "cyclopropylmethyl-" group represent the following groups:

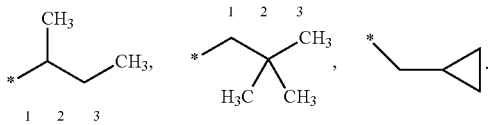

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In a definition of a group, the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

The term "$C_{3-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{3-n}$-cycloalkyl", wherein n is an integer 3 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term halogen generally denotes fluorine, chlorine, bromine and iodine.

Many of the terms given above may be used repeatedly in the definition of a formula or group and in each case have one of the meanings given above, independently of one another.

The terms "treatment" and "treating" as used herein embrace both therapeutic, i.e. curative and/or palliative, and preventive, i.e. prophylactic, treatment.

Therapeutic treatment refers to the treatment of patients having already developed one or more of said conditions in manifest, acute or chronic form. Therapeutic treatment may be symptomatic treatment in order to relieve the symptoms of the specific indication or causal treatment in order to reverse or partially reverse the conditions of the indication or to stop or slow down progression of the disease.

Preventive treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition or disorder as well as to alleviate the symptoms or complications associated with the disease, condition or disorder.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

DETAILED DESCRIPTION OF THE INVENTION

The present invention discloses novel 5-membered heteroarylcarboxamide derivatives, which are effective plasma kallikrein inhibitors and possess suitable pharmacological and pharmacokinetic properties to use them as medicaments for the treatment of diseases and/or conditions that may be influenced by plasma kallikrein inhibition, including but not limited to diabetic complications, for example diabetic retinopathy and diabetic macular edema, retinopathy, or edema-associated diseases.

The compounds of the present invention may provide several advantages, such as enhanced potency, high metabolic and/or chemical stability, high selectivity, safety and tolerability, enhanced solubility, enhanced permeability, desirable plasma protein binding, enhanced bioavailability, improved pharmacokinetic profiles, and the possibility to form stable salts.

Compounds of the Invention

In a first aspect of the present invention, it is found that compounds of formula (I)

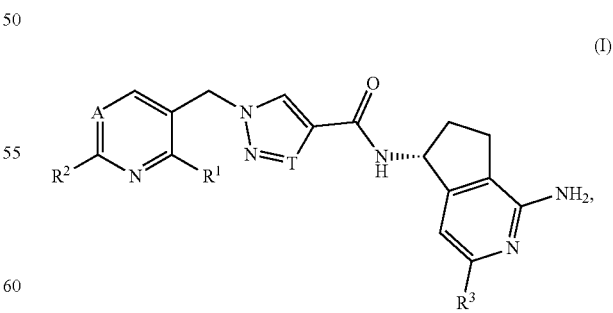

wherein A, T, $R^1$, $R^2$, and $R^3$ are defined as hereinbefore and hereinafter, are potent inhibitors of plasma kallikrein and exhibit favorable properties with regard to selectivity, safety and tolerability, metabolic and/or chemical stability, pharmacokinetic and physicochemical characteristics, solubility, permeability, plasma protein binding, bioavailability and the possibility to form stable salts.

Therefore, the compounds of formula (I), as defined hereinbefore or hereinafter, or pharmaceutically acceptable salts thereof are expected to be useful in the treatment of diseases and/or conditions which can be influenced by plasma kallikrein inhibition.

Thus, according to one aspect of the present invention, a compound of formula (I)

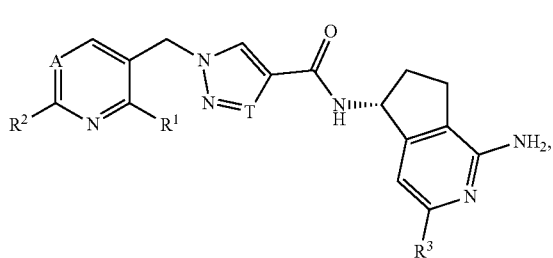

(I)

wherein A, T, $R^1$, $R^2$, and $R^3$ are defined as hereinbefore or hereinafter, or a salt thereof is provided as well as the isoforms, tautomers, stereoisomers, metabolites, prodrugs, solvates, hydrates, and the salts thereof, particularly the pharmaceutically acceptable salts thereof.

Unless otherwise stated, the groups, residues and substituents, particularly A, T, $R^1$, $R^2$ and $R^3$ are defined as hereinbefore and hereinafter. Some preferred meanings of the substituents A, T, $R^1$, $R^2$, and $R^3$ will be given hereinafter as embodiments of the invention. Any and each of these definitions and embodiments may be combined with one another.

A:
According to one embodiment, A is selected from the group A-G1 consisting of N and CH.
According to another embodiment, A is selected from the group A-G2 consisting of CH.
According to another embodiment, A is selected from the group A-G3 consisting of N.

T:
According to one embodiment, T is selected from the group T-G1 consisting of N, C—H, C—$C_{1-4}$-alkyl, C—$CHF_2$, C—$CF_3$ and C—$OCH_3$.
According to another embodiment, T is selected from the group T-G2 consisting of N, C—H, C—$CH_3$, C—$CH_2CH_3$, C—$CH_2CH_2CH_3$, C—$CH(CH_3)_2$, C—$CHF_2$, C—$CF_3$ and C—$OCH_3$.
According to another embodiment, T is selected from the group T-G3 consisting of N, C—H, C—$CH_3$, C—CH$(CH_3)_2$, C—$CHF_2$, C—$CF_3$ and C—$OCH_3$.
According to another embodiment, T is selected from the group T-G4 consisting of C—$CH_3$, C—$CH(CH_3)_2$, C—$CHF_2$, C—$CF_3$ and C—$OCH_3$.
According to another embodiment, T is selected from the group T-G5 consisting of C—H.
According to another embodiment, T is selected from the group T-G6 consisting of N.

$R^1$:
According to one embodiment, $R^1$ is selected from the group $R^1$-G1 consisting of $C_{1-3}$-alkyl.
According to another embodiment, $R^1$ is selected from the group $R^1$-G2 consisting of $CH_3$ and $CH_2CH_3$.
According to another embodiment, $R^1$ is selected from the group $R^1$-G3 consisting of $CH_3$.

$R^2$:
According to one embodiment, $R^2$ is selected from the group $R^2$-G1 consisting of
a fused or spiro bicyclic ring system consisting of 1 N atom and 5 to 6 C atoms as ring members,
wherein the ring system is attached via the N atom to the monocyclic heteroaromatic ring in formula (I) and
wherein the ring system is optionally substituted with one substituent selected from the group consisting of F, $C_{1-3}$-alkyl, $CF_3$, CN, HO—$C_{1-3}$-alkyl- and $C_{1-3}$-alkyloxy- and
wherein the ring system is optionally additionally substituted with one substituent selected from the group consisting of F and $CH_3$.

According to another embodiment, $R^2$ is selected from the group $R^2$-G2 consisting of
a fused or spiro bicyclic ring system consisting of 1 N atom and 5 to 6 C atoms as ring members,
wherein the ring system is attached via the N atom to the monocyclic heteroaromatic ring in formula (I) and
wherein the ring system is optionally substituted with one substituent selected from the group consisting of F, $CH_3$, $CF_3$, —CN, $CH_2$—OH and $CH_2$—$OCH_3$ and
wherein the ring system is optionally additionally substituted with one substituent selected from the group consisting of F and $CH_3$.

According to another embodiment, $R^2$ is selected from the group $R^2$-G3 consisting of
a fused bicyclic ring system consisting of 1 N atom and 5 C atoms as ring members and a spiro bicyclic ring system consisting of 1 N atom and 5 to 6 C atoms as ring members,
wherein the ring system is attached via the N atom to the monocyclic heteroaromatic ring in formula (I) and
wherein the ring system is optionally substituted with one substituent selected from the group consisting of F, $CH_3$,—CN and $CH_2$—OH and
wherein the ring system is optionally additionally substituted with one substituent selected from the group consisting of F and $CH_3$.

According to another embodiment, $R^2$ is selected from the group $R^2$-G4 consisting of

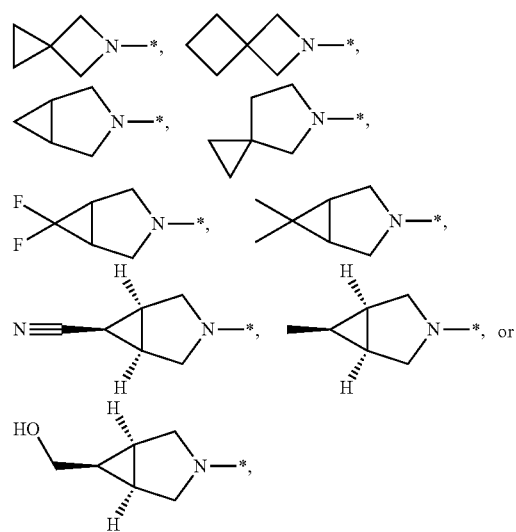

wherein, as indicated by the asterisk, the ring system is attached via the N atom to the monocyclic heteroaromatic ring in formula (I).

$R^3$:

According to one embodiment, $R^3$ is selected from the group $R^3$-G1 consisting of H, $CH_3$, $CHF_2$ and $CF_3$, According to another embodiment, $R^3$ is selected from the group $R^3$-G2 consisting of H and $CH_3$.

Further preferred subgeneric embodiments of the compounds of formula (I) are set forth as embodiments (I-a) to (I-g) in the following Table 1, wherein the above-mentioned substituent definitions are used. For example, the entry -G1 in column $R^1$ and row (I-a) means that in embodiment (I-a) substituent $R^1$ is selected from the definition designated $R^1$-G1. The same applies analogously to the other variables incorporated in the general formulas.

TABLE 1

| | Substituents | | | | |
|---|---|---|---|---|---|
| Embodiment | A | T | $R^1$ | $R^2$ | $R^3$ |
| (I-a) | A-G1 | T-G1 | $R^1$-G1 | $R^2$-G1 | $R^3$-G1 |
| (I-b) | A-G1 | T-G2 | $R^1$-G1 | $R^2$-G2 | $R^3$-G1 |
| (I-c) | A-G1 | T-G3 | $R^1$-G1 | $R^2$-G1 | $R^3$-G1 |
| (I-d) | A-G1 | T-G1 | $R^1$-G2 | $R^2$-G2 | $R^3$-G2 |
| (I-e) | A-G1 | T-G3 | $R^1$-G3 | $R^2$-G2 | $R^3$-G2 |
| (I-f) | A-G1 | T-G3 | $R^1$-G3 | $R^2$-G3 | $R^3$-G2 |
| (I-g) | A-G1 | T-G3 | $R^1$-G3 | $R^2$-G4 | $R^3$-G2 |

Particularly preferred compounds, including their tautomers, the salts thereof, or any solvates or hydrates thereof, are

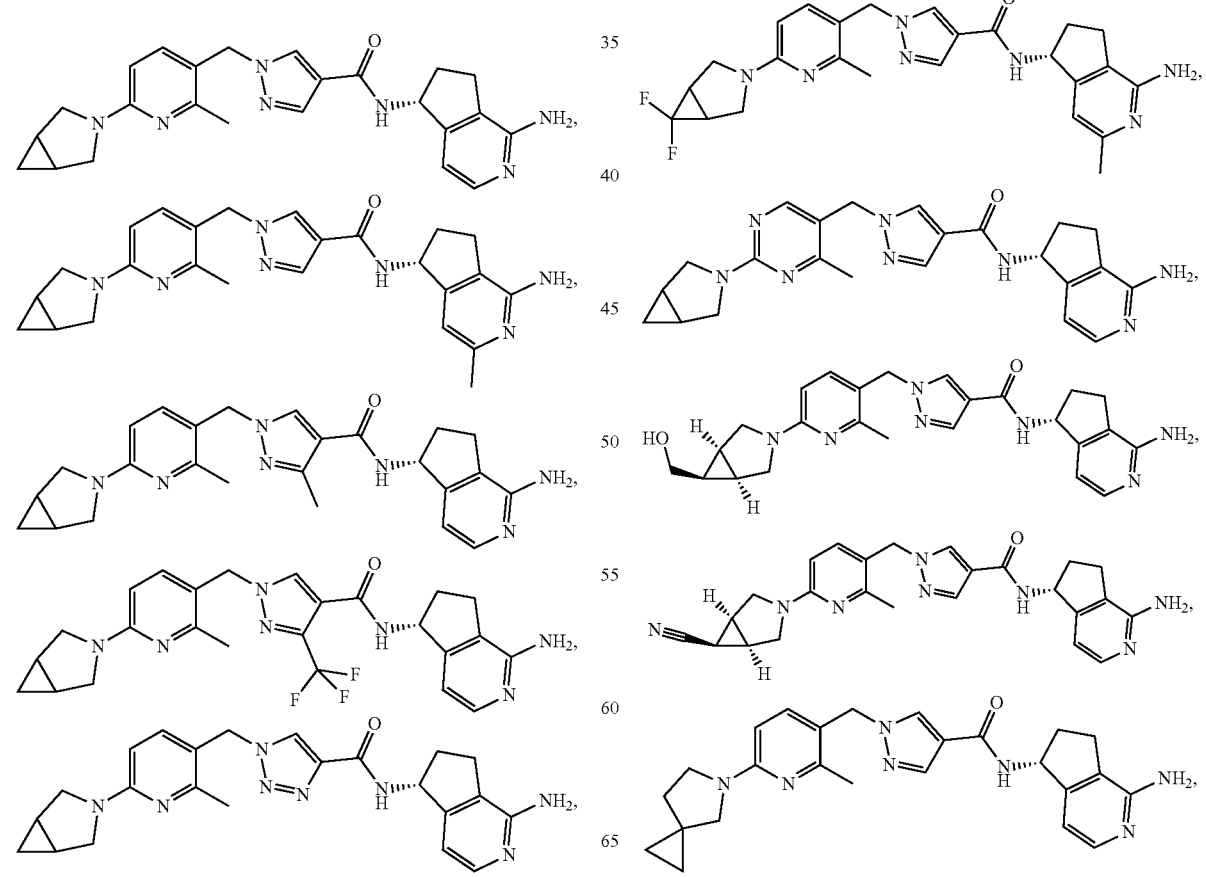

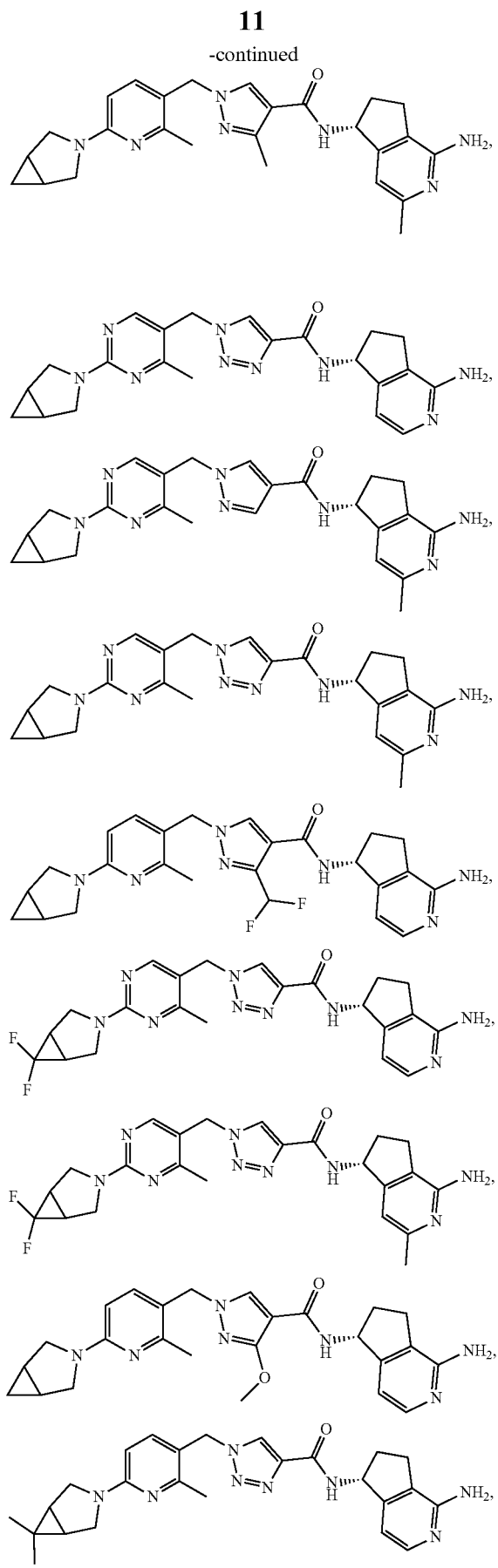

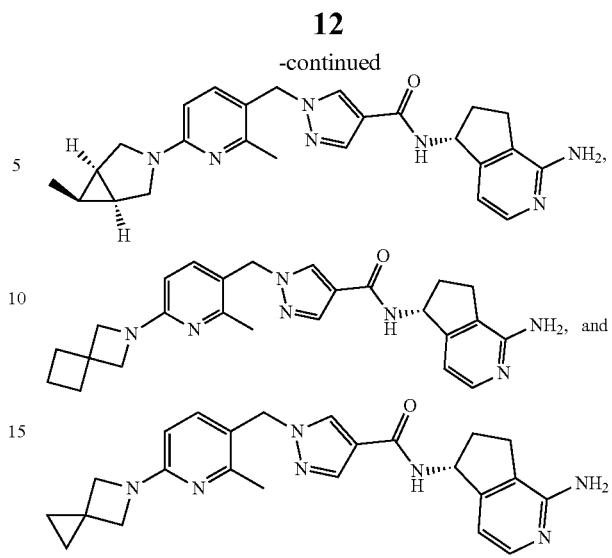

Preparation

The compounds according to the invention and their intermediates may be obtained using methods of synthesis which are known to the one skilled in the art and described in the literature of organic synthesis for example using methods described in "Comprehensive Organic Transformations", 2$^{nd}$ Edition, Richard C. Larock, John Wiley & Sons, 2010, and "March's Advanced Organic Chemistry", 7$^{th}$ Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled man and described in the literature for example in "Protecting Groups", 3$^{rd}$ Edition, Philip J. Kocienski, Thieme, 2005, and "Protective Groups in Organic Synthesis", 4th Edition, Peter G. M. Wuts, Theodora W. Greene, John Wiley & Sons, 2006.

Scheme 1:

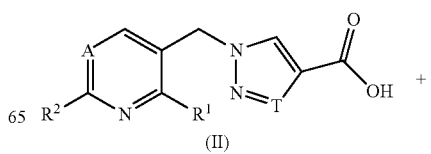

(II)

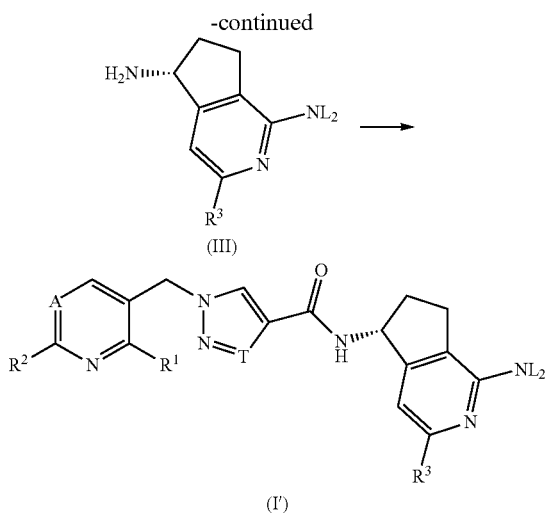

(I')

NL$_2$ = NH$_2$ or a protected or masked NH$_2$ group such as, e.g., NHCOO$^t$Bu, NHCH$_2$Ph, N(CH$_2$Ph)$_2$, wherein Ph (= phenyl) may be optionally substituted with 1 or 2 OCH$_3$ groups Scheme 1:

Compounds of formula (I) can be prepared by the reaction of a suitable acid of formula (II) (either as a free acid or as a salt with a suitable metal cation such as Li$^+$, Na$^+$, K$^+$ etc.) and a suitable amine of formula (III) (either as a free amine or as a salt such as a hydrochloride, hydrobromide etc.) in a suitable solvent (e.g. dichloromethane, tetrahydrofuran, 1,4-dioxane, N,N-dimethylformamide, N,N-dimethylacetamide, 1-methyl-2-pyrrolidinone etc.) in the presence of a suitable coupling agent (e.g. O-(7-azabenzotriazol-1-yl)-N, N, N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), carbodiimide reagents etc.) and a base (e.g. triethylamine, N,N-diisopropyl-ethylamine, pyridine etc.) to form an amide bond; A, T, R$^1$, R$^2$ and R$^3$ in scheme 1 have the meanings as defined hereinbefore. Alternatively, the carboxylic acid is transformed into a carboxylic chloride (using, e.g., oxalyl chloride or thionyl chloride in dichloromethane) and coupled as such with amine (III) in the presence of a suited base (e.g. triethylamine, N,N-diisopropyl-ethylamine, pyridine etc.). In case amine (III) is employed with a protected or masked amino group on the pyridine ring (NL$_2$ is not NH$_2$) this group can be transformed afterwards into the NH$_2$ group by cleaving off the protective group applying standard procedures reported in the literature of organic chemistry. A tert-butyl ester is preferably cleaved under acidic conditions with, e.g. trifluoroacetic acid or hydrochloric acid, in a solvent such as dichloromethane, 1,4-dioxane, isopropanol, or ethyl acetate. A benzyl group can be removed by using hydrogen in the presence of a transition metal such as palladium on carbon. Benzyl groups bearing electron donating groups such as methoxy on the aromatic ring may also be removed under oxidative conditions (e.g. with ceric ammonium nitrate (CAN) or 2,3-dichloro-5,6-dicyanoquinone (DDQ)) or acidic conditions (e.g. with trifluoroacetic acid or hydrochloric acid).

Scheme 2:

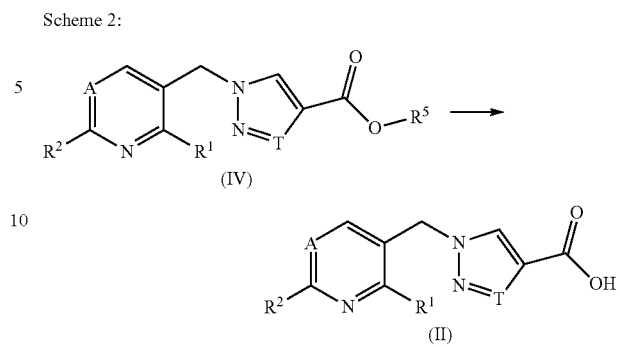

Scheme 2:

Acids of formula (II), wherein A, T, R$^1$ and R$^2$ have the meanings as defined hereinbefore, are preferably prepared from the corresponding ester (IV) through hydrolysis or hydrogenolysis depending on the nature of R$^5$. Lower alkyl group esters such as ethyl or methyl esters are preferably cleaved by hydrolysis with a hydroxide base such as NaOH, LiOH or KOH in a mixture of water and a suitable miscible solvent (e.g., tetrahydrofuran, methanol, ethanol, 1,4-dioxane etc. or mixtures of these), with heating if necessary. The acid may be isolated either as a salt with the metal cation or as a free acid. tert-Butyl ester is preferably cleaved by treatment with an acid (e.g. hydrochloric acid or trifluoroacetic acid) in a suitable solvent (e.g., dichloromethane, 1,4-dioxane, methanol, ethanol, tetrahydrofuran, water or mixtures of these). A benzyl ester is preferably cleaved by hydrogenolysis with a suitable catalyst (e.g., palladium on carbon etc.) in a suitable solvent (e.g. ethanol, methanol, tetrahydrofuran, dichloromethane, ethyl acetate etc.) under an atmosphere of hydrogen (preferably 1 to 5 bar).

Scheme 3

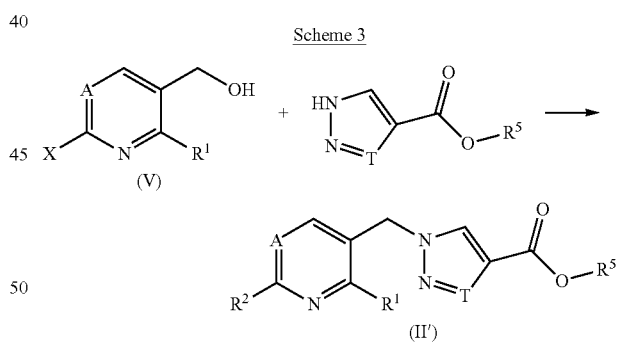

X = R$^2$, F, Cl, Br; R$^5$ = C$_{1-4}$-alkyl or benzyl

Scheme 3:

Some of the compounds (II) can be prepared by reaction of an alcohol (V) with an ester (VI) employing the conditions of the Mitsunobu reaction (e.g. triphenylphosphine or tri-n-butylphosphine plus diethyl azodicarboxylate (DEAD), diisopropyl azodicarboxylate (DIAD) or di-tert.-butyl azodicarboxylate (DBAD) etc. in a solvent such as tetrahydrofuran, 1,4-dioxane, toluene etc.); A, T, R$^1$ and R$^2$ in Scheme 3 have the meanings as defined hereinbefore. Alcohol (V) may bear the desired residue R$^2$ on the heteroaromatic ring or a leaving group instead to introduce R$^2$ later on.

Scheme 4

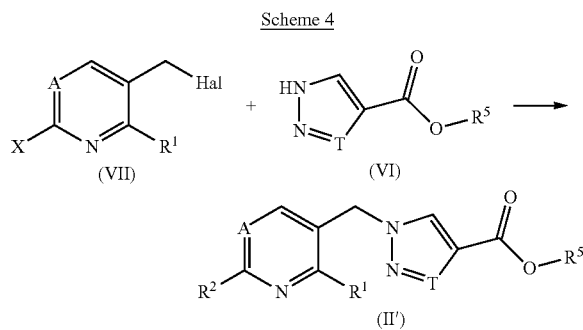

X = R², F, Cl, Br; R⁵ = C₁₋₄-alkyl or benzyl;
Hal = Cl, Br, I, OSO₂CH₃

Scheme 4:

Some of the compounds (II) can also be prepared by reaction of compound (VII), bearing a leaving group at the heteroarylmethyl position such as Cl, Br or mesyl, with pyrazole-4-carboxylic acid ester (VI) in the presence of a suitable base (e.g. sodium hydride, cesium carbonate, potassium carbonate etc.) in a suitable solvent (e.g. tetrahydrofuran, N,N-dimethylformamide etc.); A, T, R¹ and R² in Scheme 4 have the meanings as defined hereinbefore. Compound (VII) may bear the desired residue R² on the heteroaromatic ring or a leaving group instead to introduce R² later on.

Scheme 5

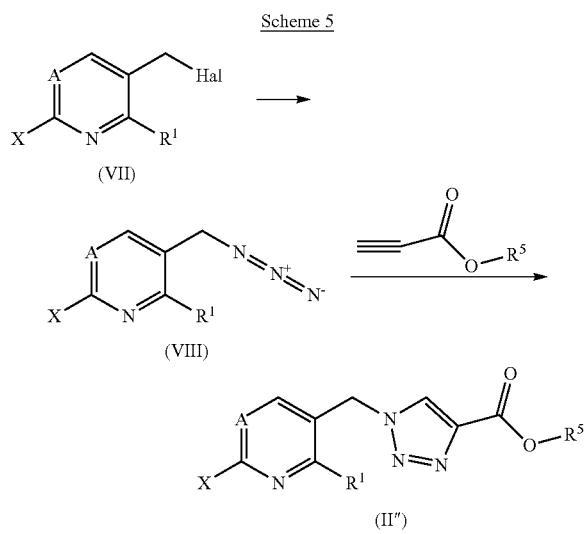

X = R², F, Cl, Br; R⁵ = C₁₋₄-alkyl or benzyl;
Hal = Cl, Br, I, OSO₂CH₃

Scheme 5:

Some esters of formula (II″), wherein A, R¹ and R² have the meanings defined hereinbefore, can be prepared by the treatment of a corresponding alkyl halide (bromide or chloride) or mesylate of formula (VII) with sodium azide in N,N-dimethylformamide or another suitable solvent to give an intermediate of formula (VIII) which is then reacted with a suitable propiolic acid ester under copper mediated catalytic conditions (e.g. ethyl propiolate or tert-butyl propiolate with catalytic copper sulfate and sodium ascorbate in water/tert-butanol) to give compound (II″).

Scheme 6

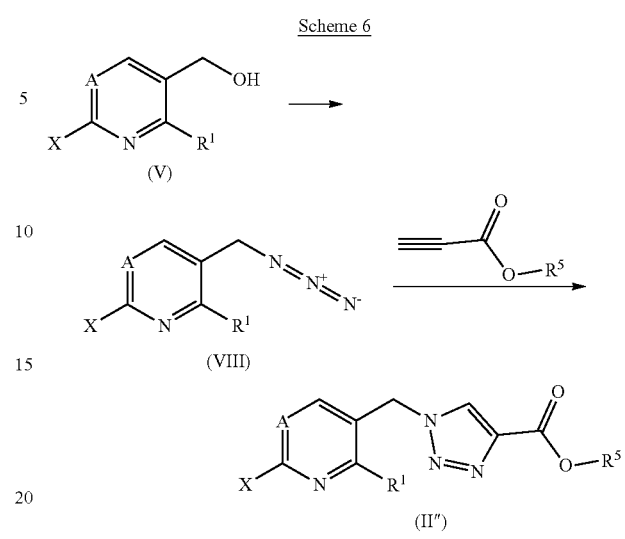

X = R², F, Cl, Br; R⁵ = C₁₋₄-alkyl or benzyl

Scheme 6:

Some esters of formula (II″), wherein A, R¹ and R² have the meanings defined hereinbefore, can also be obtained from an alcohol of formula (V) which is transformed into the corresponding azide (VIII) by the treatment with diphenylphosphoryl azide in the presence of a suitable base such as DBU in a suitable solvent (e.g. tetrahydrofuran or N,N-dimethylformamide). Compound (VIII) can then be further reacted as described in Scheme 5 to give compound (II″).

Scheme 7

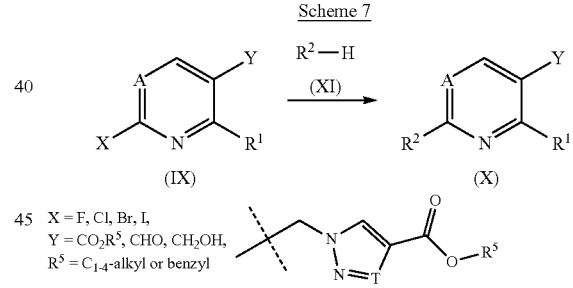

X = F, Cl, Br, I,
Y = CO₂R⁵, CHO, CH₂OH,
R⁵ = C₁₋₄-alkyl or benzyl

Scheme 7:

Intermediates of formula (X) can be prepared from heteroaromatic compound (IX) and amine (XI) via either a nucleophilic substitution reaction on the heteroaromatic ring or a transition metal catalyzed coupling reaction; A, T, R¹ and R² in Scheme 7 have the meanings defined hereinbefore. The nucleophilic substitution on the heteroaromatic ring in (IX) with the N in compound (XI) can be conducted in the presence of a suitable base (e.g. sodium hydride, cesium carbonate, potassium carbonate, N,N-diisopropyl-ethylamine etc.) in a suitable solvent (e.g. tetrahydrofuran, 1,4-dioxane, N,N-dimethylformamide etc.). A transition metal catalyzed coupling reaction is preferably carried out in analogy to procedures reported in the literature of organic chemistry referred to Ullmann or Buchwald/Hartwig coupling reaction using suitable palladium or copper salts or complexes, ligands, bases and solvents.

Scheme 8

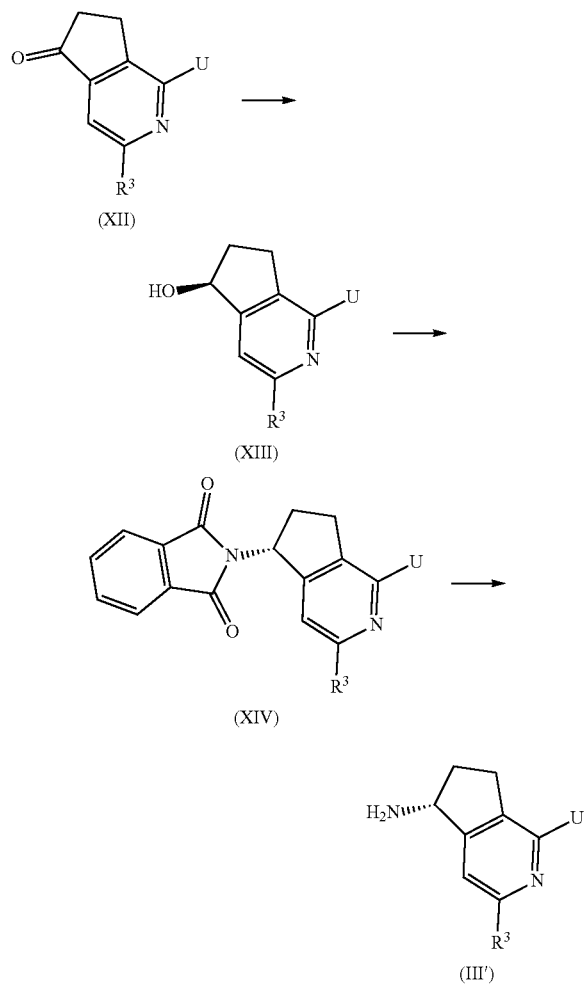

U = H, LG, protected or masked NH$_2$
LG = leaving group such as F, Cl, Br, I

Scheme 9

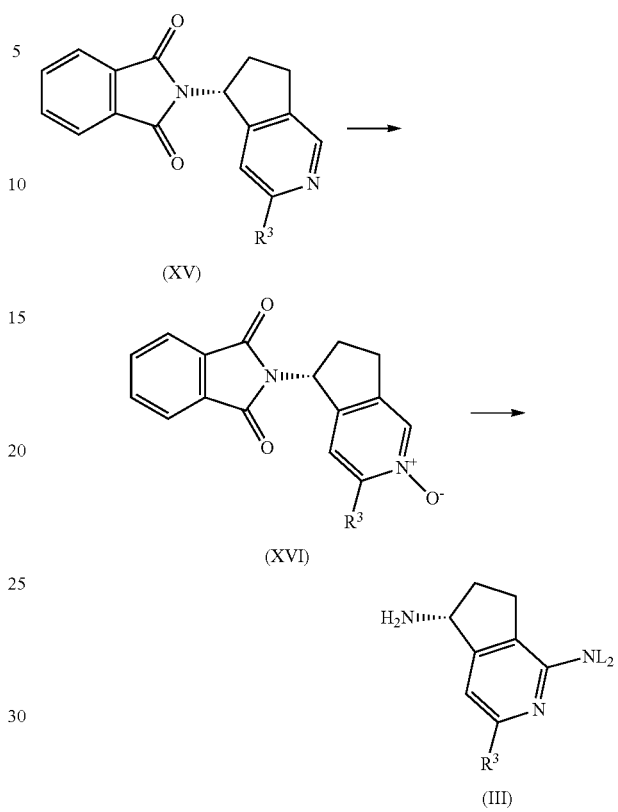

NL$_2$ = NH$_2$ or protected or masked NH$_2$ such as
NH—Bn or NH—DMB (DMB = 2,4-dimethoxybenzyl)

Scheme 8:

Enantiopure amines of formula (III') can be prepared as follows (R$^3$ in Scheme 8 has the meanings defined hereinbefore): A ketone of formula (XII) can be enantioselectively reduced under conditions reported in the literature of organic chemistry (e.g. in J. Am. Chem. Soc. 1995, 117 (28), pp 7562-7563) to give an enantiopure or enantioenriched alcohol of formula (XIII). The alcohol can then be reacted with phthalimide in a Mitsunobu reaction with suitable reagents (e.g. triphenylphosphine or tri-n-butylphosphine plus diethyl azodicarboxylate (DEAD), diisopropyl azodicarboxylate (DIAD) or di-tert.-butyl azodicarboxylate (DBAD) etc. in a suitable solvent (e.g. tetrahydrofuran, 1,4-dioxane, toluene etc.) leading to the inversion of the configuration of the stereocenter and an intermediate of formula (XIV). The amino group can be liberated from the phthalimide group by treatment with e.g. hydrazine or ethanolamine in a suitable solvent (e.g. ethanol, methanol, tetrahydrofuran, water etc. or a mixture of these) with heating if necessary to give an intermediate of formula (III').

Scheme 9:

The NH$_2$ group or a protected or masked incarnation of it on the pyridine ring of compound (III) may be introduced from N-oxide (XVI) by reaction with an amine such as ammonia, benzylamine or 2,4-dimethoxybenzylamine, in the presence of PyBroP (bromotrispyrrolidinophosphonium hexafluorophosphate) and a base (e.g. N,N-diisopropyl-ethylamine) in a suitable solvent (e.g. dichloromethane); R$^3$ in Scheme 9 has the meanings defined hereinbefore. N-oxide (XVI), in turn, can be obtained from compound (XV) with a suitable oxidizing agent (e.g. 3-chloroperbenzoic acid, oxone, hydrogen peroxide etc.) in an inert solvent (e.g. dichloromethane) following a routine process.

Scheme 10

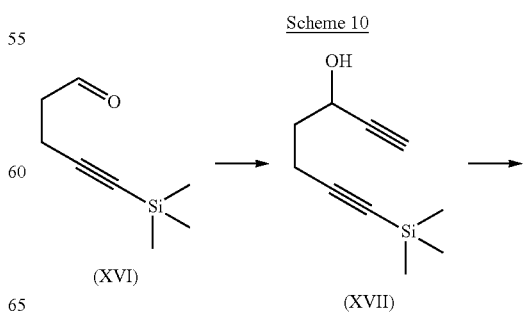

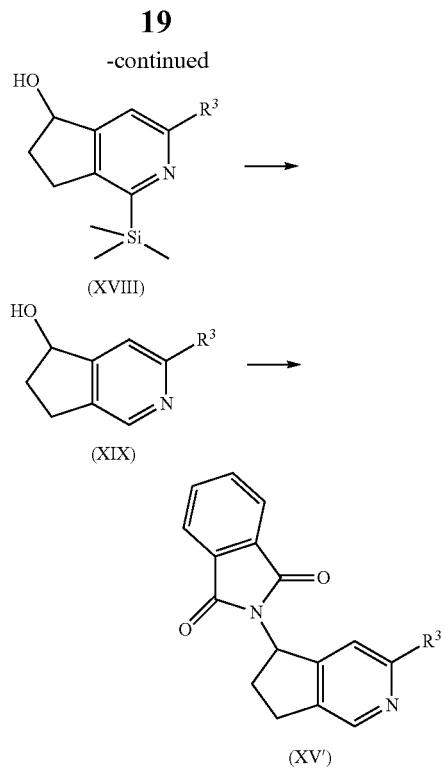

Scheme 10:

Compounds (XV') can be obtained from reported compound (XVI) in a sequence consisting of 4 reaction steps; $R^3$ in Scheme 10 has the meanings defined hereinbefore. Compound (XVI) can be transformed into compound (XVII) by adding a metal acetylide to the aldehyde group in (XVI). Ethynyl lithium or magnesium halide (chloride, bromide or iodide) are preferably employed as the acetylide nucleophile in an inert solvent (e.g. tetrahydrofuran, diethyl ether etc.) at low temperature (−78° C. to 20° C.). Compound (XVII) can then be reacted with a nitrile, e.g., acetonitrile, in the presence of a transition metal catalyst (e.g. cyclopentadienylcobalt dicarbonyl) in a suited solvent (e.g. toluene at elevated temperature, 60 to 140° C.) to give compound (XVIII). Compound (XVIII) can be desilylated, e.g., with a fluoride source (e.g. tetra-n-butylammonium fluoride) in a suited solvent (e.g. tetrahydrofuran) at ambient temperature or under acidic conditions (e.g. hydrochloric acid in 1,4-dioxane at elevated temperature). Compound (XV') can then be prepared by employing the proceeding described in Scheme 8.

The compounds of formula (I) may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of formula (I) which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physicochemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula (I) may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Pharmacological Activity

The activity of the compounds of the invention may be demonstrated using the following assay:

Biological Methods

The ability of compounds of formula (I) to inhibit plasma kallikrein (KLKB1), Factor XIIa (FXIIa), Factor XIa (FXIa), Factor Xa (FXa), Factor IIa (alpha-thrombin; FIIa), plasmin, trypsin, tissue kallikrein 1 (KLK1), Factor VIIa (FVIIa), or FVIIa complexed with Tissue Factor, phospholipids and $CaCl_2$ (FVIIa/TF/PL/$CaCl_2$) was determined using the following biochemical assays in assay buffer (100 mM Tris, 150 mM NaCL, adjusted to a pH of 7.8 with HCl, and containing 0.1% (w/v) BSA and 0.05% (v/v) Tween20) in the presence of 1% (v/v) DMSO:

Evaluation of the Inhibition of KLKB1 Using an Endpoint Assay

Human KLKB1 (0.01 U/mL; Enzyme Research Laboratories) or rat KLKB1 (0.625 nM; produced in-house) was incubated for 1 h at room temperature with 0.10 µM fluorogenic substrate H-Pro-Phe-Arg-AMC (11295 from Bachem) and various concentrations of the test compound in assay buffer. Subsequently, PPACK 11 (Calbiochem) was added as a stop solution to achieve a final concentration of 1 µM and fluorescence was measured using an Envision Reader (PerkinElmer) with the wavelength excitation setting of 355 nm and the wavelength emission setting of 460 nm.

$IC_{50}$ values for compounds according to the invention are shown in the following table. The number of the compound corresponds to the number of the Example in the experimental section.

| Example | $IC_{50}$ (nM) | Example | $IC_{50}$ (nM) | Example | $IC_{50}$ (nM) |
|---------|---------------|---------|---------------|---------|---------------|
| 1 | 0.5 | 2 | 0.3 | 3 | 0.7 |
| 4 | 0.8 | 5 | 0.8 | 6 | 1.0 |
| 7 | 1.1 | 8 | 5.5 | 9 | 0.6 |
| 10 | 0.4 | 11 | 1.7 | 12 | 1.9 |

-continued

| Example | IC$_{50}$ (nM) | Example | IC$_{50}$ (nM) | Example | IC$_{50}$ (nM) |
|---|---|---|---|---|---|
| 13 | 0.5 | 14 | 2.0 | 15 | 0.5 |
| 16 | 5.3 | 17 | 1.0 | 18 | 1.2 |
| 19 | 1.0 | 20 | 3.9 | 21 | 1.4 |
| 22 | 1.1 | 23 | 9.9 | 24 | 0.6 |
| 25 | 2.1 | 26 | 1.2 | | |

Evaluation of the Inhibition of Human KLKB1 in Dextran Sulfate Activated Human PPP Platelet poor plasma (PPP) obtained from human wholeblood, anticoagulated with EDTA, was activated with 12.5 µg/mL dextransulfate for 7 min on ice. The activated PPP was incubated with various concentrations of the test compound in assay buffer. Afterwards the mixture was incubated at 24° C. with 0.25 mM fluorogenic substrate H-Pro-Phe-Arg-AMC (11295 from Bachem) and measurements were performed in a kinetic interval every $2^{nd}$ minute for 16 min using a Spectramax M5 (Molecular Devices) with the following settings of the wavelength excitation of 350 nm and wavelength emission of 450 nm.

IC$_{50}$ values for compounds according to the invention are shown in the following table. The number of the compound corresponds to the number of the Example in the experimental section.

| Example | IC$_{50}$ (nM) | Example | IC$_{50}$ (nM) | Example | IC$_{50}$ (nM) |
|---|---|---|---|---|---|
| 1 | 54.1 | 5 | 61.2 | 9 | 18.1 |
| 11 | 50.3 | 12 | 46.7 | 13 | 32.3 |
| 14 | 80.3 | | | | |

Evaluation of the Inhibition of KLKB1 in Kaolin Activated Human PPP

Platelet poor plasma (PPP) obtained from human wholeblood, anticoagulated with Na-Citrat, was incubated with various concentrations of the test compound together with either 25, 75, 250, or 750 µg/mL kaolin in assay buffer for 20 min at 37° C. such that for each kaolin dose used a concentration response was obtained for the test compound. Afterwards 0.25 mM fluorogenic substrate H-Pro-Phe-Arg-AMC (11295 from Bachem) was added to the mixture and measurements were performed in a kinetic interval every 2nd minute for 12 min using a Spectramax M5 (Molecular Devices) with the following settings of the wavelength excitation of 350 nm and wavelength emission of 450 nm. pIC50 and pIC90 values were obtained from 4 x/y-plots (x=log M, Compound; y=delta rfu/min) fitted with GraphPad prism 7.0 (Equation: log(agonist) vs. response—Find ECanything; the four concentration response curves obtained for the test compound, each obtained using a different kaolin dose, were fitted using a global fitting procedure yielding shared pIC50 or pIC90 values).

IC$_{50}$ and IC$_{90}$ values for compounds according to the invention are shown in the following table. The number of the compound corresponds to the number of the Example in the experimental section.

| Example | IC$_{50}$ (nM) | IC$_{90}$ (nM) |
|---|---|---|
| 1 | 19 | 199 |
| 2 | 16.6 | 133.8 |
| 3 | 20.1 | 237.7 |
| 4 | 18 | 445.7 |
| 7 | 17.9 | 199.1 |
| 9 | 14 | 89.5 |
| 10 | 16.2 | 96.2 |
| 11 | 23.9 | 232.5 |
| 17 | 52.2 | 511.1 |

Evaluation of the Inhibition of KLKB1 ($K_i$)

Human KLKB1 (1.78 nM or 0.025 U/mL; Enzyme Research Laboratories) was incubated at 24° C. with 0.25 mM fluorogenic substrate H-Pro-Phe-Arg-AMC (11295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

$K_i$ values for compounds according to the invention are shown in the following table. The number of the compound corresponds to the number of the Example in the experimental section.

| Example | $K_i$ (nM) | Example | $K_i$ (nM) | Example | $K_i$ (nM) |
|---|---|---|---|---|---|
| 1 | 0.3 | 2 | 0.3 | 3 | 0.3 |
| 4 | 0.4 | 5 | 0.4 | 7 | 1.9 |
| 9 | 0.4 | 10 | 0.4 | 11 | 1.5 |
| 12 | 0.6 | 13 | 0.3 | 14 | 1.1 |
| 15 | 0.4 | 16 | 2.2 | 17 | 0.5 |
| 18 | 0.5 | | | | |

Evaluation of the Inhibition of FXIIa ($K_i$)

Human FXIIa (47.5 nM or 1.1 U/mL; Enzyme Research Laboratories) was incubated at 24° C. with 0.5 mM chromogenic Substrate S2302 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FXIa ($K_i$)

Human FXIa (0.5 nM or 0.016 U/mL; Enzyme Research Laboratories) was incubated at 24° C. with 0.25 mM fluorogenic substrate Boc-Glu(OBzl)-Ala-Arg-AMC.HCl (11575 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXa ($K_i$)

Human FXa (0.86 nM or 0.01 U/mL; Enzyme Research Laboratories) was incubated at 24° C. with 0.5 mM chromogenic Substrate S2765 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FIIa ($K_i$)

Human FIIa (44.6 nM or 5 U/mL; Enzyme Research Laboratories) was incubated at 24° C. with 0.5 mM chromogenic Substrate S2238 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Plasmin ($K_i$)

Human plasmin (64.1 nM or 0.0275 U/mL; Enzyme Research Laboratories) was incubated at 24° C. with 0.3 mM chromogenic Substrate S2251 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Trypsin ($K_i$)

Human trypsin (4.54 nM or 250 U/mL; Calbiochem) was incubated at 24° C. with 0.5 mM chromogenic Substrate S2222 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of KLK1 ($K_i$)

Prior to the assay, human KLK1 (R&D Systems) was activated by incubation with human trypsin (Calbiochem) in a 1:10,000 ratio for 15 min at 37° C. For assaying KLK1 inhibitory activity, activated KLK1 (31.25 nM or 1 U/mL) was incubated at 24° C. with 0.1 mM fluorogenic substrate H-Pro-Phe-Arg-AMC (11295 from Bachem) and various concentrations of the test compound in assay buffer. Measurements were performed in a kinetic interval every 2nd minute for 16 min using a Spectramax M5 (Molecular Devices) with the following settings of the wavelength excitation of 350 nm and wavelength emission of 450 nm.

Evaluation of the Inhibition of FVIIa ($K_i$)

Human FVIIa (0.86 nM or 0.01 U/mL; Enzyme Research Laboratories) was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FVIIa/TF/PL/CaCl$_2$ ($K_i$)

Human FVIIa (300 nM or 585 U/mL; Enzyme Research Laboratories) together with 10 mM CaCl$_2$*2H$_2$O and 13.3% (v/v) Dade®Innovin® (Siemens; OQUMI94E0002(5534), which contains recombinant human tissue factor synthetic phospholipids (thromboplastin), was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Calculation of pIC$_{50}$ and Pk$_i$ Values

The average $V_{max}$ values for the time interval from 2 to 12 min after initiation of the assay (expressed as either delta OD/min for assays using a chromogenic substrate or delta RFU/min for assays using a fluorigenic substrate, respectively) were plotted versus the Log of the concentration in molar of the evaluated inhibitor compound. The pIC$_{50}$ values were then fitted using a four-parametric fitting procedure using GraphPad Prism (version 6; GraphPad Software, Inc.). Respective $K_i$ values were obtained by correction of the IC$_{50}$ values for the respective $K_M$ value of the used substrate (see Table A for the obtained $K_M$ values of the used substrates) using the following formula:

$$K_i = \frac{IC_{50}}{1 + \frac{[\text{Substrate}, mM]}{K_M}}$$

Where the IC$_{50}$ is in molar and the $K_M$ value in mM.

TABLE A $K_M$ values obtained for the substrates used in the enzymatic assays.

| Enzyme | Substrate | $K_M$ (mM) |
|---|---|---|
| KLKB1 | I1295 | 0.16 |
| FXIIa | S2302 | 0.20 |
| FXIa | I1575 | 0.29 |
| FXa | S2765 | 1.31 |
| FIIa | S2238 | 1.25 |
| Plasmin | S2251 | 1.45 |
| Trypsin | S2222 | 2.03 |
| KLK1 | I1295 | 0.07 |
| FVIIa | Pefachrome ® FVIIa | 0.42 |
| FVIIa/TF/PL/CaCl$_2$ | Pefachrome ® FVIIa | 3.92 |

Evaluation of Permeability

Caco-2 cells (1-2×10$^5$ cells/1 cm$^2$ area) are seeded on filter inserts (Costar transwell polycarbonate or PET filters, 0.4 μm pore size) and cultured (DMEM) for 10 to 25 days.

Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$×7H$_2$O, 0.41 mM NaH$_2$PO$_4$×H$_2$O, 15 mM HEPES, 20 mM glucose, pH 7.2) to prepare the transport solutions (0.1-300 μM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human or rat liver microsomes. The final incubation volume of 100 μl per time point contains TRIS buffer pH 7.6 at RT (0.1 M), magnesium chloride (5 mM), microsomal protein (1 mg/mL) and the test compound at a final concentration of 1 μM.

Following a short preincubation period at 37° C., the reactions were initiated by addition of beta-nicotinamide adenine dinucleotide phosphate, reduced form (NADPH, 1 mM) and terminated by transferring an aliquot into solvent after different time points. Additionally, the NADPH-independent degradation was monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t1/2 INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. Hepatocytes (typically cryopreserved) are incubated in an appropriate buffer system (e.g. Dulbecco's modified eagle medium plus 3.5 μg glucagon/500 mL, 2.5 mg insulin/500 mL and 3.75 mg/500 mL hydrocortison) containing 5% species serum.

Following a (typically) 30 min preincubation in an incubator (37° C., 10% CO2) 5 µl of test compound solution (80 µM; from 2 mM in DMSO stock solution diluted 1:25 with medium) are added into 395 µl hepatocyte suspension (cell density in the range 0.25-5 Mio cells/mL, typically 1 Mio cells/mL; final concentration of test compound 1 µM, final DMSO concentration 0.05%).

The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended.

Decline of parent compound is analyzed by HPLC-MS/MS CLint is calculated as follows CL_INTRINSIC=Dose/AUC=(C0/CD)/(AUD+clast/k)×1000/60. C0: initial concentration in the incubation [µM], CD: cell density of vital cells [10e6 cells/mL], AUD: area under the data [µM×h], clast: concentration of last data point [µM], k: slope of the regression line for parent decline [h−1].

Evaluation of Plasma Protein Binding

This equilibrium dialysis (ED) technique is used to determine the approximate in vitro fractional binding of test compounds to plasma proteins. Dianorm Teflon dialysis cells (micro 0.2) are used. Each cell consists of a donor and an acceptor chamber, separated by an ultrathin semipermeable membrane with a 5 kDa molecular weight cutoff. Stock solutions for each test compound are prepared in DMSO at 1 mM and diluted to a final concentration of 1.0 µM. The subsequent dialysis solutions are prepared in pooled human or rat plasma (with NaEDTA) from male and female donors. Aliquots of 200 µL dialysis buffer (100 mM potassium phosphate, pH 7.4) are dispensed into the buffer chamber. Aliquots of 200 µL test compound dialysis solution are dispensed into the plasma chambers. Incubation is carried out for 2 hours under rotation at 37° C.

At the end of the dialysis period, the dialysate is transferred into reaction tubes. The tubes for the buffer fraction contain 0.2 mL Acetonitril/water (80/20). Aliquots of 25 µL of the plasma dialysate are transferred into deep well plates and mixed with 25 µl Acetonitril/water (80/20), 25 µl buffer, 25 µL calibration solution and 25 µl Internal Standard solution. Protein prezipitation is done by adding 200 µl Acetonitrile.

Aliquots of 50 µl of the buffer dialysate are transferred into deep well plates and mixed with 25 µl blank plasma, 25 µl Internal Standard solution and 200 µl Acetonitrile.

Samples are measured on HPLC-MS/MS-Systems and evaluated with Analyst-Software.

Percent bound is calculated with the formula:% bound=(plasma concentration−buffer concentration/plasma concentration)×100

Evaluation of Solubility

The aqueous solubility of the test compound is determined by comparing the amount dissolved in buffer to the amount in an acetonitrile/water (1/1) solution. Starting from a 10 mM DMSO stock solution aliquots are diluted with acetonitril/water (1/1) or buffer resp. After 24 h of shaking, the solutions are filtrated and analyzed by LC-UV. The amount dissolved in buffer is compared to the amount in the acetonitrile solution.

Solubility will usually be measured from 0.001 to 0.125 mg/mL at a DMSO concentration of 2.5%. If more than 90% of the compound is dissolved in buffer, the value is marked with ">".

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentration of analytes—the administered compound and/or metabolites—are quantified in the plasma samples.

PK parameters are calculated using non compartment methods. AUC and Cmax are normalized to a dose of 1 µmol/kg.

Methods of Treatment

In another aspect of the present invention, it is found that compounds of formula (I) or pharmaceutically acceptable salts thereof may be useful for the treatment of diseases or conditions mediated by unwanted plasma kallikrein activity in a mammal.

Diseases and conditions mediated by unwanted plasma kallikrein activity embrace diabetic complications, diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retinal vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), hereditary angioedema and acute respiratory distress syndrome (ARDS).

Thus, the compounds and pharmaceutical compositions of the present invention are particularly suitable for treating ocular diseases including diabetic retinopathy, proliferative and non-proliferative retinopathy, diabetic macular edema (DME), retinal vein occlusion, age-related macular degeneration (AMD), polypoidal choroidal vasculopathy (PCV) as well as hereditary angioedema.

In particular, the compounds and pharmaceutical compositions according to the invention are suitable for the treatment of diabetic retinopathy, proliferative and non-proliferative retinopathy, diabetic macular edema (DME), age-related macular degeneration (AMD) and polypoidal choroidal vasculopathy (PCV).

The compounds according to the invention are most particularly suitable for treating diabetic retinopathy, proliferative and non-proliferative retinopathy and diabetic macular edema (DME).

In addition, the compounds and pharmaceutical compositions according to the invention are suitable for use in one or more of the following therapeutic processes: Treatment of edema, particularly hereditary angioedema.

The dose range of the compounds of formula (I) applicable per day is usually from 0.01 to 10 mg per kg body weight.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, intravitreal, transdermal, inhalative, parenteral or sublingual route.

Of the possible methods of administration, oral or intravitreal administration is preferred. In case of intravitreal injection the preferred dose should not exceed 5 mg per eye.

Thus, in a further aspect the invention provides new compounds of formula (I), including pharmaceutically acceptable salts thereof, which inhibit plasma kallikrein and possess suitable pharmacological and pharmacokinetic properties for use in therapy, i.e. for use as medicaments.

In a further aspect the invention provides new compounds of formula (I), including pharmaceutically acceptable salts thereof, for use in a method for the treatment of a disease or condition which can be influenced in a beneficial way by inhibition of plasma kallikrein.

In a further aspect the invention provides new compounds of formula (I), or pharmaceutically acceptable salts thereof, for the treatment of ophthalmic indications such as diabetic retinopathy, proliferative and non-proliferative retinopathy, diabetic macular edema (DME), age-related macular degeneration (AMD) and polypoidal choroidal vasculopathy (PCV).

In another aspect, the present invention provides the use of a compound of formula (I), or pharmaceutically acceptable salts thereof, in the manufacture of a medicament for use in the treatment of a disease or condition in which inhibition of plasma kallikrein is beneficial.

In a further aspect, the present invention provides the use of a compound of formula (I), or pharmaceutically acceptable salts thereof, in the manufacture of a medicament for use in the treatment of ophthalmic indications such as diabetic retinopathy, proliferative and non-proliferative retinopathy, diabetic macular edema (DME), age-related macular degeneration (AMD) and polypoidal choroidal vasculopathy (PCV).

Accordingly, the present invention relates to compounds of formula (I) as a medicament.

Furthermore, the present invention relates to the use of a compound of formula (I) in a method for the treatment of diseases or conditions which are mediated by unwanted plasma kallikrein activity in a patient, preferably in a human.

Furthermore, the present invention relates to the use of a compound of formula (I) in a method for the treatment of ophthalmic indications such as diabetic retinopathy, proliferative and non-proliferative retinopathy, diabetic macular edema (DME), age-related macular degeneration (AMD) and polypoidal choroidal vasculopathy (PCV).

In yet another aspect the present invention relates to a method for the treatment of a disease or condition which can be influenced by the inhibition of plasma kallikrein in a mammal that includes the step of administering to a patient, preferably a human, in need of such treatment a therapeutically effective amount of a compound or a pharmaceutical composition of the present invention.

In a further aspect the invention provides a method for the treatment of a disease or condition which can be influenced in a beneficial way by inhibition of plasma kallikrein, in a subject comprising administering a therapeutically effective amount of a compound of formula (I), or a pharmaceutically acceptable salt thereof, to a patient in need thereof.

In a further aspect the invention provides a method for the treatment of ophthalmic indications such as diabetic retinopathy, proliferative and non-proliferative retinopathy, diabetic macular edema (DME), age-related macular degeneration (AMD) and polypoidal choroidal vasculopathy (PCV) in a patient, comprising administering a therapeutically effective amount of a compound of formula (I), or a pharmaceutically acceptable salt, thereof to a patient in need thereof.

According to another aspect of the invention, there is provided a method for the treatment of diabetic complications, particularly of retinal vascular permeability associated with diabetic retinopathy and diabetic macular edema, in a patient in need thereof characterized in that a therapeutically effective amount of a compound of formula (I) or a pharmaceutically acceptable salt thereof is administered to the patient.

Pharmaceutical Compositions

In another aspect of the present invention, it is described that a compound of the invention or a pharmaceutically acceptable salt thereof may be used as active ingredients in pharmaceutical compositions.

Suitable preparations for administering the compounds of the invention, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants.

The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula (I) according to the invention, or a pharmaceutically acceptable salt of such a compound, and one or more excipients, carriers and/or diluents.

Thus, according to another aspect of the present invention, pharmaceutical compositions comprising one or more compounds of formula (I), or pharmaceutically acceptable salts thereof, optionally together with one or more inert carriers and/or diluents are provided.

Also, a pharmaceutical composition is provided that comprises one or more of the above-mentioned compounds, or pharmaceutically acceptable salts thereof, optionally together with one or more inert carriers and/or diluents for use in a method for the treatment of diseases or conditions which can be influenced by the inhibition of plasma kallikrein.

In particular, the invention provides a pharmaceutical composition according to the invention for use in a method of treatment of ophthalmic indications such as diabetic retinopathy, proliferative and non-proliferative retinopathy, diabetic macular edema (DME), age-related macular degeneration (AMD) and polypoidal choroidal vasculopathy (PCV).

Furthermore, the present invention relates to the use of a pharmaceutical composition according to this invention for the treatment of diseases or conditions which are mediated by unwanted plasma kallikrein activity in a patient, preferably in a human.

Also, the present invention relates to the use of a pharmaceutical composition according to this invention for the treatment of diseases or conditions which can be influenced by the inhibition of plasma kallikrein in a patient, preferably in a human.

According to another embodiment, a pharmaceutical composition comprising one or more compounds of formula (I), or pharmaceutically acceptable salts thereof, and one or more additional therapeutic agents, optionally together with one or more inert carriers and/or diluents is provided. Preferably, this composition comprises one compound of formula (I) or a pharmaceutically acceptable salt thereof and one or more additional therapeutic agents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia, or therapeutic agents useful for the treatment of ocular diseases. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis and agents for the treatment of ocular diseases. Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid) receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, ß-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3) inhibitors, Complement inhibitors (e.g. Complement factors 3, 5, B, and D inhibitors), Bradykinin receptor 1 antagonists, CCR-2 antagonists.

Additional treatments for ocular diseases may include laser coagulation therapy.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by unwanted plasma kallikrein activity, in particular diseases or conditions as described hereinbefore and hereinafter.

In a further aspect this invention relates to a method for treating a disease or condition which can be influenced by the inhibition of plasma kallikrein in a patient that includes the step of administering to the patient in need of such treatment a therapeutically effective amount of a compound of formula (I) or a pharmaceutically acceptable salt thereof in combination with a therapeutically effective amount of one or more additional therapeutic agents.

In a further aspect this invention relates to the use of a compound of formula (I) or a pharmaceutically acceptable salt thereof in combination with one or more additional therapeutic agents for the treatment of diseases or conditions which can be influenced by the inhibition of plasma kallikrein in a patient in need thereof.

In yet another aspect the present invention relates a method for the treatment of a disease or condition mediated by unwanted plasma kallikrein activity in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Examples and Experimental Data

The following examples are for the purpose of illustration of the invention only and are not intended in any way to limit the scope of the present invention.

Abbreviations

Ac acetyl
ACN acetonitrile
APCI atmospheric pressure chemical ionization
Boc tert-butyloxycarbonyl
CDI 1,1'-carbonyldiimidazole
d day
dba dibenzylideneacetone
DCM dichloromethane
DIPEA N,N-diisopropylethylamine
DME 1,2-dimethoxyethane
DMF N,N-dimethylformamide
DMSO dimethyl sulfoxide
dppf 1,1'-Bis(diphenylphosphino)ferrocene
ESI electrospray ionization (in MS)
EtOAc ethylacetate
EtOH ethanol
Ex. example
h hour(s)
HATU O-(7-azabenzotriazol-1-yl)-N, N,N',N'-tetramethyl-uronium-hexafluorophosphate
HPLC high performance liquid chromatography
HPLC-MS coupled high performance liquid chromatography-mass spectrometry
LC liquid chromatography
LC-MS coupled liquid chromatography—mass spectrometry
M molar (mol/L)
MeOH methanol
min minute(s)
MS mass spectrometry
NMP 1-methyl-2-pyrrolidinone
PyBop (benzotriazol-1-yloxy)tripyrrolidinophosphonium hexafluorophosphate
PyBrop bromotripyrrolidinophosphonium hexafluorophosphate
RP reverse phase
rt room temperature
$t_R$ retention time (in HPLC/LC)
SFC supercritical fluid chromatography
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra-performance liquid chromatography—mass spectrometry General Technical Remarks The terms "ambient temperature" and "room temperature" are used interchangeably and designate a temperature of about 20° C., e.g. 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of a chiral starting material of known stereochemistry, by stereoselective synthesis of known stereochemistry or by biological activity.

A) Analytical Methods

UPLC-MS and HPLC-MS Methods:

Method 1

Instrument: LC/MS Waters Acquity UPLC System DAD, SQD single quadrupole
Column: BEH C18 1.7 μm 2.1×50 mm, Temp 35° C.
Mobile phase: A=H$_2$O 90%+CH$_3$CN 10%+NH$_4$COOH 5 mM
B=CH$_3$CN 90%+H$_2$O 10%

| Time in min | % A | % B | flow rate in mL/min |
| --- | --- | --- | --- |
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ESI$^+$/ESI$^-$
Scan range: 90-900 amu Method 2

Instrument: LC/MS ThermoFinnigan HPLC Surveyor DAD, MSQ single quadrupole
Column: Synergi Hydro RP100A, 2.5 μm, 3×50 mm
Mobile phase: A=H$_2$O 90%+10% CH$_3$CN+NH$_4$COOH 10 mM
B=CH$_3$CN 90%+H$_2$O 10%+NH$_4$COOH 10 mM

| Time in min: | % A | % B | Flow rate in mL/min |
| --- | --- | --- | --- |
| 0.00 | 100 | 0 | 1.2 |
| 0.50 | 100 | 0 | 1.2 |
| 6.50 | 0 | 100 | 1.2 |
| 7.50 | 0 | 100 | 1.2 |
| 8.00 | 100 | 0 | 1.2 |
| 9.00 | 100 | 0 | 1.2 |

Detection: UV 254 nm
Detection: Finnigan MSQ, single quadrupole
Ion source: APCI$^+$/APCI$^-$
Scan range: 100-900 amu Method 3

Instrument: LC/MS Waters Acquity UPLC System DAD, SQD single quadrupole
Column: BEH C18 1.7 μm 2.1×50 mm, Temp 35° C.
Mobile phase: A=H$_2$O 90%+CH$_3$CN 10%+NH$_4$HCO$_3$ 5 mM
B=CH$_3$CN 90%+H$_2$O 10%

| Time in min | % A | % B | flow rate in mL/min |
| --- | --- | --- | --- |
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

-continued

| Time in min | % A | % B | flow rate in mL/min |
|---|---|---|---|

Detection: UV 254 nm
Detection: SQD, single quadrupole
Ion source: ESI⁺/ESI⁻
Scan range: 90-900 amu
Method 4
Instrument: LC/MS Waters Alliance 2695 HPLC System DAD, Quattro Micro Triple quadrupole
Column: Atlantis dC18 5 µm 4.6×50 mm, Temp 35° C.
Mobile phase: A=$H_2O$ 90%+10% $CH_3CN$+$CF_3COOH$ 0.05%
B=$CH_3CN$ 90%+10% $H_2O$

| Time in min | % A | % B | flow rate in mL/min |
|---|---|---|---|
| 0.00 | 100 | 0 | 1.3 |
| 0.70 | 100 | 0 | 1.3 |
| 4.5 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ESI⁺
Scan range: 90-1000 amu
Method 5
Instrument: LC/MS Waters Alliance 2695 HPLC System DAD, Quattro Micro Triple quadrupole
Column: Zorbax Eclipse XDB-C18 3.5 µm 4.6×50 mm, Temp 35° C.
Mobile phase: A=$H_2O$ 90%+10% $CH_3CN$+$NH_4COOH$ 5 mM
B=$CH_3CN$ 90%+10% $H_2O$

| Time in min | % A | % B | flow rate in mL/min |
|---|---|---|---|
| 0.00 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ESI⁺/ESI⁻ Scan range: 90-1000 amu
Method 6
Instrument: LC/MS Waters Alliance 2695 HPLC System DAD, Quattro Micro Triple quadrupole
Column: XBridge BEH 300 C18 3.5 µm 4.6×100 mm, Temp 40° C.
Mobile phase: A=$H_2O$ 90%+10% $CH_3CN$+$NH_4COOH$ 5 mM
B=$CH_3CN$ 90%+10% $H_2O$

| Time in min | % A | % B | flow rate in mL/min |
|---|---|---|---|
| 0.00 | 100 | 0 | 1.3 |
| 12.00 | 50 | 50 | 1.3 |
| 18.00 | 0 | 100 | 1.3 |
| 20.00 | 0 | 100 | 1.3 |

Detection: UV 254 nm
Detection: Quattro Micro, triple quadrupole
Ion source: ESI⁺/ESI⁻
Scan range: 90-1000 amu

| Gradient/Solvent Time [min] | % Solvent [$H_2O$, 0.1% TFA] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Gradient/Solvent Time [min] | % Solvent [$H_2O$, 0.1% $NH_3$] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Gradient/Solvent Time [min] | % Solvent [$H_2O$, 0.1% TFA] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Gradient/Solvent Time [min] | % Solvent [$H_2O$, 0.1% TFA] | % Solvent [Acetonitrile 0.08% TFA] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

| Gradient/Solvent Time [min] | % Solvent [$H_2O$, 0.1% NH3] | % Solvent [Acetonitrile] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

| Gradient/Solvent Time [min] | % Solvent [$H_2O$, 0.1% $NH_3$] | % Solvent [Acetonitrile] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Gc-Ms Methods:
Method G1
Instrument: GC/MS Thermo Scientific TRACE GC ULTRA, DSQ II MS single quadrupole
Column: Agilent DB-5MS, 25 m×0.25 mm×0.25 um
Carrier gas: Helium, 1 mL/min constant flow
Oven Program: 50° C., to 100° C. in 10° C./min, to 200° C. in 20° C./min, to 320° C. in 30° C./min (hold 10 min).
Detection: DSQ II MS single quadrupole
Ion source: EI
Scan range: 50-450 amu
Microwave Heating:
Discover® CEM instruments, equipped with 10 and 35 mL vessels
NMR Equipment:
The 1H NMR spectra were recorded on a Bruker Avance III (500 MHz) or a Varian 400 (400 MHz) instrument using deuterated dimethylsulfoxide (DMSO-$d_6$) as the solvent with tetramethylsilane (TMS) or the residual solvent peak as an internal standard. Chemical shifts are reported in δ values (ppm) relative to TMS.

B) Syntheses of Intermediates

Intermediate 1

[6-(3-Aza-bicyclo[3.1.0]hex-3-yl)-2-methyl-pyridin-3-yl]-methanol

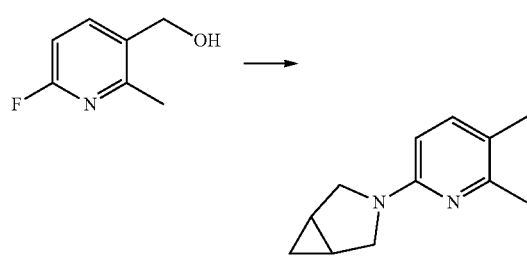

2-Fluoro-5-(hydroxymethyl)-6-picoline (1.0 g), 3-azabicyclo[3.1.0]hexane hydrochloride (1.27 g) and potassium carbonate (3.43 g) are suspended in NMP (10 mL) in a microwave vial and heated at 135° C. for 4 hours under microwave irradiation (raising the temperature from 80° C. to 135° C. in approx. 20° C. steps to avoid overheating). The mixture is cooled, diluted with ethyl acetate (200 mL and washed with saturated aqueous sodium chloride solution (5×40 mL). The organic phase is dried (Na$_2$SO$_4$) and evaporated and the residue is purified by flash chromatography (0-10% methanol in dichloromethane) to give the title compound.
LC (Method 3): $t_R$=0.91 min; Mass spectrum (ESI$^+$): m/z=205 [M+H]$^+$.

Intermediate 2

[6-(5-Aza-spiro[2.4]heptan-5-yl)-2-methyl-pyridin-3-yl]-methanol

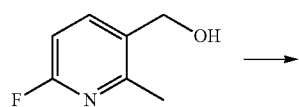

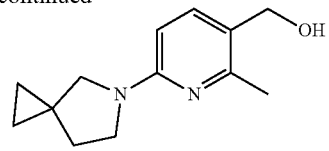

2-Fluoro-5-(hydroxymethyl)-6-picoline (0.5 g), 5-azaspiro[2.4]heptane hydrochloride (0.71 g) and potassium carbonate (1.72 g) are suspended in NMP (1 mL) in a microwave vial and heated at 160° C. for 5 hours under microwave irradiation (raising the temperature from 80° C. to 160° C. in approx. 20° C. steps to avoid overheating). The mixture is cooled, diluted with dichloromethane and water and washed with brine. The organic phase is dried and evaporated and the residue is purified by flash chromatography (0-100% ethyl acetate in cyclohexane) to give the title compound.
LC (Method 3): $t_R$=0.94 min; Mass spectrum (ESI$^+$): m/z=219 [M+H]$^+$.

Intermediate 3

[2-(3-Aza-bicyclo[3.1.0]hexan-3-yl)-4-methylpyrimidin-5-yl]methanol

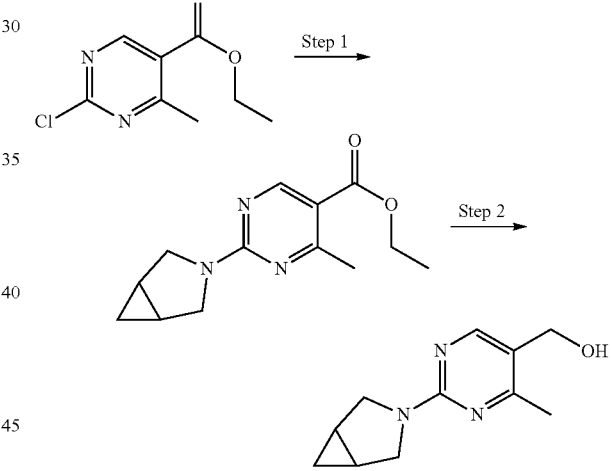

Step 1: Ethyl 2-{3-azabicyclo[3.1.0]hexan-3-yl}-4-methylpyrimidine-5-carboxylate Ethyl 2-chloro-4-methylpyrimidine-5-carboxylate (1.0 g), 3-azabicyclo[3.1.0]hexane hydrochloride (657 mg) and potassium carbonate (2.07 g) are suspended in dry NMP (20 mL) and stirred for 3 hours at 90° C. The mixture is cooled, diluted with dichloromethane and water and washed with brine. The organic phase is dried (Na$_2$SO$_4$) and evaporated and the residue is purified by flash chromatography (10% ethyl acetate in cyclohexane) to give the title compound.
LC (Method 3): $t_R$=1.28 min; Mass spectrum (ESI$^+$): m/z=248 [M+H]$^+$.

Step 2: (2-{3-Azabicyclo[3.1.0]hexan-3-yl}-4-methylpyrimidin-5-yl)methanol

Ethyl 2-{3-azabicyclo[3.1.0]hexan-3-yl}-4-methylpyrimidine-5-carboxylate (1.1 g) is suspended in dry THF (15 mL) and cooled to 0° C. a solution of lithium borohydride in THF (2M, 3.39 mL) is added and the mixture allowed to warm to room temperature. Methanol (270 µL) is added, the mixture heated to 60° C. and stirred for 3 hours. Water (2 mL) is added and the solvent evaporated, the residue is diluted with dichloromethane and water and washed with brine. The organic phase is dried (Na$_2$SO$_4$) and the residue is purified by flash chromatography (50-100% ethyl acetate in cyclohexane) to give the title compound.

LC (Method 3): $t_R$=0.74 min; Mass spectrum (ESI$^+$): m/z=206 [M+H]$^+$.

Intermediate 4

Ethyl 1-[(6-{3-azabicyclo[3.1.0]hexan-3-yl}-2-methylpyridin-3-yl)methyl]-1H-pyrazole-4-carboxylate

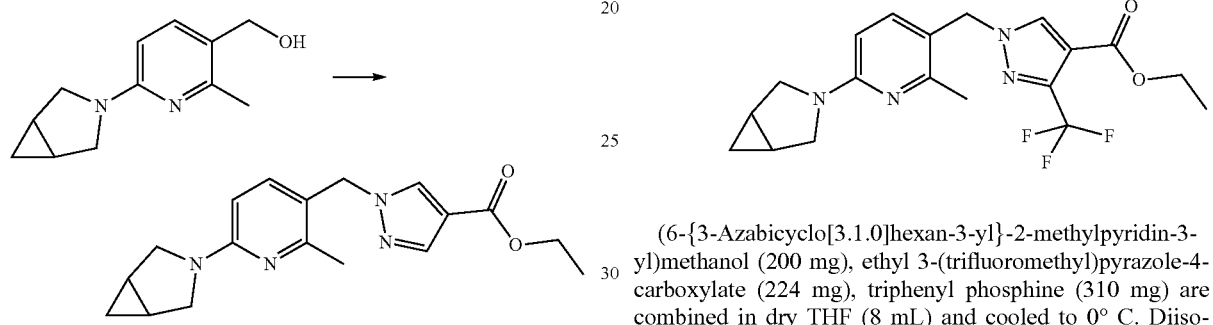

(6-{3-Azabicyclo[3.1.0]hexan-3-yl}-2-methylpyridin-3-yl)methanol (5.2 g), ethyl 1H-pyrazole-4-carboxylate (5.35 g), triphenyl phosphine (8.01 g) and diisopropylazodicarboxylate (DIAD, 6.02 mL) are combined in dry THF (60 mL) and stirred for 30 minutes at room temperature. The solvent is evaporated and the residue is purified by flash chromatography (0-70% ethyl acetate in cyclohexane) to give the title compound.

LC (Method 4): $t_R$=3.26 min; Mass spectrum (ESI$^+$): m/z=327 [M+H]$^+$.

Intermediate 5

Ethyl 1-[(6-{3-azabicyclo[3.1.0]hexan-3-yl}-2-methylpyridin-3-yl)methyl]-3-(trifluoromethyl)-1H-pyrazole-4-carboxylate

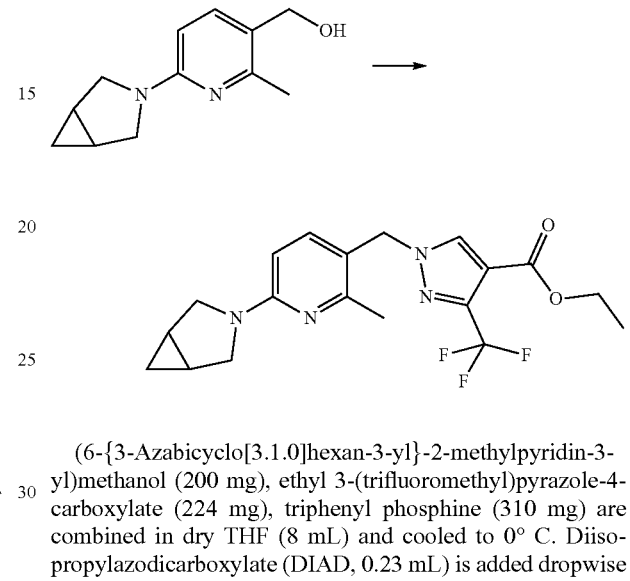

(6-{3-Azabicyclo[3.1.0]hexan-3-yl}-2-methylpyridin-3-yl)methanol (200 mg), ethyl 3-(trifluoromethyl)pyrazole-4-carboxylate (224 mg), triphenyl phosphine (310 mg) are combined in dry THF (8 mL) and cooled to 0° C. Diisopropylazodicarboxylate (DIAD, 0.23 mL) is added dropwise and the mixture allowed to warm to room temperature and stirred for one hour. The solvent is evaporated and the residue is purified by flash chromatography (0-70% ethyl acetate in cyclohexane) to give the title compound.

LC (Method 4): $t_R$=3.82 min; Mass spectrum (ESI$^+$): m/z=395 [M+H]$^+$.

The following intermediates are prepared in analogy to Intermediate 5, from the corresponding starting intermediates:

| Intermediate | Structure | Starting intermediates | Analysis |
|---|---|---|---|
| 6 | 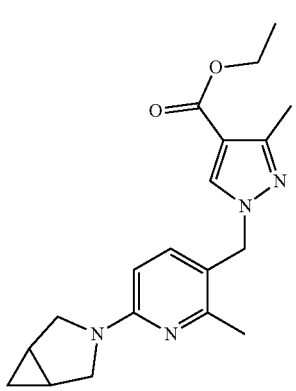 [SMILES: CCOC(=O)c1cn(Cc2ccc(N3CC4CC4C3)nc2C)nc1C] | Intermediate 1 and ethyl-3-methyl pyrazole-4-carboxylate (available from Apollo, CN OR300792) | LC (Method 1): $t_R$ = 1.29 min; Mass spectrum (ESI$^+$): m/z = 341 [M + H]$^+$ Contains an isomer as an impurity |

-continued

| Intermediate | Structure | Starting intermediates | Analysis |
|---|---|---|---|
| 7 | 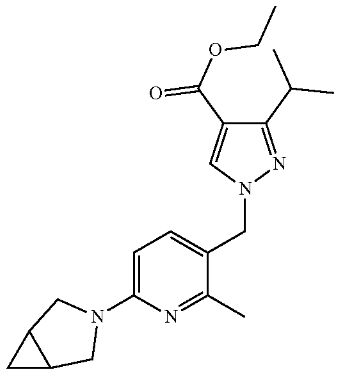 [SMILES: CCOC(=O)c1cn(Cc2ccc(N3CC4CC4C3)nc2C)nc1C(C)C] | Intermediate 1 and ethyl-3-isopropyl pyrazole-4-carboxylate (available from Combiblocks, CN QE-9605) | LC (Method 2): $t_R$ = 5.58, 5.75 min; Mass spectrum (ESI$^+$): m/z = 369 [M + H]$^+$ Contains an isomer as an impurity |
| 8 | 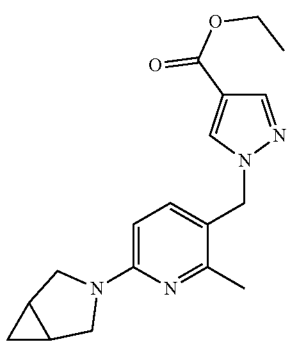 [SMILES: CCOC(=O)c1cnn(Cc2ccc(N3CC4CC4C3)nc2C)c1] | Intermediate 3 and ethyl 4-pyrazolecarboxylate, overnight reaction | LC (Method 3): $t_R$ = 1.08 min; Mass spectrum (ESI$^+$): m/z = 328 [M + H]* |
| 9 | 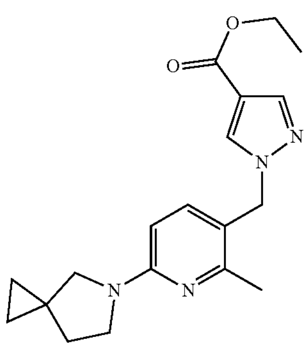 [SMILES: CCOC(=O)c1cnn(Cc2ccc(N3CCC4(CC4)C3)nc2C)c1] | Intermediate 2 and ethyl 4-pyrazolecarboxylate | LC (Method 4): $t_R$ = 3.35 min; Mass spectrum (ESI$^+$): m/z = 341 [M + H]* |
| 10 | 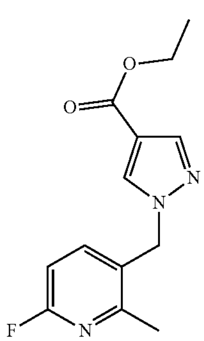 [SMILES: CCOC(=O)c1cnn(Cc2ccc(F)nc2C)c1] | 2-Fluoro-5-(hydroxymethyl)-6-picoline and ethyl 4-pyrazolecarboxylate, dry toluene as solvent, overnight reaction | LC (Method 2): $t_R$ = 3.37 min; Mass spectrum (ESI$^+$): m/z = 264 [M + H]* |

| Inter-mediate | Structure | Starting intermediates | Analysis |
|---|---|---|---|
| 11 | 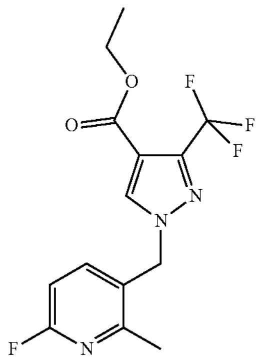 [SMILES: CCOC(=O)c1cn(Cc2ccc(F)nc2C)nc1C(F)(F)F] | 2-Fluoro-5-(hydroxymethyl)-6-picoline and ethyl 3-(trifluoromethyl)-propylpyrazole-4-carboxylate, 3 h reaction | GC (Method G1): $t_R$ = 11.71 min; Mass spectrum (EI$^+$): m/z = 331 [M]$^+$ |

Intermediate 12

Ethyl 1-[(6-{6,6-difluoro-3-azabicyclo[3.1.0]hexan-3-yl}-2-methylpyridin-3-yl)methyl]-1H-pyrazole-4-carboxylate 1-[(6-Fluoro-2-methylpyridin-3-yl)methyl]-1H-pyrazole-4-carboxylic acid ethyl ester (Intermediate 10, 300 mg), 6,6-difluoro-3-aza-bicyclo[3.1.0]hexane hydrochloride (213 mg), and potassium carbonate (346 mg) are suspended in dry NMP (5 mL) in a microwave vial and heated at 150° C. for 2 hours under microwave irradiation. The mixture is cooled, diluted with ethyl acetate and washed with water and brine. The organic phase is dried (Na$_2$SO$_4$), evaporated and the residue is purified by flash chromatography (10-60% ethyl acetate in cyclohexane) to give the title compound.

LC (Method 1): $t_R$=1.19 min; Mass spectrum (ESI$^+$): m/z=363 [M+H]$^+$.

The following intermediates are prepared in analogy to Intermediate 12, from the corresponding starting intermediates:

| Inter-mediate | Structure | Starting intermediates | Analysis |
|---|---|---|---|
| 13 | 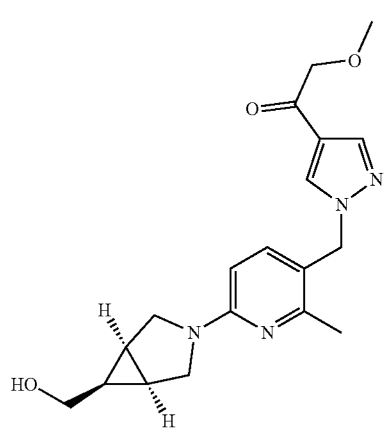 [SMILES: COCC(=O)c1cnn(Cc2ccc(N3C[C@@H]4[C@H](CO)[C@@H]4C3)nc2C)c1] | Intermediate 10 and endo-(3-Aza-bicyclo[3.1.0]hex-6-yl)-methanol hydrochloride, synthesis adapted from Bioorg. Med. Chem. Lett, 2010, 4741-4744.) Heated at 110° C. for 5 hours. | LC (Method 3): $t_R$ = 0.90 min; Mass spectrum (ESI$^+$): m/z = 357 [M + H]* |

| Intermediate | Structure | Starting intermediates | Analysis |
|---|---|---|---|
| 14 | 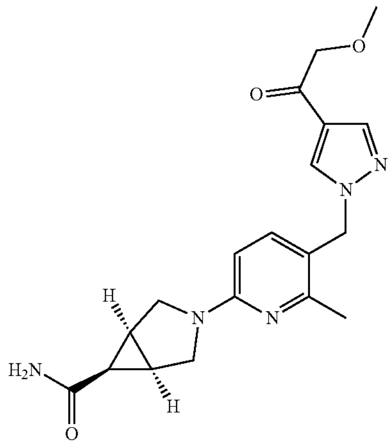 [SMILES: COCC(=O)c1cnn(Cc2ccc(N3C[C@@H]4[C@H](C3)[C@@H]4C(N)=O)nc2C)c1] | Intermediate 10 and endo-(3-Aza-bicyclo[3.1.0]hexane-6-carboxamide hydrochloride, synthesis of free base described in WO2010/116328) Heated at 140° C. for 4 hours. | LC (Method 3): $t_R$ = 0.77 min; Mass spectrum (ESI⁺): m/z = 370 [M + H]* |
| 15 | 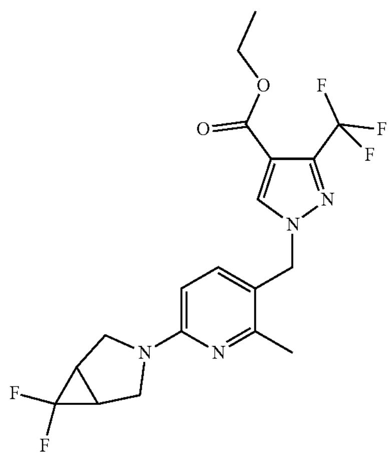 [SMILES: CCOC(=O)c1cn(Cc2ccc(N3CC4C(C3)C4(F)F)nc2C)nc1C(F)(F)F] | Intermediate 11 and 6,6-difluoro-3-aza-bicyclo[3.1.0]hexane hydrochloride, Heated at 150° C. for 4 hours. Purified by reverse phase flash chromatography (C18, 20-100% MeCN in water) | LC (Method 1): $t_R$ = 1.36 min; Mass spectrum (ESI⁺): m/z = 431 [M + H]* |

Intermediate 16

Ethyl 1-[(6-{3-azabicyclo[3.1.0]hexan-3-yl}-2-methylpyridin-3-yl)methyl]-1H-1,2,3-triazole-4-carboxylate

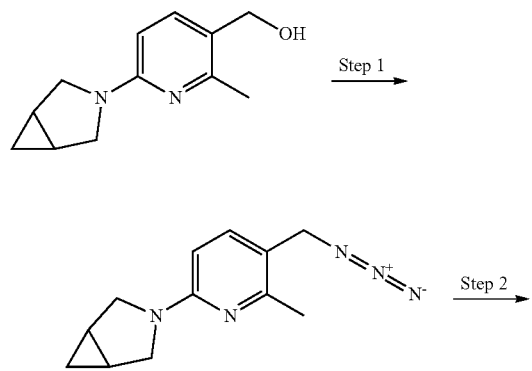

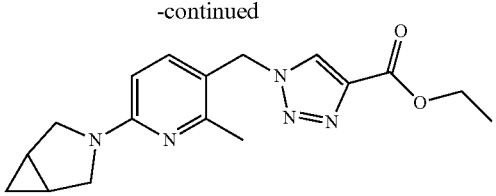

Step 1: 3-[5-(Azidomethyl)-6-methylpyridin-2-yl]-3-azabicyclo[3.1.0]hexane (6-{3-Azabicyclo[3.1.0]hexan-3-yl}-2-methylpyridin-3-yl)methanol (Intermediate 1, 1.30 g) is suspended in a mixture of dry toluene (10 mL) and acetonitrile (10 mL) and cooled to 0° C. under a nitrogen atmosphere. Diphenylphosphoryl azide (1.78 mL) is added dropwise followed by DBU (1.36 mL). The mixture is allowed to warm to room temperature and stirred for 2 hours. The solvent is removed, the residue is resuspended in ethyl acetate and washed with saturated aqueous sodium carbonate solution and brine. The organic phase is dried (Na₂SO₄) and evaporated and the residue is purified by flash chromatography (0-80% ethyl acetate in cyclohexane) to give the title compound.

Step 2: Ethyl 1-[(6-{3-azabicyclo[3.1.0]hexan-3-yl}-2-methylpyridin-3-yl)methyl]-1H-1,2,3-triazole-4-carboxylate 3-[5-(Azidomethyl)-6-methylpyridin-2-yl]-3-azabicyclo[3.1.0]hexane (0.60 g) and ethyl propiolate (0.28 g) are suspended in a mixture of tert-butanol (10 mL) and water (10 mL) and sodium ascorbate (0.52 g) and coppersulfate pentahydrate (0.13 g) are added. The mixture is stirred at room temperature for 6 hours then concentrated under vacuum. Water (40 mL) is added and the mixture is extracted with dichloromethane. The organic phase is dried ($Na_2SO_4$) and evaporated and the residue is purified by flash chromatography (0-100% ethyl acetate in cyclohexane) to give the title compound.

LC (Method 2): $t_R$=4.47 min; Mass spectrum (ESI$^+$): m/z=328 [M+H]$^+$.

Intermediate 17

Ethyl 1-[(6-{6,6-difluoro-3-azabicyclo[3.1.0]hexan-3-yl}-2-methylpyridin-3-yl)methyl]-1H-1,2,3-triazole-4-carboxylate

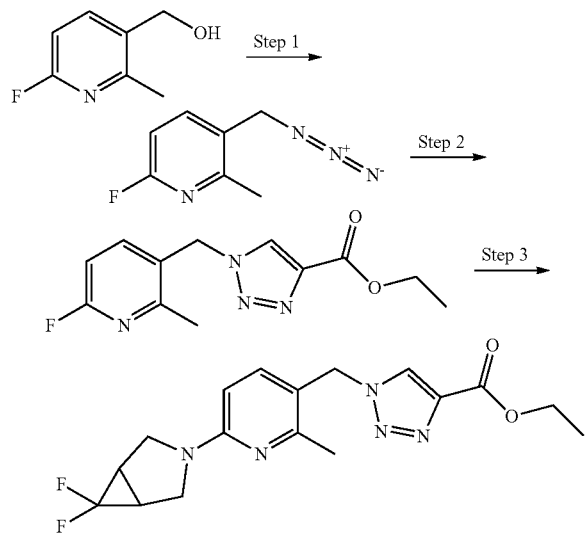

Step 1: 3-(Azidomethyl)-6-fluoro-2-methylpyridine (6-fluoro-2-methylpyridin-3-yl)methanol (0.80 g) is suspended in a mixture of dry toluene (10 mL) and acetonitrile (10 mL) and cooled to 0° C. under a nitrogen atmosphere. Diphenylphosphoryl azide (1.58 mL) is added dropwise followed by DBU (1.21 mL). The mixture is allowed to warm to room temperature and stirred for 2 hours. The solvent is removed and the residue is purified by flash chromatography (10-100% ethyl acetate in cyclohexane) to give the title compound.

GC (Method G1): $t_R$=7.24 min; Mass spectrum (EI$^+$): m/z=166 [M]$^+$.

Step 2: Ethyl 1-[(6-fluoro-2-methylpyridin-3-yl)methyl]-1H-1,2,3-triazole-4-carboxylate 3-(Azidomethyl)-6-fluoro-2-methylpyridine (0.66 g) and ethyl propiolate (0.43 g) are suspended in a mixture of tert-butanol (10 mL) and water (10 mL) and sodium ascorbate (0.79 g) and coppersulfate pentahydrate (0.20 g) are added. The mixture is stirred at room temperature for 6 hours then concentrated under vacuum. Water (40 mL) is added and the mixture is extracted with dichloromethane. The organic phase is dried ($Na_2SO_4$) and evaporated and the residue is purified by flash chromatography (0-100% ethyl acetate in cyclohexane) to give the title compound.

LC (Method 4): $t_R$=3.28 min; Mass spectrum (ESI$^+$): m/z=287 [M+H]$^+$.

Step 3: Ethyl 1-[(6-{6,6-difluoro-3-azabicyclo[3.1.0]hexan-3-yl}-2-methylpyridin-3-yl)methyl]-1H-1,2,3-triazole-4-carboxylate Ethyl 1-[(6-fluoro-2-methylpyridin-3-yl)methyl]-1H-1,2,3-triazole-4-carboxylate (90 mg), 6,6-difluoro-3-azabicyclo[3.1.0]hexane hydrochloride (64 mg), and potassium carbonate (104 mg) are suspended in dry NMP (1 mL) in a microwave vial and heated at 130° C. for 5 hours followed by 145° C. for 5 hours under microwave irradiation. The mixture is cooled, diluted with ethyl acetate and washed with water. The organic phase is dried ($Na_2SO_4$) and evaporated and the residue is purified by flash chromatography (0-100% ethyl acetate in cyclohexane) to give the title compound.

LC (Method 1): $t_R$=1.24 min; Mass spectrum (ESI$^+$): m/z=364 [M+H]$^+$.

Intermediate 18

1-[(6-{3-Azabicyclo[3.1.0]hexan-3-yl}-2-methylpyridin-3-yl)methyl]-1H-pyrazole-4-carboxylic acid

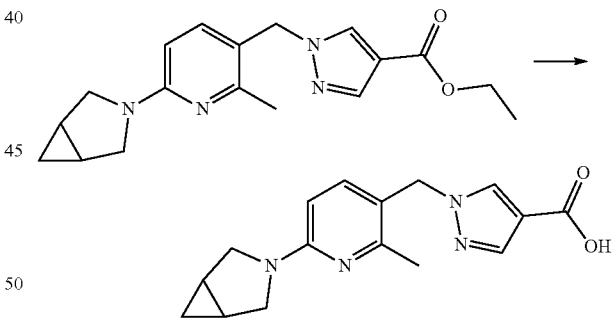

Ethyl 1-[(6-{3-azabicyclo[3.1.0]hexan-3-yl}-2-methylpyridin-3-yl)methyl]-1H-pyrazole-4-carboxylate (Intermediate 4, 7.60 g) and lithium hydroxide monohydrate (1.07 g) are suspended in a mixture of 1,4-dioxane (40 mL) and water (20 mL) and stirred at 70° C. for 1 hour. The mixture is concentrated under vacuum, diluted with water (50 mL) and washed twice with diethyl ether (2×100 mL). The aqueous phase is acidified to approximately pH4 by dropwise addition of concentrated aqueous hydrochloric acid and then extracted with dichloromethane (4×100 mL). The combined organic extracts are dried ($Na_2SO_4$) and the solvent evaporated to give the title compound.

LC (Method 5): $t_R$=2.44 min; Mass spectrum (ESI$^+$): m/z=299 [M+H]$^+$.

The following intermediates are prepared in analogy to Intermediate 18, from the corresponding starting intermediates:

| Intermediate | Structure | Starting intermediates | Analysis |
|---|---|---|---|
| 19 | (3-methyl-1-{[6-(3-azabicyclo[3.1.0]hex-3-yl)-2-methylpyridin-3-yl]methyl}-1H-pyrazole-4-carboxylic acid) | Intermediate 6 | LC (Method 1): $t_R$ = 0.72 min; Mass spectrum (ESI$^+$): m/z = 313 [M + H]$^+$ (contains an isomer as an impurity) |
| 20 | (3-(trifluoromethyl)-1-{[6-(3-azabicyclo[3.1.0]hex-3-yl)-2-methylpyridin-3-yl]methyl}-1H-pyrazole-4-carboxylic acid) | Intermediate 5 The product was purified by reverse phase flash chromatography (C18, 0-40% MeCN in water) | LC (Method 5): $t_R$ = 2.69 min; Mass spectrum (ESI$^+$): m/z = 367 [M + H]$^+$ |
| 21 | (3-isopropyl-1-{[6-(3-azabicyclo[3.1.0]hex-3-yl)-2-methylpyridin-3-yl]methyl}-1H-pyrazole-4-carboxylic acid) | Intermediate 7 | LC (Method 4): $t_R$ = 3.02-3.15 min; Mass spectrum (ESI$^+$): m/z = 341 [M + H]$^+$ (contains an isomer as an impurity) |
| 22 | (3-(trifluoromethyl)-1-{[6-(6,6-difluoro-3-azabicyclo[3.1.0]hex-3-yl)-2-methylpyridin-3-yl]methyl}-1H-pyrazole-4-carboxylic acid) | Intermediate 15 24 h reaction tim | LC (Method 1): $t_R$ = 0.83 min; Mass spectrum (ESI$^+$): m/z = 403 [M + H]$^+$ |

Intermediate 23

1-[(6-{6,6-Difluoro-3-azabicyclo[3.1.0]hexan-3-yl}-2-methylpyridin-3-yl)methyl]-1H-pyrazole-4-carboxylic Acid, Lithium Salt

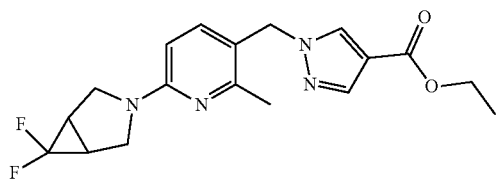

→

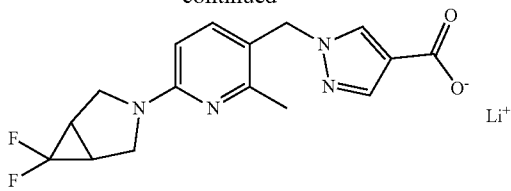

Ethyl 1-[(6-{6,6-difluoro-3-azabicyclo[3.1.0]hexan-3-yl}-2-methylpyridin-3-yl)methyl]-1H-pyrazole-4-carboxylate (Intermediate 12, 227 mg) and lithium hydroxide monohydrate (16.5 mg) are suspended in a mixture of THF (5 mL), methanol (5 mL) and water (2 mL) and stirred at 50° C. for 2 hours. The mixture is evaporated and dried under vacuum to give the crude title compound.

LC (Method 3): $t_R$=0.65 min; Mass spectrum (ESI$^+$): m/z=335 [M-Li+2H]$^+$.

The following intermediates are prepared in analogy to Intermediate 23, from the corresponding starting intermediates:

| Intermediate | Structure | Starting intermediates | Analysis |
|---|---|---|---|
| 24 | 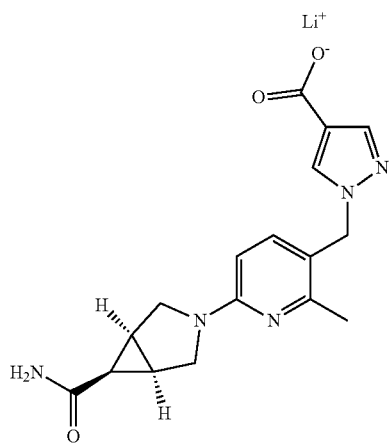 [SMILES: [Li+] ; Cc1nc(N2C[C@@H]3[C@H](C2)[C@@H]3C(N)=O)ccc1Cn1cc(C(=O)[O-])cn1] | Intermediate 14 | LC (Method 3): $t_R$ = 0.39 min; Mass spectrum (ESI$^+$): m/z = 343 [M—Li + 2H]$^+$ |
| 25 | 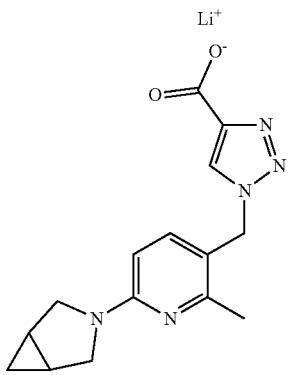 [SMILES: [Li+] ; Cc1nc(N2CC3CC3C2)ccc1Cn1cc(C(=O)[O-])nn1] | Intermediate 16 | LC (Method 2): $t_R$ = 2.32 min; Mass spectrum (ESI$^+$): m/z = 300 [M—Li + 2H]$^+$ |

-continued

| Intermediate | Structure | Starting intermediates | Analysis |
|---|---|---|---|
| 26 | 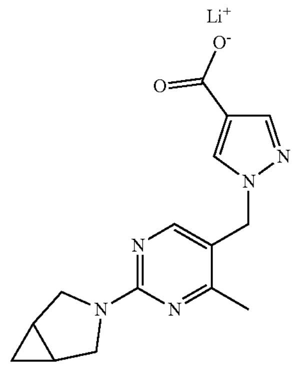 [SMILES: [Li+] ; Cc1nc(N2CC3CC3C2)ncc1Cn1cc(C(=O)[O-])cn1] | Intermediate 8 (Heated at 60° C. for 5 hours) | LC (Method 3): $t_R$ = 0.59 min; Mass spectrum (ESI⁺): m/z = 300 [M—Li + 2H]⁺ |
| 27 | 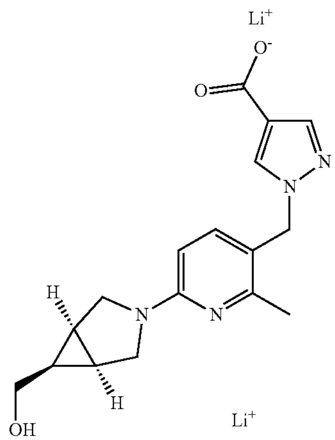 [SMILES: [Li+] ; Cc1nc(N2C[C@@H]3[C@H](CO)[C@@H]3C2)ccc1Cn1cc(C(=O)[O-])cn1] | Intermediate 13 | LC (Method 3): $t_R$ = 0.55 min; Mass spectrum (ESI⁺): m/z = 329 [M—Li + 2H]⁺ |
| 28 | 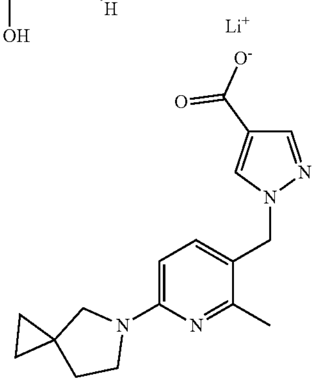 | Intermediate 9 Heated at 60° C. for 5 hours | LC (Method 3): $t_R$ = 0.65 min; Mass spectrum (ESI⁺): m/z = 313 [M—Li + 2H]⁺ |
| 29 | 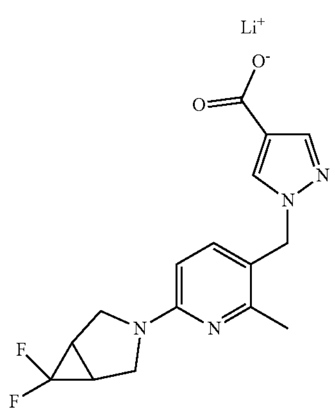 [SMILES: [Li+] ; Cc1nc(N2CC3C(C2)C3(F)F)ccc1Cn1cc(C(=O)[O-])cn1] | Intermediate 17 step 3 | LC (Method 1): $t_R$ = 0.65 min; Mass spectrum (ESI⁺): m/z = 336 [M—Li + 2H]⁺ |

Intermediate 30

(5R)-N1-[(2,4-Dimethoxyphenyl)methyl]-5H,6H,7H-cyclopenta[c]pyridine-1,5-diamine

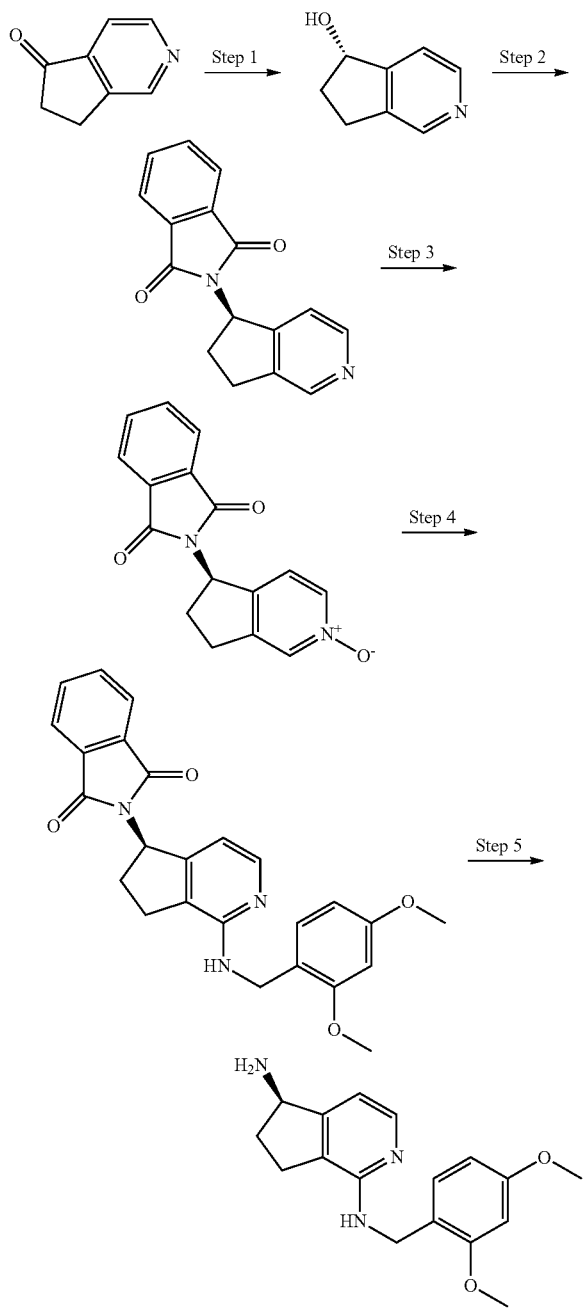

Step 1: (5S)-5H,6H,7H-Cyclopenta[c]pyridin-5-ol

Formic acid (49.6 mL, 1.31 mol) is dissolved in dichloromethane (900 mL), the mixture is cooled to 0° C. and triethylamine (161.8 mL, 1.16 mol) is added dropwise with stirring. 5H,6H,7H-Cyclopenta[c]pyridin-5-one (commercially available from ABCR AB 401490, 50 g) and chloro[(1S,2S)-(−)-2-amino-1,2-diphenylethyl](4-toluensulfonyl)amido)(mesitylene)ruthenium(II) (4.7 mg) are added and the mixture is allowed to slowly warm to room temperature (over 5 hours) then stirred overnight. The mixture is washed with saturated aqueous $Na_2CO_3$ solution (200 mL). The aqueous phase extracted three times with a 1:3 mixture of isopropanol/DCM. The organic phases are combined, dried ($Na_2SO_4$), and concentrated under vacuum. The residue is purified by flash chromatography (column loaded in DCM, eluted with ethyl acetate) to give the title compound.

GC (Method G1): $t_R$=7.36 min; Mass spectrum (EIk): m/z=135 [M]$^+$.

Chiral HPLC (Daicel chiralpak AS-H, hexane/ethanol 85:15, 1 mL/min, 25° C.) $t_R$=5.44 min, 99.9% (e.e. 99.8%).

Absolute stereochemistry assigned by analogy with Noyori et. al., J. Am. Chem. Soc., 1995, 117 (28), pp 7562-7563.

Step 2: 2-[(5R)-5H,6H,7H-Cyclopenta[c]pyridin-5-yl]-2,3-dihydro-1H-isoindole-1,3-dione (5S)-5H,6H,7H-Cyclopenta[c]pyridin-5-ol (39.3 g) is dissolved in dry THF (700 mL) and phthalimide (47.06 g) and triphenylphosphine (83.9 g) are added. The solution is cooled to 0° C. then diethylazodicarboxylate (DEAD, 40% solution in toluene, 145 mL) is added dropwise over 2 hours with ice cooling. The mixture is allowed to warm to room temperature and stirred overnight. The solvent is removed under vacuum and the residue redissolved in ethyl acetate, washed with water and brine, dried ($Na_2SO_4$) and the solvent evaporated. The residue is evaporated twice in vacuo from toluene then dissolved in toluene (1000 mL) and magnesium chloride (anhydrous, finely milled, 100 g) is added. The mixture is stirred at 60° C. for 1 hour then heptane (1000 mL) is added. The mixture is stirred at 60° C. for 1 hour then allowed to cool to room temperature and stirred overnight. The mixture is filtered through Celite and the filter cake washed with a 1:1 mixture of toluene/heptane. The combined filtrates are evaporated in vacuo and the residue is triturated with ethyl acetate to give the title compound.

LC (Method 4): $t_R$=2.74 min; Mass spectrum (ESI$^+$): m/z=265 [M]'.

Chiral HPLC (Daicel Chiralpak AD-H, hexane/isopropanol 70:30, 1 mL/min, 25° C.) $t_R$=10.08 min, 98.6% (e.e. 97.2%).

The mother liquor from the trituration step is evaporated and the residue purified by flash chromatography (10-40% ethyl acetate in cyclohexane) to give a second batch of the title compound.

LC (Method 4): $t_R$=2.77 min; Mass spectrum (ESI$^+$): m/z=265 [M]$^+$.

Chiral HPLC (Daicel Chiralpak AD-H, hexane/isopropanol 70:30, 1 mL/min, 25° C.) $t_R$=10.09 min, 92.0% (e.e. 84%).

Step 3: (5R)-5-(1,3-Dioxo-2,3-dihydro-1H-isoindol-2-yl)-5H,6H,7H-cyclopenta[c]pyridin-2-ium-2-olate 2-[(5R)-5H,6H,7H-Cyclopenta[c]pyridin-5-yl]-2,3-dihydro-1H-isoindole-1,3-dione (52.7 g) is dissolved in dichloromethane (400 mL), the solution is cooled to 0° C. and a suspension of 3-chloroperoxybenzoic acid (77%, 44.7 g) in dichloromethane (300 mL) is added dropwise with cooling. The mixture is allowed to warm to room temperature and stirred overnight. The mixture is washed with saturated aqueous $Na_2CO_3$ solution, the organic layer is collected, dried (Na$_2$SO$_4$) and concentrated under vacuum. The residue is recrystallized from toluene to give the title compound.

LC (Method 2): t$_R$=2.77 min; Mass spectrum (ESI$^+$): m/z=281 [M+H]$^+$.

Chiral HPLC (Daicel Chiralpak OJ-H, hexane/ethanol 70:30, 1 mL/min, 25° C.) t$_R$=18.27 min, 100% (e.e. 100%).

The mother liquor from the crystallization step is evaporated to give a second batch of the crude title compound.

LC (Method 3): t$_R$=0.70 min; Mass spectrum (ESI$^+$): m/z=281 [M]$^+$.

Step 4: 2-[(5R)-1-{[(2,4-Dimethoxyphenyl)methyl]amino}-5H,6H,7H-cyclopenta[c]pyridin-5-yl]-2,3-dihydro-1H-isoindole-1,3-dione (5R)-5-(1,3-Dioxo-2,3-dihydro-1H-isoindol-2-yl)-5H,6H,7H-cyclopenta[c]pyridin-2-ium-2-olate (21.2 g) is dissolved in dichloromethane (250 mL) and cooled to 0° C. Bromotripyrrolidinophosphonium hexafluorophosphate (45.8 g) is added with stirring, followed by N,N-diisopropylethylamine (45.8 mL) and 2,4-dimethoxybenzylamine (14.8 mL). The mixture is allowed to slowly warm to room temperature and stirred overnight. The mixture is washed with water and brine, the organic layer is collected, dried (Na$_2$SO$_4$) and concentrated. The residue is purified by flash chromatography (15-70% ethyl acetate in cyclohexane) to give the title compound.

LC (Method 2): t$_R$=4.80 min; Mass spectrum (ESI$^+$): m/z=430 [M+H]$^+$.

Chiral HPLC (Daicel Chiralpak OJ-H, hexane/ethanol 75:35, 1 mL/min, 25° C.) t$_R$=26.8 min, 100% (e.e. 100%).

Step 5: (5R)-N1-[(2,4-Dimethoxyphenyl)methyl]-5H,6H,7H-cyclopenta[c]pyridine-1,5-diamine 2-[(5R)-1-{[(2,4-Dimethoxyphenyl)methyl]amino}-5H,6H,7H-cyclopenta[c]pyridin-5-yl]-2,3-dihydro-1H-isoindole-1,3-dione (22.4 g) and hydrazine hydrate (7.68 mL) are dissolved in ethanol (450 mL) and THF (450 mL). The mixture is heated at 70° C. for 6 hours. The solution is allowed to cool, filtered, the solvent evaporated in vacuo and the residue dried under vacuum to give the title compound.

LC (Method 2): t$_R$=3.20 min; Mass spectrum (ESI$^+$): m/z=300 [M+H]$^+$.

Chiral HPLC (Daicel Chiralpak OJ-H, hexane/ethanol 80:20, 1 mL/min, 25° C.) t$_R$=17.23 min, 100% (e.e. 100%).

Intermediate 31

(5R)-5H,6H,7H-Cyclopenta[c]pyridine-1,5-diamine dihydrochloride

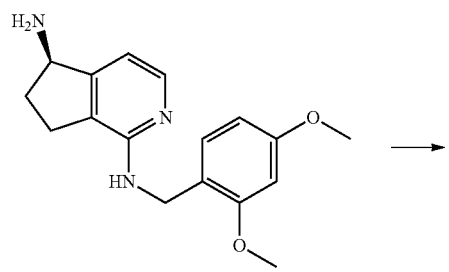

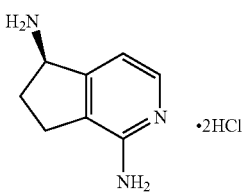

(5R)-N1-[(2,4-Dimethoxyphenyl)methyl]-5H,6H,7H-cyclopenta[c]pyridine-1,5-diamine (3.2 g) is dissolved in HCl 37% aqueous solution (10 mL). The mixture is stirred at 70° C. for 10 minutes. The mixture is concentrated under vacuum and the residue is triturated with diethyl ether to give the title compound.

LC (Method 5): t$_R$=0.50 min; Mass spectrum (ESI$^+$): m/z=150 [M+H]$^+$.

Intermediate 32

(5R)-N1-[(2,4-Dimethoxyphenyl)methyl]-3-methyl-5H,6H,7H-cyclopenta[c]pyridine-1,5-diamine

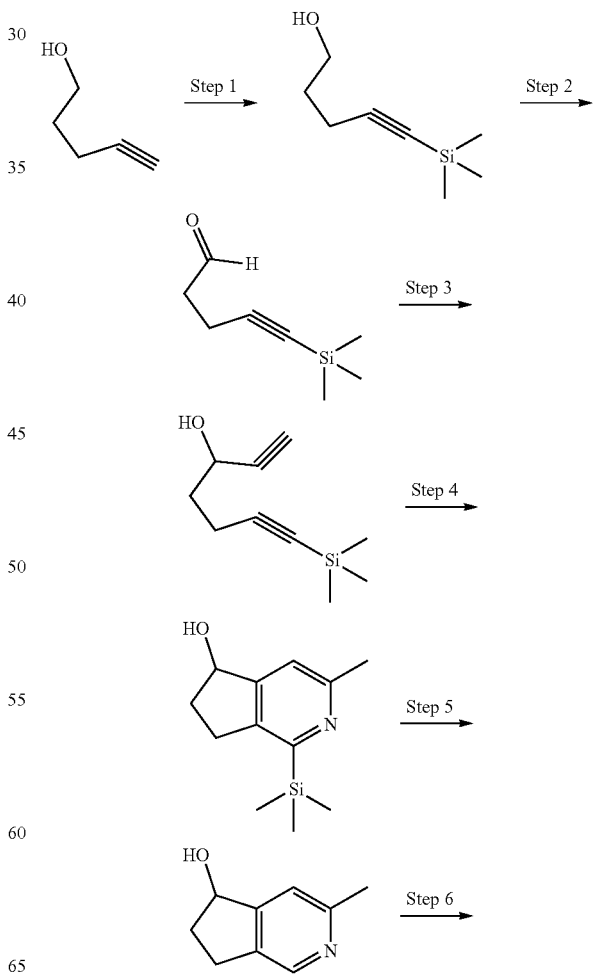

-continued

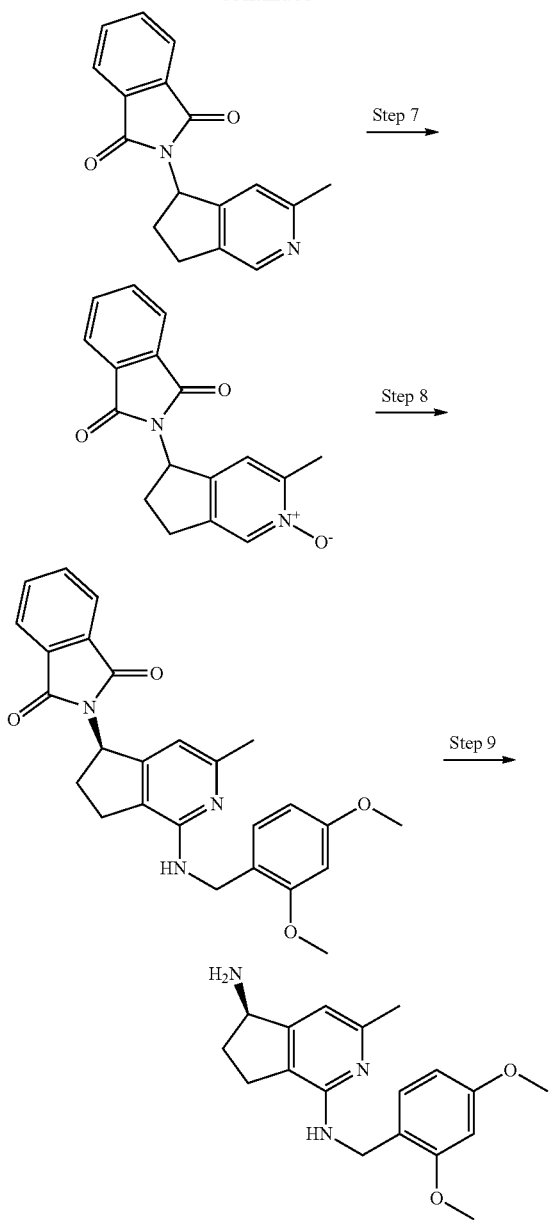

Step 1: 5-(Trimethylsilyl)pent-4-yn-1-ol

Pent-4-yn-1-ol (5.0 g) is dissolved in dry tetrahydrofuran (700 mL), cooled to −78° C. and treated dropwise with n-butyllithium (75 mL of a 1.6 M solution in hexane). After completed addition the mixture is stirred for 30 minutes at −78° C., then warmed to 0° C. and stirred for 2 hours. The mixture is recooled to −78° C. and treated with chlorotrimethylsilane (15.8 mL). The mixture is gradually warmed to room temperature and then heated for 12 hours at 50° C. Then the mixture is partitioned between 1 M aqueous hydrochloric acid and diethyl ether. The organic phase is washed with brine and dried (MgSO$_4$). The solvent is evaporated and the residue is purified by flash chromatography (10-40% ethyl acetate in petroleum ether) to give the title compound.

Mass spectrum (ESI$^+$): m/z=157 [M+H]$^+$.

Step 2: 5-(Trimethylsilyl)pent-4-ynal 5-(Trimethylsilyl)pent-4-yn-1-ol (6.9 g) is dissolved in dichloromethane (375 mL), cooled to 0° C. and treated with 1,1-dihydro-1,1,1-triacetoxy-1,2-benziodoxol-3(1H)-on (22.5 g). After completed addition the mixture is slowly warmed to room temperature and stirred for 12 hours. Then the mixture is partitioned between saturated aqueous solution of NaHCO$_3$ and dichloromethane. The organic phase is dried (MgSO$_4$) and the solvent is distilled off. The residue is purified by flash chromatography (DCM) to give the title compound.

Mass spectrum (ESI): m/z=169 [M−H]$^-$.

Step 3: 7-(Trimethylsilyl)hepta-1,6-diyn-3-ol 5-(Trimethylsilyl)pent-4-ynal (6.1 g) is dissolved in dry tetrahydrofuran (125 mL), cooled to −20° C. and treated dropwise with ethynylmagnesiumbromide (235 mL of a 0.5 M solution in tetrahydrofuran). After completed addition the mixture is slowly warmed to 0° C. and stirred for 20 minutes. Then the mixture is partitioned between saturated aqueous solution of NH$_4$Cl and ethyl acetate. The organic phase is dried (MgSO$_4$) and the solvent is evaporated in vacuo. The residue is purified by flash chromatography (dichloromethane) to give the title compound which is used directly in the next step.

Step 4: 3-Methyl-1-(trimethylsilyl)-5H,6H,7H-cyclopenta[c]pyridin-5-ol 7-(Trimethylsilyl)hepta-1,6-diyn-3-ol (2.1 g) and acetonitrile (1.8 mL) are dissolved in toluene (7 mL) and purged with argon for 5 minutes. Cyclopentadienylcobalt dicarbonyl (150 μL) is added and the mixture is stirred for 12 hours at 110° C. Then the mixture is partitioned between ethyl acetate and brine. The organic phase is dried (MgSO$_4$) and the solvent is evaporated in vacuo. The residue is purified by chromatography on Al$_2$O$_3$ (5% methanol in dichloromethane) to give the title compound.

LC (Method 7): t$_R$=0.65 min; Mass spectrum (ESI$^+$): m/z=222 [M+H]$^+$.

Step 5: 3-Methyl-5H,6H,7H-cyclopenta[c]pyridin-5-ol

3-Methyl-1-(trimethylsilyl)-5H,6H,7H-cyclopenta[c]pyridin-5-ol (1.5 g) is dissolved in 1,4-dioxane (20 mL) treated with hydrochloric acid (8.3 mL of a 4 M solution in 1,4-dioxane) and stirred for 12 hours at 90° C. and for further 48 hours at 80° C. Ammonia (5.2 mL of a 7 M solution in methanol) is added, the solvents are evaporated in vacuo and the residue is purified by flash chromatography (5-10% methanol in dichloromethane) to give the title compound.

LC (Method 7): t$_R$=0.08 min; Mass spectrum (ESI$^+$): m/z=150 [M+H]$^+$.

Step 6: 2-{3-Methyl-5H,6H,7H-cyclopenta[c]pyridin-5-yl}-2,3-dihydro-1H-isoindole-1,3-dione 3-Methyl-5H,6H,7H-cyclopenta[c]pyridin-5-ol (500 mg), phthalimide (590 mg) and tributylphosphine (1.16 mL) are dissolved in tetrahydrofuran (5 mL), cooled to 0° C. and treated dropwise with a solution of di-tert.-butyl azodicarboxylate (DBAD, 1.0 g) in tetrahydrofuran (5 mL). Then the mixture is stirred for 12 hours while warming to room temperature. The mixture is partitioned between saturated aqueous solution of NaHCO$_3$ and ethyl acetate. The organic phase is dried (MgSO$_4$) and the solvent is evaporated in vacuo. The residue is purified by flash chromatography (30-70% ethyl acetate in petroleum ether) to give the title compound.

LC (Method 7): t$_R$=0.68 min; Mass spectrum (ESI$^+$): m/z=279 [M+H]$^+$.

Step 7: 5-(1,3-Dioxo-2,3-dihydro-1H-isoindol-2-yl)-3-methyl-5H,6H,7H-cyclopenta[c]pyridin-2-ium-2-olate 2-{3-Methyl-5H,6H,7H-cyclopenta[c]pyridin-5-yl}-2,3-dihydro-1H-isoindole-1,3-dione (905 mg) is dissolved in dichloromethane (20 mL), cooled to 0° C. and treated with 3-chloroperbenzoic acid (960 mg). The mixture is stirred for 2 hours, partitioned between saturated aqueous solution of Na$_2$SO$_3$ and dichloromethane. The organic phase is dried (MgSO$_4$) and the solvent is evaporated in vacuo. The residue is purified by flash chromatography (5-10% methanol in dichloromethane) to give the title compound.

LC (Method 7): t$_R$=0.78 min; Mass spectrum (ESI$^+$): m/z=295 [M+H]$^+$.

Step 8: 2-[(5R)-1-{[(2,4-Dimethoxyphenyl)methyl]amino}-3-methyl-5H,6H,7H-cyclopenta[c]pyridin-5-yl]-2,3-dihydro-1H-isoindole-1,3-dione 5-(1,3-Dioxo-2,3-dihydro-1H-isoindol-2-yl)-3-methyl-5H,6H,7H-cyclopenta[c]pyridin-2-ium-2-olate (740 mg) is dissolved in dichloromethane (8 mL) and cooled to 0° C. Bromotripyrrolidinophosphonium hexafluorophosphate (1.52 g) is added with stirring, followed by N,N-diisopropylethylamine (1.52 mL) and 2,4-dimethoxybenzylamine (490 µL). The mixture is allowed to slowly warm to room temperature and stirred for 48 hours. The mixture is partitioned between saturated aqueous Na$_2$CO$_3$ solution and dichloromethane. The organic phase is dried (MgSO$_4$) and the solvents are evaporated in vacuo. The residue is purified by flash chromatography (30-70% ethyl acetate in petroleum ether) to give the title compound in racemic form.

LC (Method 7): t$_R$=0.87 min; Mass spectrum (ESI$^+$): m/z=444 [M+H]$^+$.

The pure enantiomers are obtained from the racemic mixture upon SFC separation on chiral phase (column: Chiralpak® IC (Daicel Corp.), 5 µm, 250 mm×21.2 mm; eluent: scCO$_2$/2-propanol 65:35, 40° C., 150 bar, 60 mL/min):

2-[(5R)-1-{[(2,4-Dimethoxyphenyl)methyl]amino}-3-methyl-5H,6H,7H-cyclopenta[c]pyridin-5-yl]-2,3-dihydro-1H-isoindole-1,3-dione: t$_R$=7.38 min 2-[(5S)-1-{[(2,4-Dimethoxyphenyl)methyl]amino}-3-methyl-5H,6H,7H-cyclopenta[c]pyridin-5-yl]-2,3-dihydro-1H-isoindole-1,3-dione: t$_R$=4.56 min Step 9: (5R)-N1-[(2,4-Dimethoxyphenyl)methyl]-3-methyl-5H,6H,7H-cyclopenta[c]pyridine-1,5-diamine 2-[(5R)-1-{[(2,4-Dimethoxyphenyl)methyl]amino}-3-methyl-5H,6H,7H-cyclo-penta[c]pyridin-5-yl]-2,3-dihydro-1H-isoindole-1,3-dione (340 mg) is dissolved in methanol (2 mL), treated with hydrazine-hydrate (76 µL) and the mixture is heated for 12 hours to 50° C. Then the mixture is diluted with ethyl acetate and stirred for 10 minutes. The precipitate is removed by filtration and the mother liquor is concentrated under vacuum. The residue is purified by HPLC on reversed phase (acetonitrile, water, ammonia) to give the title compound.

LC (Method 7): t$_R$=0.62 min; Mass spectrum (ESI$^+$): m/z=314 [M+H]$^+$.

Intermediate 33

(5R)-3-Methyl-5H,6H,7H-cyclopenta[c]pyridine-1,5-diamine dihydrochloride

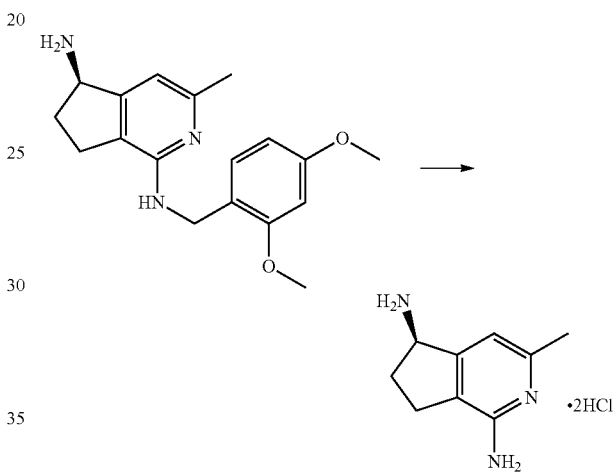

(5R)-N1-[(2,4-Dimethoxyphenyl)methyl]-3-methyl-5H,6H,7H-cyclopenta[c]pyridine-1,5-diamine (150 mg) is dissolved in concentrated aqueous hydrochloric acid (1 mL) and stirred for 1 hour at room temperature. The mixture is filtered and concentrated under vacuum. For 3 times toluene is added to the residue and evaporated again in vacuo to give the title compound.

LC (Method 7): t$_R$=0.08 min; Mass spectrum (ESI$^+$): m/z=164 [M+H]$^+$.

Intermediate 34

1-({6-[(1R,5S,6R)-6-Cyano-3-azabicyclo[3.1.0]hexan-3-yl]-2-methylpyridin-3-yl}methyl)-N-[(5R)-1-{[(2,4-dimethoxyphenyl)methyl]amino}-5H,6H,7H-cyclopenta[c]pyridin-5-yl]-1H-pyrazole-4-carboxamide

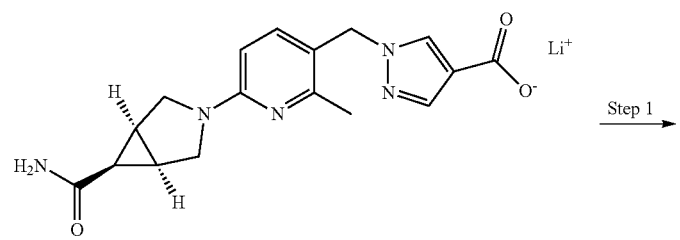

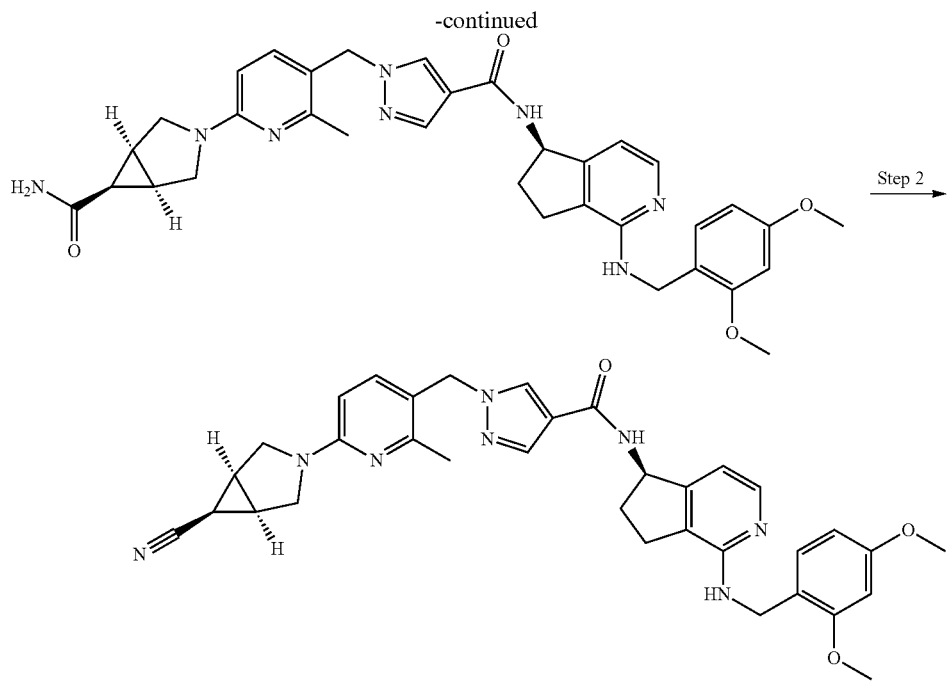

Step 1: (1R,5S,6R)-3-{5-[(4-{[(5R)-1-{[(2,4-dimethoxyphenyl)methyl]amino}-5H,6H,7H-cyclopenta[c]pyridin-5-yl]carbamoyl}-1H-pyrazol-1-yl)methyl]-6-methylpyridin-2-yl}-3-azabicyclo[3.1.0]hexane-6-carboxamide 1-({6-[(1R,5S,6R)-6-Carbamoyl-3-azabicyclo[3.1.0]hexan-3-yl]-2-methylpyridin-3-yl}methyl)-1H-pyrazole-4-carboxylic acid, lithium salt (Intermediate 24, 100 mg), (5R)-N1-[(2,4-dimethoxyphenyl)methyl]-5H,6H,7H-cyclopenta[c]pyridine-1,5-diamine (95 mg), PyBOP (180 mg) and triethylamine (200 µL) are dissolved in N,N-dimethylformamide (5 mL) and the reaction mixture is stirred at room temperature overnight. The solvent is evaporated in vacuo, the residue is suspended in ethyl acetate, washed with 0.2 M aqueous NaOH solution and brine, dried (Na$_2$SO$_4$) and the solvent evaporated. The residue is purified by flash chromatography (0-10% methanol in DCM) to give the title compound.

LC (Method 3): t$_R$=0.93 min; Mass spectrum (ESI$^+$): m/z=623 [M+H]$^+$.

Step 2: 1-({6-[(1R,5S,6R)-6-Cyano-3-azabicyclo[3.1.0]hexan-3-yl]-2-methylpyridin-3-yl}methyl)-N-[(5R)-1-{[(2,4-dimethoxyphenyl)methyl]amino}-5H,6H,7H-cyclopenta[c]pyridin-5-yl]-1H-pyrazole-4-carboxamide (1R,5S,6R)-3-{5-[(4-{[(5R)-1-{[(2,4-dimethoxyphenyl)methyl]amino}-5H,6H,7H-cyclopenta[c]pyridin-5-yl]carbamoyl}-1H-pyrazol-1-yl)methyl]-6-methylpyridin-2-yl}-3-azabicyclo[3.1.0]hexane-6-carboxamide (70 mg) is dissolved in a mixture of dry dichloromethane (5 mL) and dry acetonitrile (2 mL) and methyl N-(triethylammoniosulfonyl)carbamate, inner salt (Burgess' reagent, 29 mg) is added. The mixture is stirred at room temperature for 3 days then concentrated under vacuum. The residue is purified by flash chromatography (0-10% MeOH in EtOAc) to give the title compound.

LC (Method 3): t$_R$=1.04 min; Mass spectrum (ESI$^+$): m/z=605 [M+H]$^+$.

Intermediate 35

1-[(6-{5-Azaspiro[2.4]heptan-5-yl}-2-methylpyridin-3-yl)methyl]-N-[(5R)-1-{[(2,4-dimethoxyphenyl)methyl]amino}-5H,6H,7H-cyclopenta[c]pyridin-5-yl]-1H-pyrazole-4-carboxamide

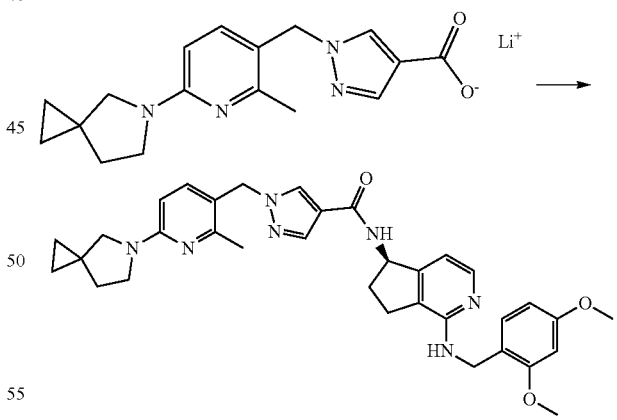

1-[(6-{5-Azaspiro[2.4]heptan-5-yl}-2-methylpyridin-3-yl)methyl]-1H-pyrazole-4-carboxylic acid, lithium salt (Intermediate 28, 100 mg), (5R)-N1-[(2,4-dimethoxyphenyl)methyl]-5H,6H,7H-cyclopenta[c]pyridine-1,5-diamine (93 mg), PyBOP (242 mg) and triethylamine (0.30 mL) are dissolved in N,N-dimethylformamide (5 mL) and the reaction mixture is stirred overnight at room temperature. The solvent is evaporated in vacuo, the residue is suspended in dichloromethane, washed with saturated aqueous NaHCO$_3$ solution and brine, dried (Na$_2$SO$_4$) and the solvent evaporated. The residue is purified by flash chromatography (30-100% EtOAc in cyclohexane) to give the title compound.

LC (Method 3): $t_R$=1.26 min; Mass spectrum (ESI$^+$): m/z=594 [M+H]$^+$.

Intermediate 36

1-[(6-{3-Azabicyclo[3.1.0]hexan-3-yl}-2-methyl-pyridin-3-yl)methyl]-N-[(5R)-1-{[(2,4-dimethoxyphenyl)methyl]amino}-3-methyl-5H,6H,7H-cyclopenta[c]pyridin-5-yl]-3-methyl-1H-pyrazole-4-carboxamide

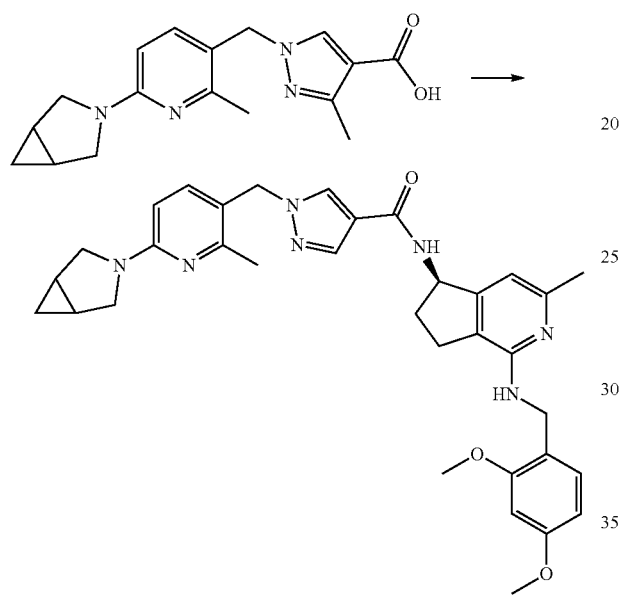

1-[(6-{3-Azabicyclo[3.1.0]hexan-3-yl}-2-methylpyridin-3-yl)methyl]-3-methyl-1H-pyrazole-4-carboxylic acid (Intermediate 19, 145 mg) and N,N-diisopropylethylamine (0.13 mL) are dissolved in N,N-dimethylformamide (1 mL), then HATU (120 mg) is added. The reaction mixture is stirred for 15 minutes, then (5R)-N1-[(2,4-dimethoxyphenyl)methyl]-3-methyl-5H,6H,7H-cyclopenta[c]pyridine-1,5-diamine (360 mg) is added. The reaction mixture is stirred at room temperature for 90 minutes. The mixture is diluted with water. The precipitate is collected by filtration and dissolved in ethyl acetate. After drying with MgSO$_4$ the solvent is evaporated in vacuo to give the title compound.

LC (Method 7): $t_R$=0.77 min; Mass spectrum (ESI$^+$): m/z=608 [M+H]$^+$.

Intermediate 37

3-[5-(Azidomethyl)-4-methylpyrimidin-2-yl]-3-azabicyclo[3.1.0]hexane

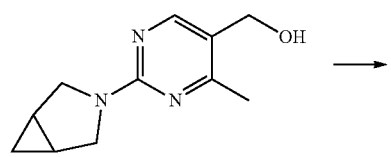

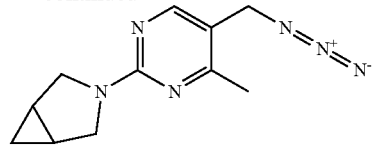

(2-{3-Azabicyclo[3.1.0]hexan-3-yl}-4-methylpyrimidin-5-yl)methanol (370 mg) is dissolved in toluene (5 mL) and acetonitrile (5 mL), cooled to −20° C. and treated with diphenylphosphorylazide (420 μL) and 2,3,4,6,7,8,9,10-octahydro-pyrimido[1,2-a]azepine (DBU, 321 μL). The mixture is stirred for 12 hours at room temperature and then partitioned between saturated aqueous NaHCO$_3$ solution and ethyl acetate. The organic phase is washed with brine and dried (MgSO$_4$). The solvents are evaporated to give the title compound.

LC (Method 7): $t_R$=0.78 min; Mass spectrum (ESI$^+$): m/z=231 [M+H]$^+$.

Intermediate 38

1-[(2-{3-Azabicyclo[3.1.0]hexan-3-yl}-4-methylpyrimidin-5-yl)methyl]-1H-1,2,3-triazole-4-carboxylic acid, lithium salt

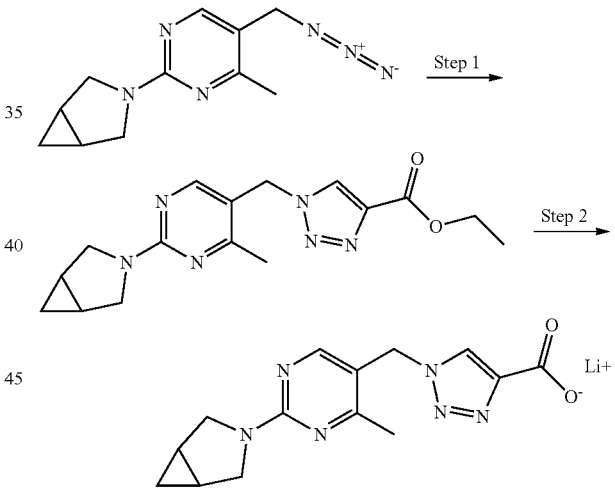

Step 1: Ethyl 1-[(2-{3-azabicyclo[3.1.0]hexan-3-yl}-4-methylpyrimidin-5-yl)methyl]-1H-1,2,3-triazole-4-carboxylate 3-[5-(Azidomethyl)-4-methylpyrimidin-2-yl]-3-azabicyclo[3.1.0]hexane (343 mg) and ethyl propiolate (170 μL) are suspended in a mixture of tert-butanol (10 mL), water (10 mL) and sodium ascorbate (295 mg) and coppersulfate pentahydrate (48 mg) are added. The mixture is stirred at room temperature for 48 hours then concentrated under vacuum. The mixture is partitioned between saturated aqueous NaHCO$_3$ solution and dichloromethane. The organic phase is washed with brine and dried (MgSO$_4$). The residue is purified by flash chromatography (0-50% ethyl acetate in cyclohexane) to give the title compound.

LC (Method 7): $t_R$=0.83 min; Mass spectrum (ESI⁺): m/z=329 [M+H]⁺.

Step 2: 1-[(2-{3-Azabicyclo[3.1.0]hexan-3-yl}-4-methylpyrimidin-5-yl)methyl]-1H-1,2,3-triazole-4-carboxylic acid, lithium salt A mixture of ethyl 1-[(2-{3-azabicyclo[3.1.0]hexan-3-yl}-4-methylpyrimidin-5-yl)methyl]-1H-1,2,3-triazole-4-carboxylate (50 mg), LiOH (6 mg) in tetrahydrofuran (100 µL), water (300 µL) and methanol (150 µL) is stirred for 12 hours at 50° C. The solvents are evaporated in vacuo to give the title compound.

LC (Method 7): $t_R$=0.69 min; Mass spectrum (ESI⁺): m/z=301 [M-Li+2H]⁺.

Intermediate 39

(5R)-5H,6H,7H-Cyclopenta[c]pyridine-1,5-diamine

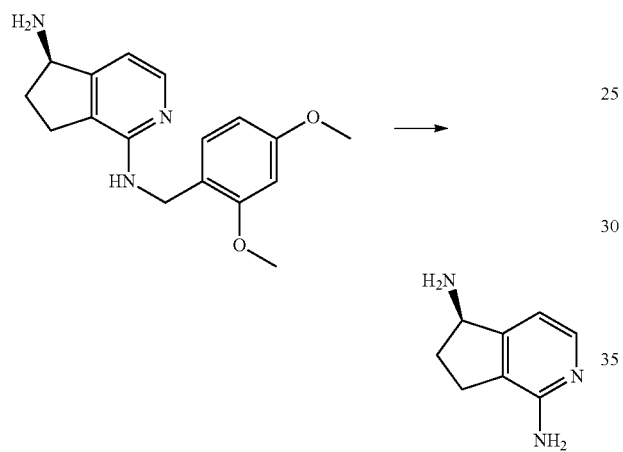

(5R)-N1-[(2,4-Dimethoxyphenyl)methyl]-5H,6H,7H-cyclopenta[c]pyridine-1,5-diamine (2.3 g) is dissolved in HCl 37% aqueous solution (10 mL). The mixture is stirred for 10 minutes at room temperature. Then the mixture is concentrated under vacuum and the residue is redissolved in 10% methanol in dichloromethane. The mixture is basified by addition of ammonia (7 M solution in methanol) and vigorously stirred for 30 minutes. Precipitate is removed by filtration and the mother liquor is concentrated. The residue is purified by chromatography on Al₂O₃ (0-20% methanol in dichloromethane) to give the title compound.

Mass spectrum (ESI⁺): m/z=150 [M+H]⁺.

Intermediate 40

1-[(6-{3-Azabicyclo[3.1.0]hexan-3-yl}-2-methylpyridin-3-yl)methyl]-3-(difluoromethyl)-1H-pyrazole-4-carboxylic Acid, Trifluoroacetic Acid Salt

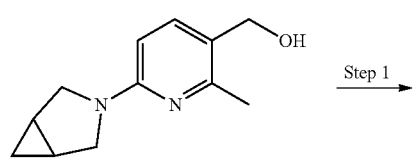

-continued

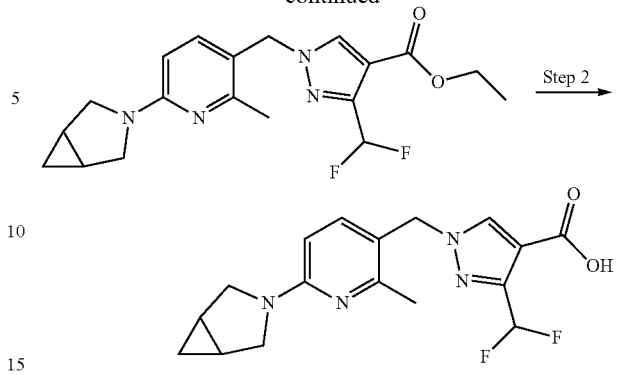

Step 1: Ethyl 1-[(6-{3-azabicyclo[3.1.0]hexan-3-yl}-2-methylpyridin-3-yl)methyl]-3-(difluoromethyl)-1H-pyrazole-4-carboxylate (6-{3-Azabicyclo[3.1.0]hexan-3-yl}-2-methylpyridin-3-yl)methanol (410 mg), tributylphosphine (600 µL) and ethyl 5-(difluoromethyl)-1H-pyrazole-4-carboxylate (380 mg) are dissolved in tetrahydrofuran (10 mL), cooled to −10° C. and treated with di-tert.-butyl azodicarboxylate (DBAD, 510 mg). Then the mixture is stirred for 30 minutes at room temperature. The mixture is purified by HPLC on reversed phase (acetonitrile, water, ammonia) to give the title compound.

LC (Method 8): $t_R$=1.14 min; Mass spectrum (ESI⁺): m/z=377 [M+H]⁺.

Step 2: 1-[(6-{3-Azabicyclo[3.1.0]hexan-3-yl}-2-methylpyridin-3-yl)methyl]-3-(difluoromethyl)-1H-pyrazole-4-carboxylic Acid, Trifluoroacetic Acid Salt A mixture of ethyl 1-[(6-{3-azabicyclo[3.1.0]hexan-3-yl}-2-methylpyridin-3-yl)methyl]-3-(difluoromethyl)-1H-pyrazole-4-carboxylate (240 mg), NaOH (3 mL of a 1 M aqueous solution) in 1,4-dioxane (2 mL) and methanol (5 mL) is stirred for 4 hours at 50° C. The mixture is neutralized by addition of hydrochloric acid (1 M aqueous solution) and purified by HPLC on reversed phase (acetonitrile, water, trifluoroacetic acid) to give the title compound.

LC (Method 7): $t_R$=0.72 min; Mass spectrum (ESI⁺): m/z=349 [M+H]⁺.

Intermediate 41

3-[5-(Azidomethyl)-4-methylpyrimidin-2-yl]-6,6-difluoro-3-azabicyclo[3.1.0]hexane

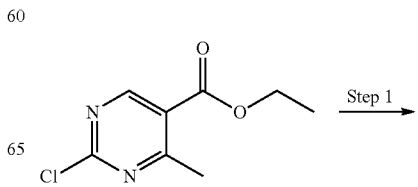

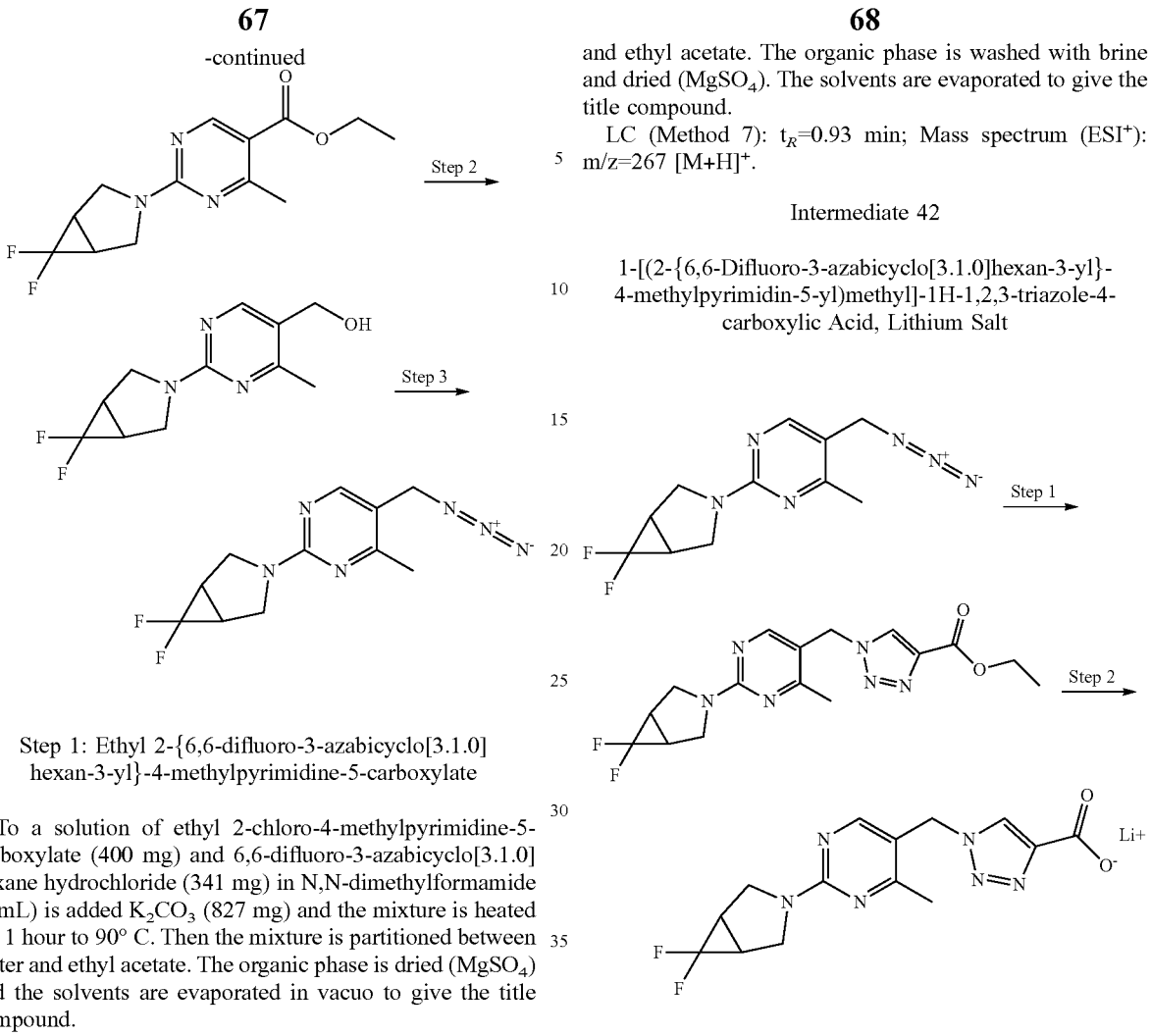

Step 1: Ethyl 2-{6,6-difluoro-3-azabicyclo[3.1.0]hexan-3-yl}-4-methylpyrimidine-5-carboxylate To a solution of ethyl 2-chloro-4-methylpyrimidine-5-carboxylate (400 mg) and 6,6-difluoro-3-azabicyclo[3.1.0]hexane hydrochloride (341 mg) in N,N-dimethylformamide (4 mL) is added $K_2CO_3$ (827 mg) and the mixture is heated for 1 hour to 90° C. Then the mixture is partitioned between water and ethyl acetate. The organic phase is dried ($MgSO_4$) and the solvents are evaporated in vacuo to give the title compound.

LC (Method 7): $t_R$=1.07 min; Mass spectrum (ESI$^+$): m/z=284 [M+H]$^+$.

Step 2: 2-{6,6-Difluoro-3-azabicyclo[3.1.0]hexan-3-yl}-4-methylpyrimidin-5-yl)methanol Ethyl 2-{6,6-difluoro-3-azabicyclo[3.1.0]hexan-3-yl}-4-methylpyrimidine-5-carboxylate (200 mg) is dissolved in tetrahydrofuran (3 mL), cooled to 0° C., treated with LiBH$_4$ (77 mg) and methanol (85 μL). The mixture is stirred for 12 hours at 50° C. Thereafter the mixture is slowly treated with water (10 mL), vigorously stirred for 10 minutes and then partitioned between water and ethyl acetate. The aqueous phase is extracted with ethyl acetate. The combined organic phases are dried (MgSO$_4$) and the solvents are evaporated in vacuo to give the title compound.

LC (Method 7): $t_R$=0.65 min; Mass spectrum (ESI$^+$): m/z=242 [M+H]$^+$.

Step 3: 3-[5-(Azidomethyl)-4-methylpyrimidin-2-yl]-6,6-difluoro-3-azabicyclo[3.1.0]hexane 2-{6,6-Difluoro-3-azabicyclo[3.1.0]hexan-3-yl}-4-methylpyrimidin-5-yl)methanol (254 mg) is dissolved in toluene (5 mL) and acetonitrile (5 mL), cooled to 0° C. and treated with diphenylphosphorylazide (245 μL) and 2,3,4,6,7,8,9,10-octahydro-pyrimido[1,2-a]azepine (188 μL). The mixture is stirred for 12 hours at room temperature and this then partitioned between saturated aqueous NaHCO$_3$ solution and ethyl acetate. The organic phase is washed with brine and dried (MgSO$_4$). The solvents are evaporated to give the title compound.

LC (Method 7): $t_R$=0.93 min; Mass spectrum (ESI$^+$): m/z=267 [M+H]$^+$.

Intermediate 42

1-[(2-{6,6-Difluoro-3-azabicyclo[3.1.0]hexan-3-yl}-4-methylpyrimidin-5-yl)methyl]-1H-1,2,3-triazole-4-carboxylic Acid, Lithium Salt

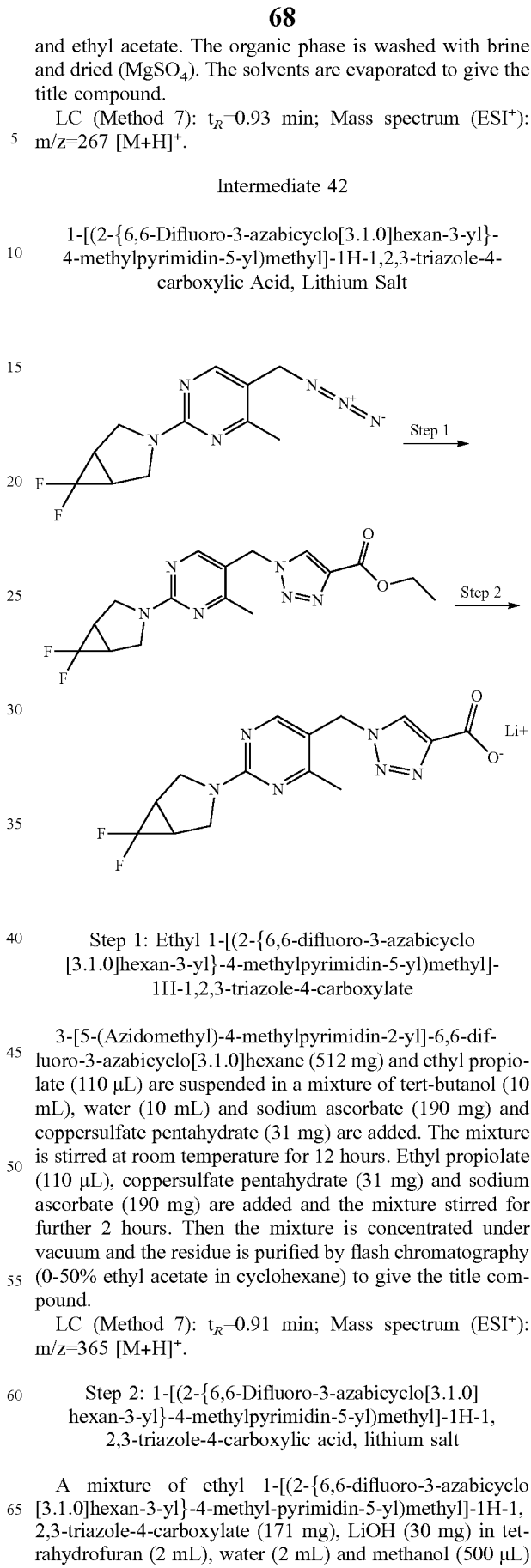

Step 1: Ethyl 1-[(2-{6,6-difluoro-3-azabicyclo[3.1.0]hexan-3-yl}-4-methylpyrimidin-5-yl)methyl]-1H-1,2,3-triazole-4-carboxylate 3-[5-(Azidomethyl)-4-methylpyrimidin-2-yl]-6,6-difluoro-3-azabicyclo[3.1.0]hexane (512 mg) and ethyl propiolate (110 μL) are suspended in a mixture of tert-butanol (10 mL), water (10 mL) and sodium ascorbate (190 mg) and coppersulfate pentahydrate (31 mg) are added. The mixture is stirred at room temperature for 12 hours. Ethyl propiolate (110 μL), coppersulfate pentahydrate (31 mg) and sodium ascorbate (190 mg) are added and the mixture stirred for further 2 hours. Then the mixture is concentrated under vacuum and the residue is purified by flash chromatography (0-50% ethyl acetate in cyclohexane) to give the title compound.

LC (Method 7): $t_R$=0.91 min; Mass spectrum (ESI$^+$): m/z=365 [M+H]$^+$.

Step 2: 1-[(2-{6,6-Difluoro-3-azabicyclo[3.1.0]hexan-3-yl}-4-methylpyrimidin-5-yl)methyl]-1H-1,2,3-triazole-4-carboxylic acid, lithium salt A mixture of ethyl 1-[(2-{6,6-difluoro-3-azabicyclo[3.1.0]hexan-3-yl}-4-methyl-pyrimidin-5-yl)methyl]-1H-1,2,3-triazole-4-carboxylate (171 mg), LiOH (30 mg) in tetrahydrofuran (2 mL), water (2 mL) and methanol (500 μL)

is stirred for 12 hours at 50° C. The solvents are evaporated in vacuo to give the title compound, which is used directly in the next step.

Intermediate 43

1-[(2-{6,6-Difluoro-3-azabicyclo[3.1.0]hexan-3-yl}-4-methylpyrimidin-5-yl)methyl]-N-[(5R)-1-{[(2,4-dimethoxyphenyl)methyl]amino}-3-methyl-5H,6H,7H-cyclopenta[c]pyridin-5-yl]-1H-1,2,3-triazole-4-carboxamide

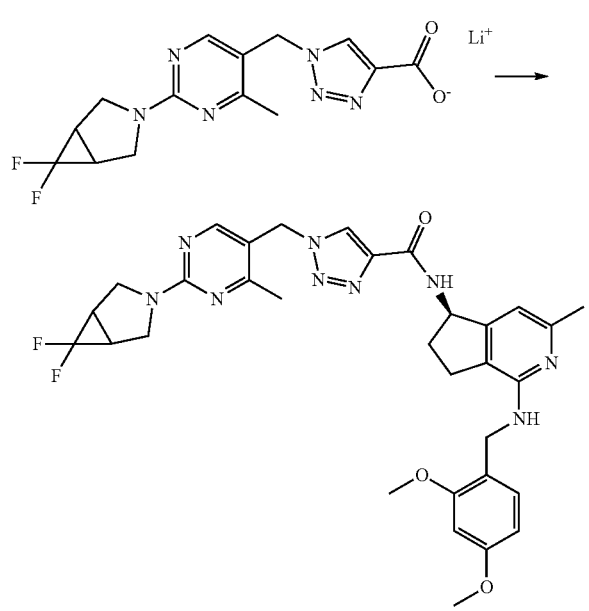

1-[(2-{6,6-Difluoro-3-azabicyclo[3.1.0]hexan-3-yl}-4-methylpyrimidin-5-yl)methyl]-1H-1,2,3-triazole-4-carboxylic acid, lithium salt (15 mg) is dissolved in N,N-dimethylformamide (500 μL), treated with HATU (17 mg) and stirred for 10 minutes at room temperature. (5R)-N1-[(2,4-Dimethoxyphenyl)methyl]-3-methyl-5H,6H,7H-cyclopenta[c]pyridine-1,5-diamine (14 mg) and N,N-diisopropylethylamine (23 μL) are added and the mixture is stirred for 3 hours at room temperature. The mixture is purified by HPLC on reversed phase (acetonitrile, water, ammonia) to give the title compound.

LC (Method 7): $t_R$=0.85 min; Mass spectrum (ESI$^+$): m/z=632 [M+H]$^+$.

Intermediate 44

1-[(6-{3-Azabicyclo[3.1.0]hexan-3-yl}-2-methylpyridin-3-yl)methyl]-3-methoxy-1H-pyrazole-4-carboxylic acid, trifluoroacetic acid salt

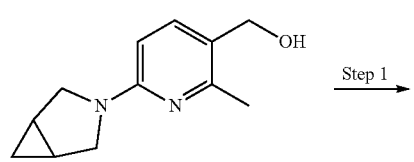

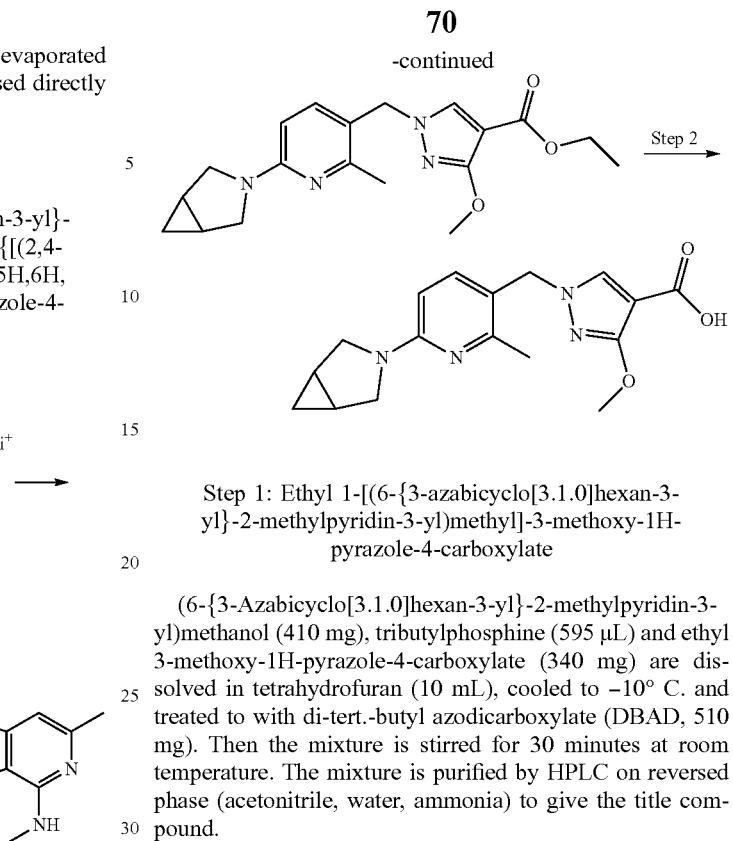

Step 1: Ethyl 1-[(6-{3-azabicyclo[3.1.0]hexan-3-yl}-2-methylpyridin-3-yl)methyl]-3-methoxy-1H-pyrazole-4-carboxylate (6-{3-Azabicyclo[3.1.0]hexan-3-yl}-2-methylpyridin-3-yl)methanol (410 mg), tributylphosphine (595 μL) and ethyl 3-methoxy-1H-pyrazole-4-carboxylate (340 mg) are dissolved in tetrahydrofuran (10 mL), cooled to −10° C. and treated to with di-tert.-butyl azodicarboxylate (DBAD, 510 mg). Then the mixture is stirred for 30 minutes at room temperature. The mixture is purified by HPLC on reversed phase (acetonitrile, water, ammonia) to give the title compound.

LC (Method 8): $t_R$=1.09 min; Mass spectrum (ESI$^+$): m/z=357 [M+H]$^+$.

Step 2: 1-[(6-{3-Azabicyclo[3.1.0]hexan-3-yl}-2-methylpyridin-3-yl)methyl]-3-methoxy-1H-pyrazole-4-carboxylic Acid, Trifluoroacetic Acid Salt A mixture of ethyl 1-[(6-{3-azabicyclo[3.1.0]hexan-3-yl}-2-methylpyridin-3-yl)methyl]-3-methoxy-1H-pyrazole-4-carboxylate (310 mg), NaOH (5 mL of a 1 M aqueous solution) in 1,4-dioxane (2 mL) and methanol (5 mL) is stirred for 4 hours at 50° C. The mixture is neutralized by addition of hydrochloric acid (1 M aqueous solution) and purified by HPLC on reversed phase (acetonitrile, water, trifluoroacetic acid) to give the title compound.

LC (Method 7): $t_R$=0.67 min; Mass spectrum (ESI$^+$): m/z=329 [M+H]$^+$.

Intermediate 45

N-[(5R)-1-Amino-5H,6H,7H-cyclopenta[c]pyridin-5-yl]-1-[(6-fluoro-2-methylpyridin-3-yl)methyl]-1H-pyrazole-4-carboxamide

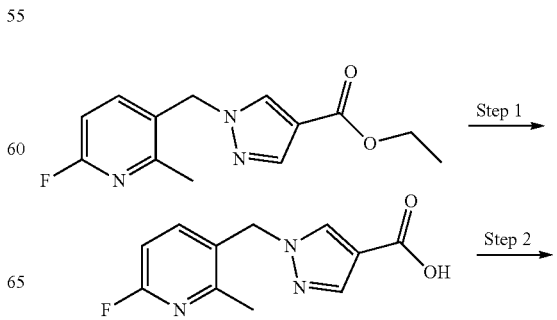

-continued

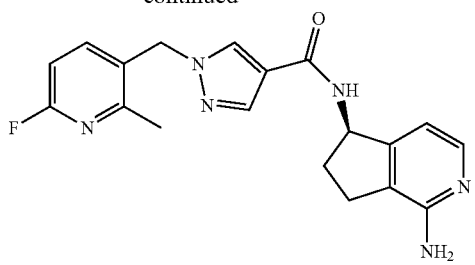

Step 1: 1-[(6-Fluoro-2-methylpyridin-3-yl)methyl]-1H-pyrazole-4-carboxylic Acid A mixture of ethyl 1-[(6-fluoro-2-methylpyridin-3-yl)methyl]-1H-pyrazole-4-carboxylate (9.1 g), LiOH (1.7 g) in tetrahydrofuran (150 mL) and water (150 mL) is stirred for 48 hours at 60° C. Acetic acid (3.8 mL) is added, the solvents are evaporated in vacuo and the residue is partitioned between water and dichloromethane/chloroform 9:1. The organic phase is washed with brine, dried (MgSO$_4$) and evaporated in vacuo to give the title compound, which is used directly in the next step.

LC (Method 7): $t_R$=0.72 min; Mass spectrum (ESI$^+$): m/z=236 [Mi+H]$^+$.

Step 2: N-[(5R)-1-Amino-5H,6H,7H-cyclopenta[c]pyridin-5-yl]-1-[(6-fluoro-2-methylpyridin-3-yl)methyl]-1H-pyrazole-4-carboxamide 1-[(6-Fluoro-2-methylpyridin-3-yl)methyl]-1H-pyrazole-4-carboxylic acid (530 mg), (5R)-5H,6H,7H-cyclopenta[c]pyridine-1,5-diamine dihydrochloride (500 mg) and N,N-diisopropylethylamine (1.5 mL) are dissolved in N,N-dimethylformamide (10 mL), treated with HATU (875 mg) and stirred for 1 hour at room temperature. The mixture is purified by HPLC on reversed phase (acetonitrile, water, ammonia) to give the title compound.

LC (Method 8): $t_R$=0.75 min; Mass spectrum (ESI$^+$): m/z=367 [M+H]$^+$.

C) Syntheses of Compounds According to the Invention

Example 1

N-[(5R)-1-Amino-5H,6H,7H-cyclopenta[c]pyridin-5-yl]-1-[(6-{3-azabicyclo[3.1.0]hexan-3-yl}-2-methylpyridin-3-yl)methyl]-1H-pyrazole-4-carboxamide

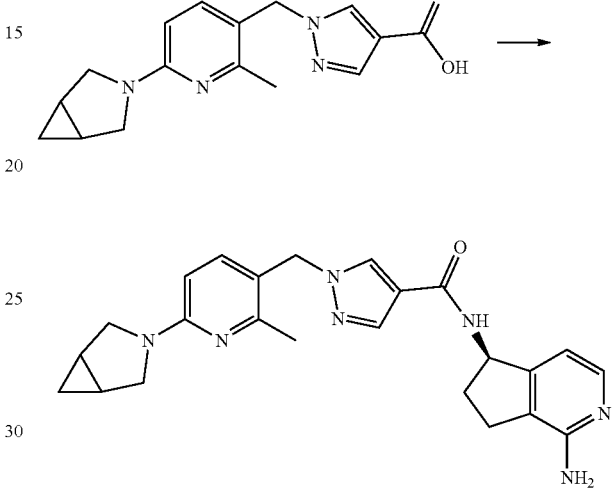

1-[(6-{3-Azabicyclo[3.1.0]hexan-3-yl}-2-methylpyridin-3-yl)methyl]-1H-pyrazole-4-carboxylic acid (Intermediate 18, 480 mg) and N,N-diisopropylethylamine (0.70 mL) are dissolved in N,N-dimethylformamide (3 mL), then HATU (734 mg) is added. The reaction mixture is stirred for 5 minutes, then (5R)-5H,6H,7H-cyclopenta[c]pyridine-1,5-diamine dihydrochloride (Intermediate 31, 360 mg) is added. The reaction mixture is stirred at room temperature overnight. The solvent is evaporated in vacuo and the residue is purified by HPLC on reversed phase (acetonitrile, water) to give the title compound.

LC (Method 5): $t_R$=3.04 min; Mass spectrum (ESI$^+$): m/z=430 [M+H]$^+$.

The following examples are prepared in analogy to Example 1, starting from the corresponding intermediates:

| Example | Structure | Starting intermediates | Analysis (Comment) |
|---|---|---|---|
| 2 | 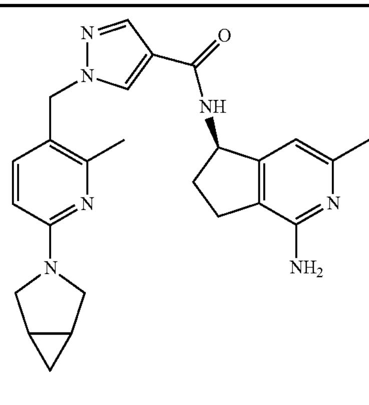 | Acid: Intermediate 18 (28 mg) Amine: Intermediate 33 (20 mg) 2 h reaction time. | LC (Method 4): $t_R$ = 2.74 min; Mass spectrum (ESI$^+$): m/z = 444 [M + H]$^+$ |

| Example | Structure | Starting intermediates | Analysis (Comment) |
| --- | --- | --- | --- |
| 3 | 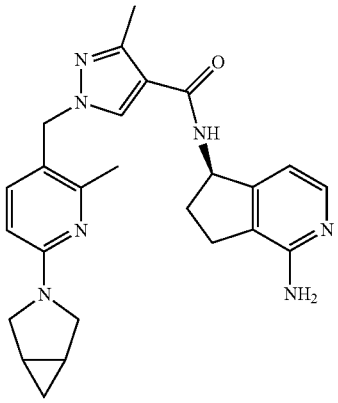 [SMILES: Cc1nc(N2CC3CC3C2)ccc1Cn1cc(C(=O)N[C@@H]2CCc3c2ccnc3N)c(C)n1] | Acid: Intermediate 19 (60 mg) Amine: Intermediate 31 (47 mg) 2 h reaction time. | LC (Method 2): $t_R$ = 3.67 min; Mass spectrum (ESI$^+$): m/z = 444 [M + H]$^+$ (Product further purified by preparative HPLC Column: Daicel Chiralpak AD-H hexane/isopropanol 70:30, 15 mL/min, 25° C., $t_R$ = 6.61 min) |
| 4 | 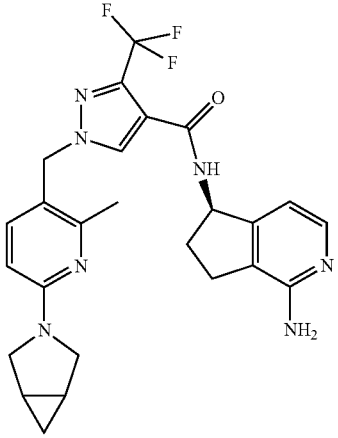 [SMILES: Cc1nc(N2CC3CC3C2)ccc1Cn1cc(C(=O)N[C@@H]2CCc3c2ccnc3N)c(C(F)(F)F)n1] | Acid: Intermediate 20 (38 mg) Amine: Intermediate 31 (25 mg) | LC (Method 2): $t_R$ = 4.37 min; Mass spectrum (ESI$^+$): m/z = 498 [M + H]$^+$ (2 h reaction time. Purified by flash chromatography (40-100% EtOAc in cyclohexane)) |
| 5 | 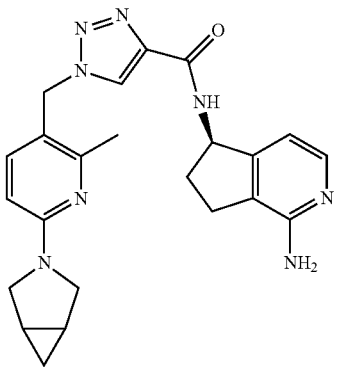 [SMILES: Cc1nc(N2CC3CC3C2)ccc1Cn1cc(C(=O)N[C@@H]2CCc3c2ccnc3N)nn1] | Acid: Intermediate 25 (40 mg) Amine: Intermediate 31 (36 mg) | LC (Method 2): $t_R$ = 3.97 min; Mass spectrum (ESI$^+$): m/z = 431 [M + H]$^+$ (2 h reaction time) |

-continued

| Example | Structure | Starting intermediates | Analysis (Comment) |
|---|---|---|---|
| 6 | 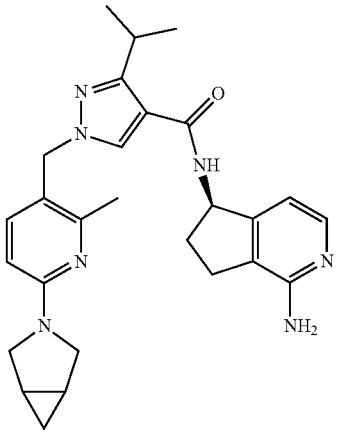 [SMILES: Cc1nc(N2CC3CC3C2)ccc1Cn1cc(C(=O)N[C@@H]2CCc3c2ccnc3N)c(C(C)C)n1] | Acid: Intermediate 21 (80 mg) Amine: Intermediate 31 (57 mg) 2 h reaction time. | LC (Method 2): $t_R$ = 4.05 min; Mass spectrum (ESI$^+$): m/z = 472 [M + H]$^+$ (Product further purified by preparative HPLC Column: Daicel Chiralpak AD-H hexane/isopropanol 70:30, 15 mL/min, 25° C., $t_R$ = 5.19 min) |
| 7 | 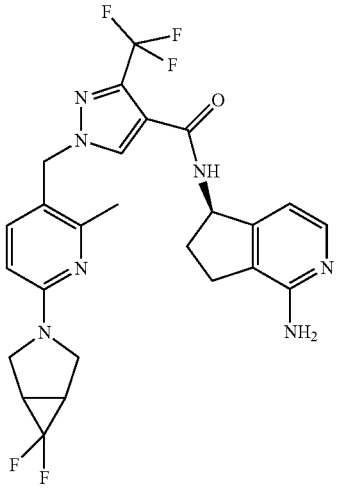 [SMILES: Cc1nc(N2CC3C(C2)C3(F)F)ccc1Cn1cc(C(=O)N[C@@H]2CCc3c2ccnc3N)c(C(F)(F)F)n1] | Acid: Intermediate 22 (102 mg) Amine: Intermediate 31 (62 mg) | LC (Method 2): $t_R$ = 4.38 min; Mass spectrum (ESI$^+$): m/z = 534 [M + H]$^+$ (2 h reaction time. Further purified by flash chromatography (0-10% methanol in DCM)) |
| 8 | 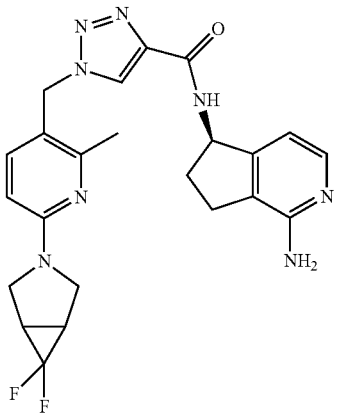 [SMILES: Cc1nc(N2CC3C(C2)C3(F)F)ccc1Cn1cc(C(=O)N[C@@H]2CCc3c2ccnc3N)nn1] | Acid: Intermediate 29 (18 mg) Amine: Intermediate 31 (12 mg) | LC (Method 5): $t_R$ = 3.24 min; Mass spectrum (ESI$^+$): m/z = 467 [M + H]$^+$ (2 h reaction time. Further purified by flash chromatography (0-10% methanol in DCM)) |

Example 9

N-[(5R)-1-Amino-5H,6H,7H-cyclopenta[c]pyridin-5-yl]-1-[(6-{6,6-difluoro-3-azabicyclo[3.1.0]hexan-3-yl}-2-methylpyridin-3-yl)methyl]-1H-pyrazole-4-carboxamide

Example 10

N-[(5R)-1-Amino-3-methyl-5H,6H,7H-cyclopenta[c]pyridin-5-yl]-1-[(6-{6,6-difluoro-3-azabicyclo[3.1.0]hexan-3-yl}-2-methylpyridin-3-yl)methyl]-1H-pyrazole-4-carboxamide

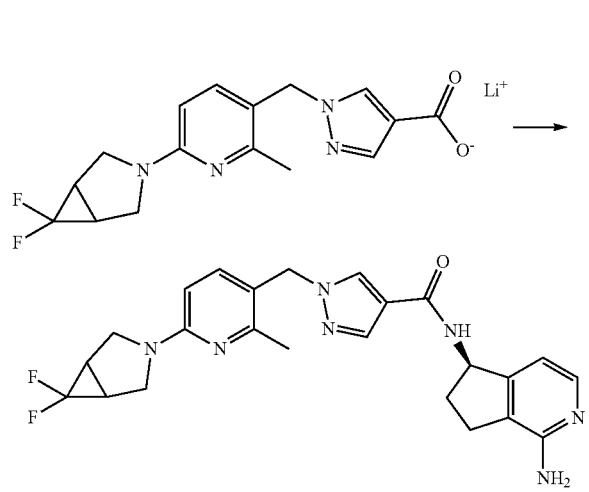

1-[(6-{6,6-Difluoro-3-azabicyclo[3.1.0]hexan-3-yl}-2-methylpyridin-3-yl)methyl]-1H-pyrazole-4-carboxylic acid, lithium salt (Intermediate 23, 212 mg), (5R)-5H,6H,7H-cyclopenta[c]pyridine-1,5-diamine dihydrochloride (Intermediate 31, 152 mg), HATU (260 mg) and N,N-diisopropylethylamine (0.32 mL) are dissolved in N,N-dimethylformamide (1 mL) and the reaction mixture is stirred at room temperature overnight. The solvent is evaporated in vacuo, the residue is suspended in ethyl acetate, washed with 0.2 M aqueous NaOH solution and brine. The organic phase is dried (Na$_2$SO$_4$) and the solvents are evaporated in vacuo. The residue is purified by flash chromatography (0-10% methanol in DCM) to give the title compound.

LC (Method 4): t$_R$=2.57 min; Mass spectrum (ESI$^+$): m/z=466 [M+H]$^+$.

1-[(6-{6,6-Difluoro-3-azabicyclo[3.1.0]hexan-3-yl}-2-methylpyridin-3-yl)methyl]-1H-pyrazole-4-carboxylic acid, lithium salt (Intermediate 23, 28 mg), (5R)-3-methyl-5H,6H,7H-cyclopenta[c]pyridine-1,5-diamine dihydrochloride (Intermediate 33, 20 mg), PyBOP (53 mg) and N,N-diisopropylethylamine (73 µL) are dissolved in N,N-dimethylformamide (2 mL) and the reaction mixture is stirred at 50° C. for 2 hours. The solvent is evaporated in vacuo, the residue is suspended in ethyl acetate, washed with 0.2 M aqueous NaOH solution and brine. The organic phase is dried (Na$_2$SO$_4$) and the solvents are evaporated in vacuo. The residue is purified by flash chromatography (0-10% methanol in DCM) to give the title compound.

LC (Method 6): t$_R$=8.19 min; Mass spectrum (ESI$^+$): m/z=480 [M+H]$^+$.

The following examples are prepared in analogy to Example 10, starting from the corresponding intermediates:

| Example | Structure | Starting intermediates | Analysis |
|---|---|---|---|
| 11 | 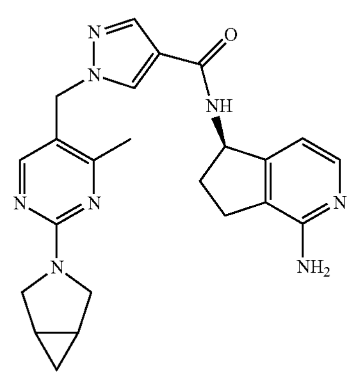 [SMILES: Cc1nc(N2CC3CC3C2)ncc1Cn1cc(C(=O)N[C@@H]2CCc3c2ccnc3N)cn1] | Acid: Intermediate 26 (50 mg) Amine: Intermediate 31 (71 mg) | LC (Method 2): t$_R$ = 3.47 min; Mass spectrum (ESI$^+$): m/z = 431 [M + H]$^+$ (overnight reaction at room temperature) |

| Example | Structure | Starting intermediates | Analysis |
|---|---|---|---|
| 12 | 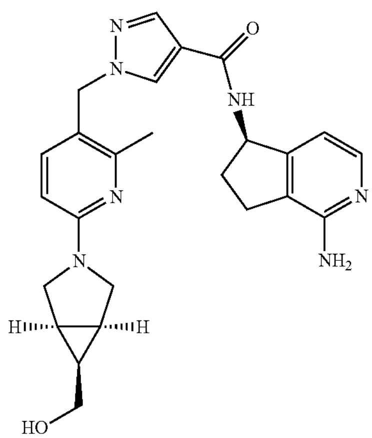 [SMILES: Cc1nc(N2C[C@@H]3[C@H](CO)[C@@H]3C2)ccc1Cn1cc(C(=O)N[C@@H]2CCc3c2ccnc3N)cn1] | Acid: Intermediate 27 (70 mg) Amine: Intermediate 31 (56 mg) | LC (Method 5): $t_R$ = 2.14 min; Mass spectrum (ESI$^+$): m/z = 460 [M + H]$^+$ |
Example 13
N-[(5R)-1-Amino-5H,6H,7H-cyclopenta[c]pyridin-5-yl]-1-({6-[(1R,5S,6R)-6-cyano-3-azabicyclo[3.1.0]hexan-3-yl]-2-methylpyridin-3-yl}methyl)-1H-pyrazole-4-carboxamide
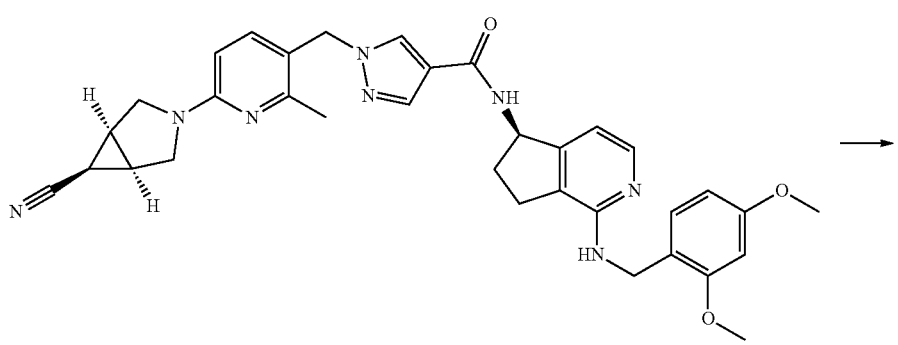
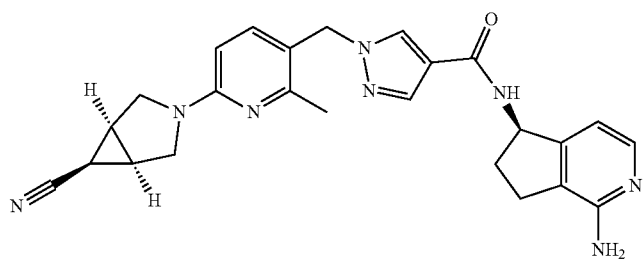

1-({6-[(1R,5S,6R)-6-Cyano-3-azabicyclo[3.1.0]hexan-3-yl]-2-methylpyridin-3-yl}-methyl)-N-[(5R)-1-{[(2,4-dimethoxyphenyl)methyl]amino}-5H,6H,7H-cyclopenta[c]pyridin-5-yl]-1H-pyrazole-4-carboxamide (Intermediate 34, 10 mg) is dissolved in dry dichloromethane (2 mL) and cooled to 0° C. Trifluoroacetic acid (0.2 mL) is added and the mixture is stirred for 1 hour. The solvent is evaporated, the residue redissolved in acetonitrile and loaded onto a prewashed SCX strong ion exchange cartridge. The cartridge is washed with acetonitrile, water and methanol and the product eluted with 7M ammonia in methanol. The solvent is evaporated and the residue dried under vacuum to give the title compound.

LC (Method 2): $t_R$=3.08 min; Mass spectrum (ESI$^+$): m/z=455 [M+H]$^+$.

The following example is prepared in analogy to Example 13, starting from the corresponding intermediates:

| Example | Structure | Starting intermediates | Analysis |
|---|---|---|---|
| 14 | 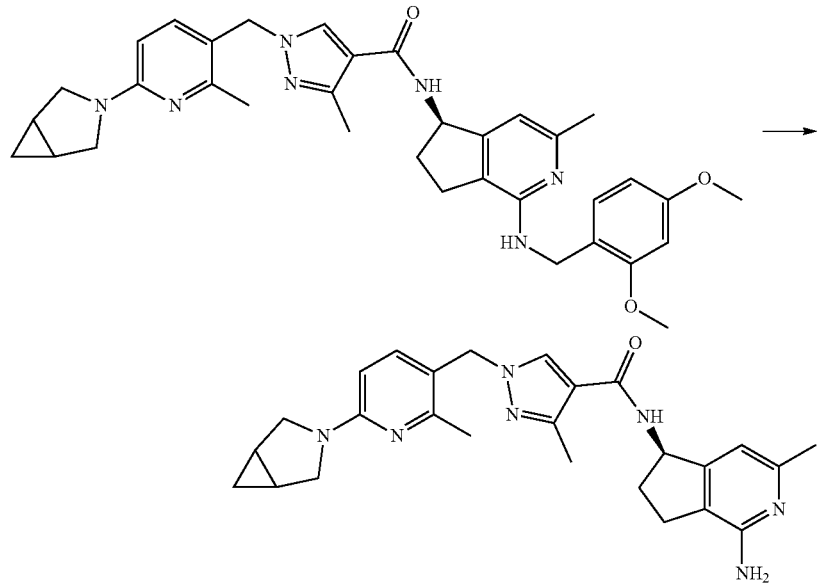 | Intermediate 35 (159 mg) | LC (Method 2): $t_R$ = 3.68 min; Mass spectrum (ESI$^+$): m/z = 444 [M + H]$^+$ |

Example 15

N-[(5R)-1-Amino-3-methyl-5H,6H,7H-cyclopenta[c]pyridin-5-yl]-1-[(6-{3-azabicyclo[3.1.0]hexan-3-yl}-2-methylpyridin-3-yl)methyl]-3-methyl-1H-pyrazole-4-carboxamide 1-[(6-{3-Azabicyclo[3.1.0]hexan-3-yl}-2-methylpyridin-3-yl)methyl]-N-[(5R)-1-{[(2,4-dimethoxyphenyl)methyl]amino}-3-methyl-5H,6H,7H-cyclopenta[c]pyridin-5-yl]-3-methyl-1H-pyrazole-4-carboxamide (Intermediate 36, 150 mg) is dissolved in dry dichloromethane (2 mL). Trifluoroacetic acid (0.5 mL) is added and the mixture is stirred for 2 hours. The solvents are evaporated in vacuo. The residue is dissolved in dichloromethane and extracted with saturated aqueous solution of K$_2$CO$_3$. The aqueous is 3 times extracted with 5% methanol in dichloromethane. The combined organic phases are dried (MgSO$_4$) and the solvents are evaporated in vacuo. The residue is purified by chromatography on Al$_2$O$_3$ (1% methanol in dichloromethane). The product thus obtained is further purified by SFC separation on chiral phase (column: CHIRAL ART® Amylose-SA, 5 μm, 250 mm×20 mm; eluent: scCO$_2$/20 mM ammonia in methanol 70:30, 40° C., 150 bar, 60 mL/min) to give the title compound.

LC (Method 7): t$_R$=0.66 min; Mass spectrum (ESI$^+$): m/z=458 [M+H]$^+$.

Example 16

N-[(5R)-1-Amino-5H,6H,7H-cyclopenta[c]pyridin-5-yl]-1-[(2-{3-azabicyclo[3.1.0]hexan-3-yl}-4-methylpyrimidin-5-yl)methyl]-1H-1,2,3-triazole-4-carboxamide

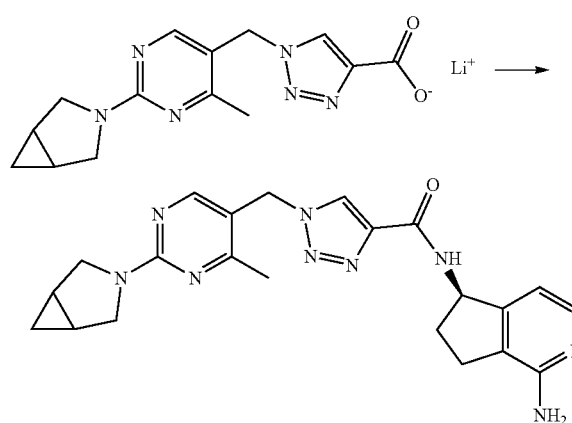

1-[(2-{3-Azabicyclo[3.1.0]hexan-3-yl}-4-methylpyrimidin-5-yl)methyl]-1H-1,2,3-triazole-4-carboxylic acid, lithium salt (10 mg) is dissolved in N,N-dimethylformamide (500 μL), treated with HATU (12.4 mg) and stirred for 10 minutes at room temperature. (5R)-5H,6H,7H-Cyclopenta[c]pyridine-1,5-diamine (4.9 mg) and N,N-diisopropylethylamine (20 μL) are added and the mixture is stirred for 3 hours at room temperature. The mixture is purified by HPLC on reversed phase (acetonitrile, water, ammonia) to give the title compound.

LC (Method 8): t$_R$=0.86 min; Mass spectrum (ESI$^+$): m/z=432 [M+H]$^+$.

Example 17

N-[(5R)-1-Amino-3-methyl-5H,6H,7H-cyclopenta[c]pyridin-5-yl]-1-[(2-{3-azabicyclo[3.1.0]hexan-3-yl}-4-methylpyrimidin-5-yl)methyl]-1H-pyrazole-4-carboxamide

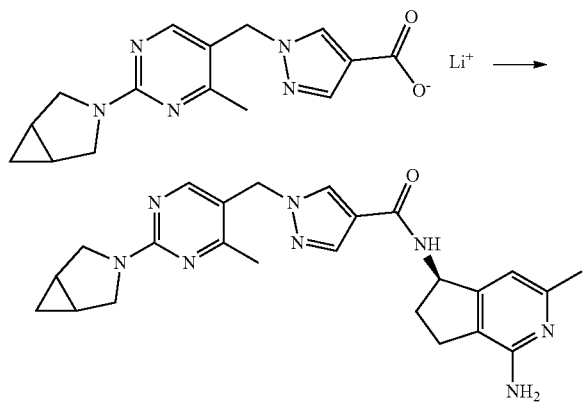

1-[(2-{3-Azabicyclo[3.1.0]hexan-3-yl}-4-methylpyrimidin-5-yl)methyl]-1H-pyrazole-4-carboxylic acid, lithium salt (10 mg) is dissolved in N,N-dimethylformamide (500 μL), treated with HATU (12.5 mg) and stirred for 10 minutes at room temperature. (5R)-3-Methyl-5H,6H,7H-cyclopenta[c]pyridine-1,5-diamine dihydrochloride (7.7 mg) and N,N-diisopropylethylamine (20 μL) are added and the mixture is stirred for 12 hours at room temperature. The mixture is purified by HPLC on reversed phase (acetonitrile, water, ammonia) to give the title compound.

LC (Method 7): t$_R$=0.68 min; Mass spectrum (ESI$^+$): m/z=445 [M+H]$^+$.

Example 18

N-[(5R)-1-Amino-3-methyl-5H,6H,7H-cyclopenta[c]pyridin-5-yl]-1-[(2-{3-azabicyclo[3.1.0]hexan-3-yl}-4-methylpyrimidin-5-yl)methyl]-1H-1,2,3-triazole-4-carboxamide

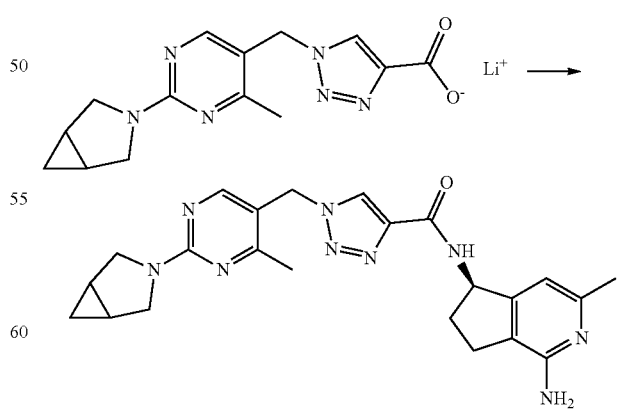

1-[(2-{3-Azabicyclo[3.1.0]hexan-3-yl}-4-methylpyrimidin-5-yl)methyl]-1H-1,2,3-triazole-4-carboxylic acid, lithium salt (10 mg) is dissolved in N,N-dimethylformamide (500 μL), treated with HATU (12.4 mg) and stirred for 10 minutes at room temperature. (5R)-3-Methyl-5H,6H,7H-cyclopenta[c]pyridine-1,5-diamine dihydro-chloride (7.7 mg) and N,N-diisopropylethylamine (20 μL) are added and the mixture is stirred for 3 hours at room temperature. The mixture is purified by HPLC on reversed phase (acetonitrile, water, ammonia) to give the title compound.

LC (Method 8): $t_R$=0.89 min; Mass spectrum (ESI$^+$): m/z=446 [M+H]$^+$.

Example 19

N-[(5R)-1-Amino-5H,6H,7H-cyclopenta[c]pyridin-5-yl]-1-[(6-{3-azabicyclo[3.1.0]hexan-3-yl}-2-methylpyridin-3-yl)methyl]-3-(difluoromethyl)-1H-pyrazole-4-carboxamide

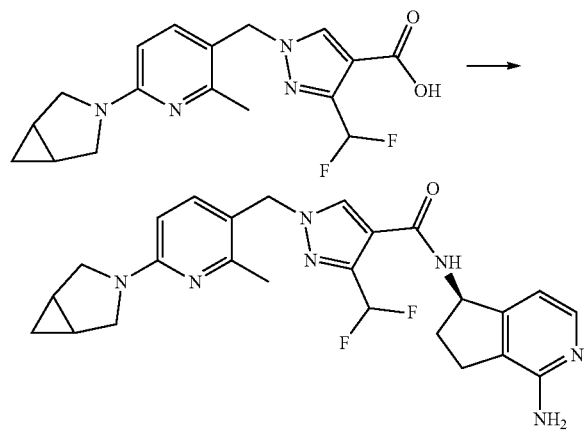

1-[(6-{3-Azabicyclo[3.1.0]hexan-3-yl}-2-methylpyridin-3-yl)methyl]-3-(difluoromethyl)-1H-pyrazole-4-carboxylic acid, trifluoroacetic acid salt (46 mg) and N,N-diisopropylethylamine (100 μL) are dissolved in N,N-dimethylformamide (2 mL), treated with HATU (40 mg) and stirred for 5 minutes at room temperature. (5R)-5H,6H,7H-Cyclopenta[c]pyridine-1,5-diamine dihydrochloride (23 mg) is added and the mixture is stirred for 12 hours at room temperature. The mixture is purified by HPLC on reversed phase (acetonitrile, water, trifluoroacetic acid) to give the title compound.

LC (Method 10): $t_R$=0.39 min; Mass spectrum (ESI$^+$): m/z=480 [M+H]$^+$.

Example 20

N-[(5R)-1-Amino-5H,6H,7H-cyclopenta[c]pyridin-5-yl]-1-[(2-{6,6-difluoro-3-azabicyclo[3.1.0]hexan-3-yl}-4-methylpyrimidin-5-yl)methyl]-1H-1,2,3-triazole-4-carboxamide

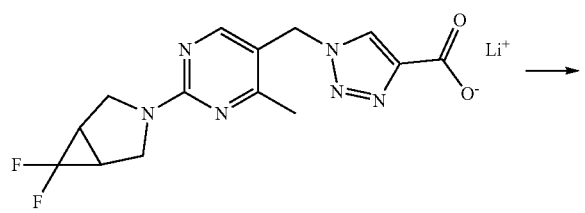

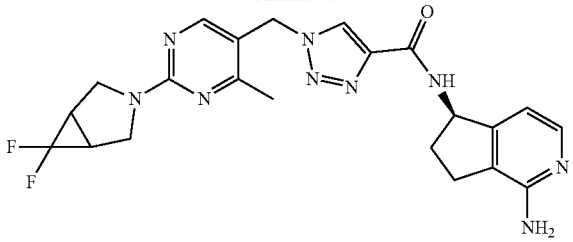

1-[(2-{6,6-Difluoro-3-azabicyclo[3.1.0]hexan-3-yl}-4-methylpyrimidin-5-yl)methyl]-1H-1,2,3-triazole-4-carboxylic acid, lithium salt (10 mg) is dissolved in N,N-dimethylformamide (500 μL), treated with HATU (11 mg) and stirred for 10 minutes at room temperature. (5R)-5H,6H,7H-Cyclopenta[c]pyridine-1,5-diamine (4.4 mg) and N,N-diisopropylethylamine (20 μL) are added and the mixture is stirred for 3 hours at room temperature. The mixture is purified by HPLC on reversed phase (acetonitrile, water, ammonia) to give the title compound.

LC (Method 8): $t_R$=0.85 min; Mass spectrum (ESI$^+$): m/z=468 [M+H]$^+$.

Example 21

N-[(5R)-1-Amino-3-methyl-5H,6H,7H-cyclopenta[c]pyridin-5-yl]-1-[(2-{6,6-difluoro-3-azabicyclo[3.1.0]hexan-3-yl}-4-methylpyrimidin-5-yl)methyl]-1H-1,2,3-triazole-4-carboxamide

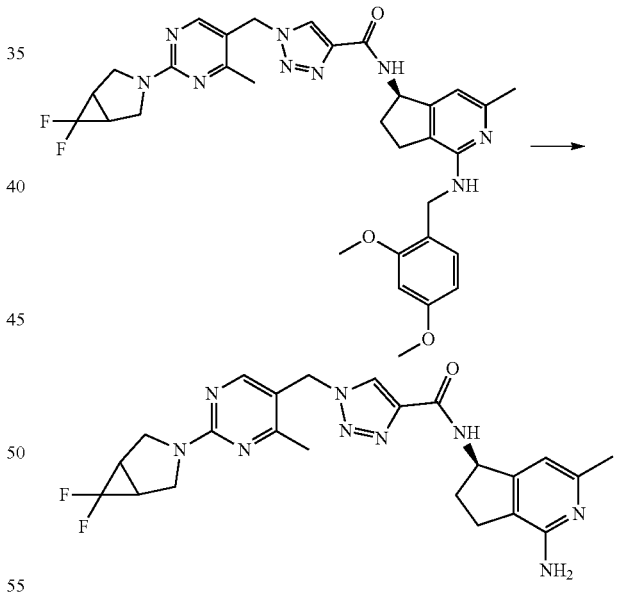

A mixture of 1-[(2-{6,6-difluoro-3-azabicyclo[3.1.0]hexan-3-yl}-4-methylpyrimidin-5-yl)methyl]-N-[(5R)-1-{[(2,4-dimethoxyphenyl)methyl]amino}-3-methyl-5H,6H,7H-cyclopenta[c]pyridin-5-yl]-1H-1,2,3-triazole-4-carboxamide (19 mg) and concentrated aqueous hydrochloric acid (1 mL) is stirred for 30 minutes at room temperature. The solvent is evaporated in vacuo, the residue dissolved in methanol and basified by addition of triethylamine. Then the mixture is purified by HPLC on reversed phase (acetonitrile, water, ammonia) to give the title compound.

LC (Method 7): $t_R$=0.75 min; Mass spectrum (ESI⁺): m/z=482 [M+H]⁺.

Example 22

N-[(5R)-1-Amino-5H,6H,7H-cyclopenta[c]pyridin-5-yl]-1-[(6-{3-azabicyclo[3.1.0]hexan-3-yl}-2-methylpyridin-3-yl)methyl]-3-methoxy-1H-pyrazole-4-carboxamide

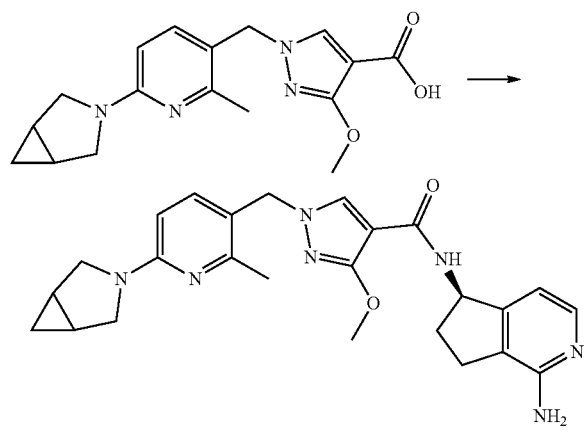

1-[(6-{3-Azabicyclo[3.1.0]hexan-3-yl}-2-methylpyridin-3-yl)methyl]-3-methoxy-1H-pyrazole-4-carboxylic acid, trifluoroacetic acid salt (44 mg) and N,N-diisopropylethylamine (100 µL) are dissolved in N,N-dimethylformamide (2 mL), treated with HATU (40 mg) and stirred for 5 minutes at room temperature. (5R)-5H,6H,7H-Cyclopenta[c]pyridine-1,5-diamine dihydrochloride (23 mg) is added and the mixture is stirred for 12 hours at room temperature. The mixture is purified by HPLC on reversed phase (acetonitrile, water, trifluoroacetic acid). The product thus obtained is purified by HPLC on reversed phase (acetonitrile, water, ammonia) to give the title compound.

LC (Method 10): $t_R$=0.36 min; Mass spectrum (ESI⁺): m/z=460 [M+H]⁺.

Example 23

N-[(5R)-1-Amino-5H,6H,7H-cyclopenta[c]pyridin-5-yl]-1-[(6-{6,6-dimethyl-3-azabicyclo[3.1.0]hexan-3-yl}-2-methylpyridin-3-yl)methyl]-1H-pyrazole-4-carboxamide

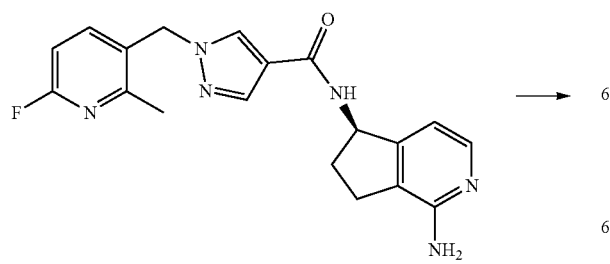

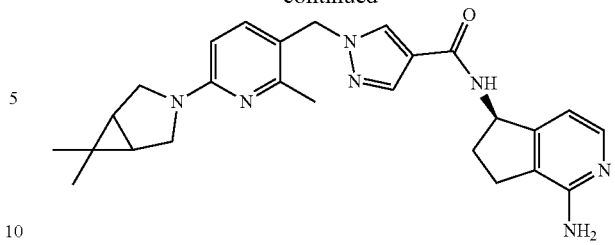

A mixture of N-[(5R)-1-amino-5H,6H,7H-cyclopenta[c]pyridin-5-yl]-1-[(6-fluoro-2-methylpyridin-3-yl)methyl]-1H-pyrazole-4-carboxamide (50 mg), 6,6-dimethyl-3-azabicyclo[3.1.0]hexane (23 mg) and N,N-diisopropylethylamine (70 µL) in dimethylsulfoxide (1 mL) is heated to 100° C. for 12 hours. The mixture is purified by HPLC on reversed phase (acetonitrile, water, ammonia) to give the title compound.

LC (Method 11): $t_R$=0.79 min; Mass spectrum (ESI⁺): m/z=458 [M+H]⁺.

Example 24

1-[2-Methyl-6-((1S,5R,6R)-6-methyl-3-aza-bicyclo[3.1.0]hex-3-yl)-pyridin-3-ylmethyl]-1H-pyrazole-4-carboxylic acid ((R)-1-amino-6,7-dihydro-5H-[2]pyrindin-5-yl)-amide

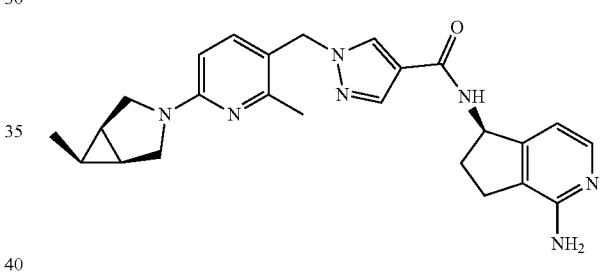

The title compound is prepared from N-[(5R)-1-amino-5H,6H,7H-cyclopenta[c]pyridin-5-yl]-1-[(6-fluoro-2-methylpyridin-3-yl)methyl]-1H-pyrazole-4-carboxamide and (1S,5R,6R)-6-methyl-3-aza-bicyclo[3.1.0]hexane following a procedure analogous to that described for Example 23. LC (method 12): $t_R$=0.74 min; Mass spectrum,
ESI pos.+neg. (Loop-Inj.): m/z=444 [M+H]⁺.

Example 25

1-[6-(2-Aza-spiro[3.3]hept-2-yl)-2-methyl-pyridin-3-ylmethyl]-1H-pyrazole-4-carboxylic acid ((R)-1-amino-6,7-dihydro-5H-[2]pyrindin-5-yl)-amide

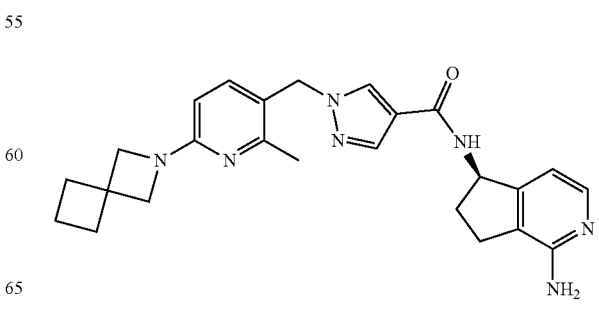

The title compound is prepared from N-[(5R)-1-amino-5H,6H,7H-cyclopenta[c]pyridin-5-yl]-1-[(6-fluoro-2-methylpyridin-3-yl)methyl]-1H-pyrazole-4-carboxamide and 2-aza-spiro[3.3]heptane following a procedure analogous to that described for Example 23. LC (method 12): $t_R$=0.70 min; Mass spectrum, ESI pos.+neg. (Loop-Inj.): m/z=444 [M+H]$^+$.

Example 26

1-[6-(5-Aza-spiro[2.3]hex-5-yl)-2-methyl-pyridin-3-ylmethyl]-1H-pyrazole-4-carboxylic acid ((R)-1-amino-6,7-dihydro-5H-[2]pyrindin-5-yl)-amide

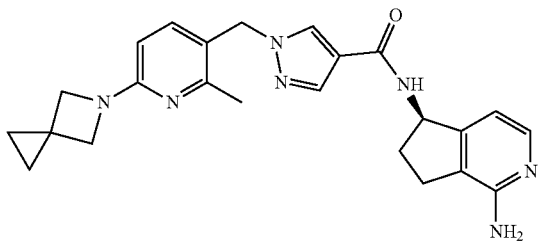 [SMILES: Cc1nc(N2CC3(CC3)C2)ccc1Cn1cc(C(=O)N[C@@H]2CCc3c2ccnc3N)cn1]

The title compound is prepared from N-[(5R)-1-amino-5H,6H,7H-cyclopenta[c]pyridin-5-yl]-1-[(6-fluoro-2-methylpyridin-3-yl)methyl]-1H-pyrazole-4-carboxamide and (1S,5R,6R)-6-methyl-3-aza-bicyclo[3.1.0]hexane following a procedure analogous to that described for Example 23. LC (method 11): $t_R$=0.61 min; Mass spectrum, ESI pos.+neg. (Loop-Inj.): m/z=430 [M+H]$^+$.

The invention claimed is:
1. A compound of formula (I)

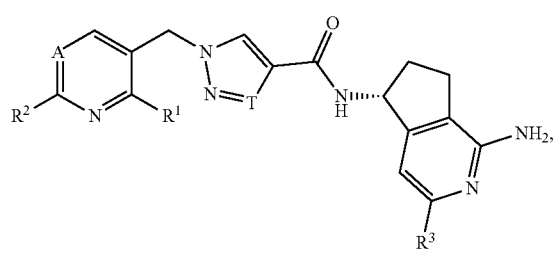

(I)

wherein
A is selected from the group A-G1 consisting of N and CH;
T is selected from the group T-G1 consisting of N, C—H, C—C$_{1-4}$-alkyl, C—CHF$_2$, C—CF$_3$ and C—OCH$_3$;
R$^1$ is selected from the group R$^1$-G1 consisting of C$_{1-3}$-alkyl;
R$^2$ is selected from the group R$^2$-G1 consisting of a fused or spiro bicyclic ring system consisting of 1 N atom and 5 to 6 C atoms as ring members, wherein the ring system is attached via the N atom to the monocyclic heteroaromatic ring in formula (I) and wherein the ring system is optionally substituted with one substituent selected from the group consisting of F, C$_{1-3}$-alkyl, CF$_3$, CN, HO—C$_{1-3}$-alkyl- and C$_{1-3}$-alkyloxy- and wherein the ring system is optionally additionally substituted with one substituent selected from the group consisting of F and CH$_3$; and
R$^3$ is selected from the group R$^3$-G1 consisting of H, CH$_3$, CHF$_2$ or CF$_3$,
or a salt thereof.

2. The compound according to claim 1, wherein
A is CH,
or a salt thereof.

3. The compound according to claim 1, wherein
A is N,
or a salt thereof.

4. The compound according to claim 1, wherein
T is selected from the group T-G3 consisting of N, C—H, C—CH$_3$, C—CH(CH$_3$)$_2$, C—CHF$_2$, C—CF$_3$ and C—OCH$_3$,
or a salt thereof.

5. The compound according to claim 1, wherein
R$^1$ is CH$_3$,
or a salt thereof.

6. The compound according to claim 1, wherein
R$^2$ is selected from the group R$^2$-G4 consisting of

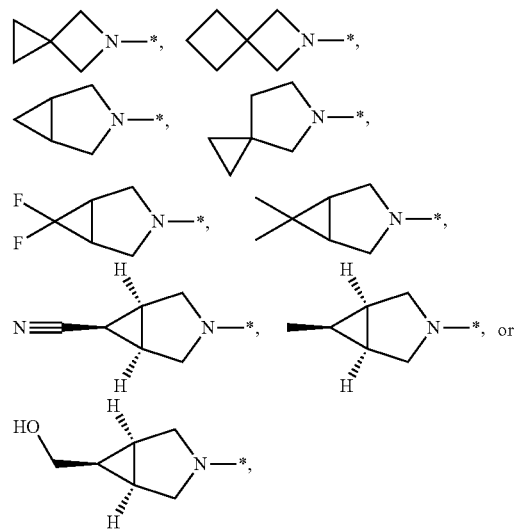

wherein, as indicated by the asterisk, the ring system is attached via the N atom to the monocyclic heteroaromatic ring in formula (I),
or a salt thereof.

7. The compound according to claim 1, wherein
R$^3$ is selected from the group R$^3$-G2 consisting of H and CH$_3$,
or a salt thereof.

8. The compound according to claim 1, wherein the compound of formula (I) is selected from the group consisting of

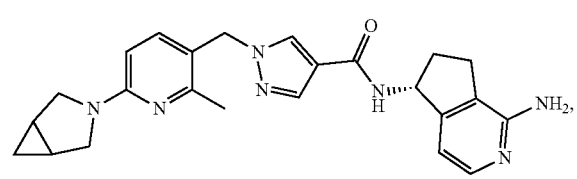

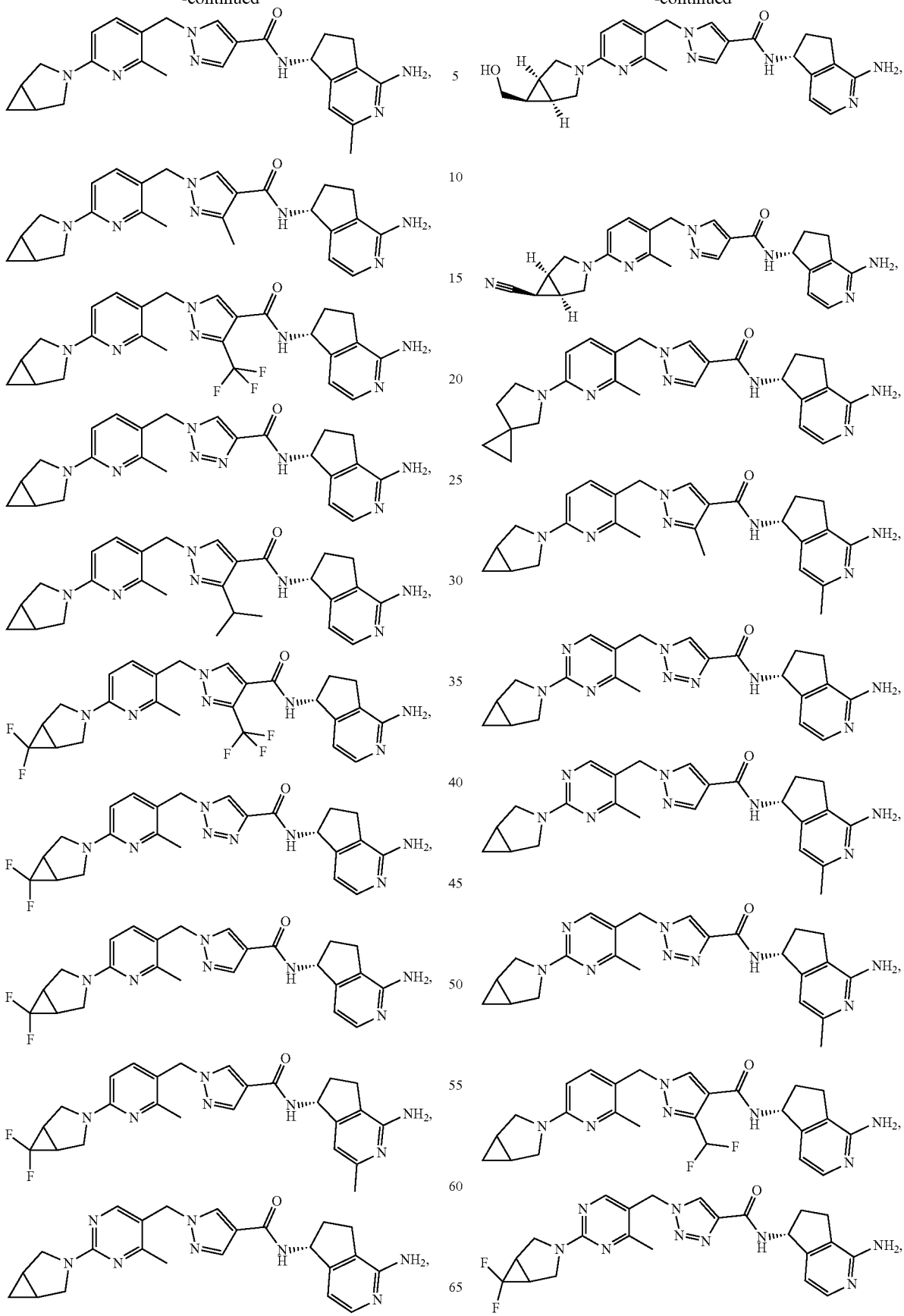

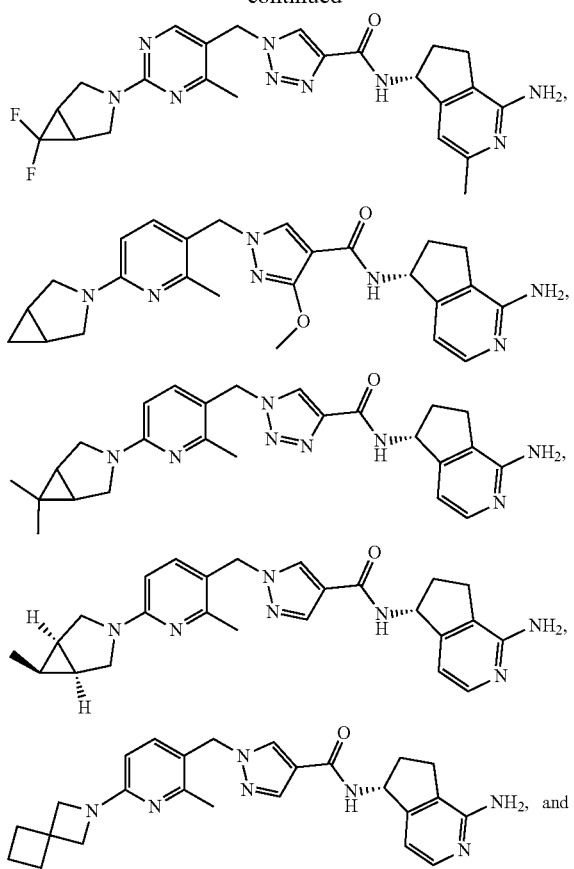

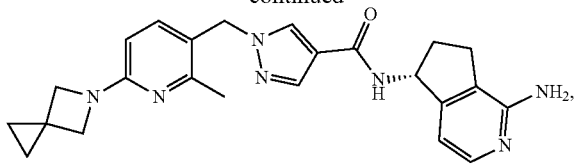

or a salt thereof.

9. A pharmaceutically acceptable salt of a compound according to claim 1.

10. A pharmaceutical composition comprising one or more compounds according to claim 1, or pharmaceutically acceptable salts thereof, optionally together with one or more inert carriers and/or diluents.

11. A pharmaceutical composition comprising one or more compounds according to claim 1, or pharmaceutically acceptable salts thereof, and one or more additional therapeutic agents, optionally together with one or more inert carriers and/or diluents.

12. The pharmaceutical composition according to claim 11 wherein the one or more additional therapeutic agents are selected from the group consisting of antidiabetic agents, agents for the treatment of overweight and/or obesity, agents for the treatment of high blood pressure, heart failure and/or atherosclerosis and agents for the treatment of ocular diseases.

13. A method for treatment of diabetic complications, in a patient in need thereof, the method comprising administering a compound according to claim 1, or pharmaceutically acceptable salts thereof, to the patient.

14. The method according to claim 13, wherein the diabetic complication is retinal vascular permeability associated with diabetic retinopathy or diabetic macular edema.

* * * * *